US012534437B2

(12) United States Patent
Nicewicz et al.

(10) Patent No.: US 12,534,437 B2
(45) Date of Patent: *Jan. 27, 2026

(54) PHOTOREDOX-CATALYZED DIRECT C—H FUNCTIONALIZATION OF ARENES

(71) Applicant: The University of North Carolina at Chapel Hill, Chapel Hill, NC (US)

(72) Inventors: David Nicewicz, Durham, NC (US); Nathan Romero, Carrboro, NC (US); Kaila Margrey, Chapel Hill, NC (US); Nicholas Tay, Chapel Hill, NC (US)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 18/159,647

(22) Filed: Jan. 25, 2023

(65) Prior Publication Data

US 2023/0167067 A1 Jun. 1, 2023

Related U.S. Application Data

(63) Continuation of application No. 16/506,901, filed on Jul. 9, 2019, now Pat. No. 11,584,720, which is a continuation of application No. 15/826,092, filed on Nov. 29, 2017, now Pat. No. 10,399,947, which is a continuation of application No. PCT/US2016/035549, filed on Jun. 2, 2016.

(60) Provisional application No. 62/170,632, filed on Jun. 3, 2015.

(51) Int. Cl.

| | |
|---|---|
| ***C07D 231/12*** | (2006.01) |
| ***B01J 31/02*** | (2006.01) |
| ***B01J 35/00*** | (2024.01) |
| ***B01J 35/39*** | (2024.01) |
| ***C07C 41/22*** | (2006.01) |
| ***C07C 67/05*** | (2006.01) |
| ***C07C 209/80*** | (2006.01) |
| ***C07C 213/02*** | (2006.01) |
| ***C07C 217/84*** | (2006.01) |
| ***C07C 253/30*** | (2006.01) |
| ***C07D 207/50*** | (2006.01) |
| ***C07D 219/02*** | (2006.01) |
| ***C07D 231/38*** | (2006.01) |
| ***C07D 249/08*** | (2006.01) |
| ***C07D 403/04*** | (2006.01) |

(52) U.S. Cl.

CPC ........ *C07D 231/12* (2013.01); *B01J 31/0244* (2013.01); *B01J 35/39* (2024.01); *C07C 41/22* (2013.01); *C07C 67/05* (2013.01); *C07C 209/80* (2013.01); *C07C 213/02* (2013.01); *C07C 217/84* (2013.01); *C07C 253/30* (2013.01); *C07D 207/50* (2013.01); *C07D 219/02* (2013.01); *C07D 231/38* (2013.01); *C07D 249/08* (2013.01); *C07D 403/04* (2013.01)

(58) Field of Classification Search

None

See application file for complete search history.

(56) References Cited

U.S. PATENT DOCUMENTS

| | | | |
|---|---|---|---|
| 4,483,757 | A | 11/1984 | Gardner et al. |
| 9,452,959 | B2 | 9/2016 | Hartwig et al. |
| 2012/0171111 | A1 | 7/2012 | Ohkubo et al. |
| 2018/0148414 | A1 | 5/2018 | Hartwig et al. |

FOREIGN PATENT DOCUMENTS

| | | |
|---|---|---|
| JP | 2002-114735 | 4/2002 |
| JP | 2005-145853 | 6/2005 |
| WO | WO 2016/196816 | 12/2016 |
| WO | WO-2016/196816 A1 | 12/2016 |

OTHER PUBLICATIONS

CAPLUS printout of Wilger et. al., The direct anti-Markovnikov addition of mineral acids to styrenes. Nature Chemistry, 2014, 6, 720-726.*

Grant & Hackh's Chemical Dictionary (5th Ed. 1987) at p. 148.*

CAPLUS printout of Foreign Patent No. JP2010059141, published on Mar. 18, 2010.*

An updated CAPLUS printout of "Wilger et.al., The direct anti-Markovnikov addition of mineral acids to styrenes. Nature Chemistry, 2014, 6, 720-726."*

U.S. Appl. No. 62/170,632, filed Jun. 3, 2015, David Nicewicz (The Univ. of NC at Chapel Hill).

U.S. Appl. No. 15/826,092 (U.S. Pat. No. 10,399,947), filed Nov. 29, 2017 (Sep. 3, 2019), David Nicewicz (The Univ. of NC at Chapel Hill).

U.S. Appl. No. 16/506,901 (U.S. Pat. No. 11,584,720), filed Jul. 9, 2019 (Feb. 21, 2023), David Nicewicz (The Univ. of NC at Chapel Hill).

U.S. Appl. No. 62/812,179, filed Feb. 28, 2019, Zibo Li (The Univ. of NC at Chapel Hill).

U.S. Appl. No. 17/434,677, filed Aug. 27, 2021, Zibo Li (The Univ. of NC at Chapel Hill).

PCT/US2016/035549, Jun. 2, 2016, David Nicewicz (The Univ. of NC at Chapel Hill).

PCT/US2020/020232, Feb. 27, 2020, Zibo Li (The Univ. of NC of Chapel Hill).

Allen et al., N-Acyloxyphthalimides as Nitrogen Radical Precursors in the Visible Light Photocatalyzed Room Temperature C—H Amination of Arenes and Heteroarenes. J Am Chem Soc. 2014; 136(15):5607-10.

(Continued)

*Primary Examiner* — Po-Chih Chen

(74) *Attorney, Agent, or Firm* — J. Clinton Wimbish; Maynard Nexsen PC

(57) ABSTRACT

The invention generally relates to methods of making substituted arenes via direct C—H amination. More specifically, methods of making para- and ortho-substituted arenes via direct C—H amination are disclosed. This abstract is intended as a scanning tool for purposes of searching in the particular art and is not intended to be limiting of the present invention.

16 Claims, 1 Drawing Sheet

(56) References Cited

OTHER PUBLICATIONS

Almarasson, Ö. et al., Crystal Engineering of the Composition of Pharmaceutical Phases. Do Pharmaceutical Co-crystals Represent a New Path to Improved Medicines? The Royal Soc Chem. 2004; 1889-96.
Antonchick et al., Organocatalytic, Oxidative, Intramolecular C—H Bond Amination and Metal-free Cross-Amination of Unactivated Arenes at Ambient Temperature. Angew Chem Int Ed Engl. 2011; 50(37): 8605-8.
Belfield et al., Recent synthetic advances in the nucleophilic amination of benzenes. Tetrahedron. 1999; 55(38):11399-428.
Benniston, et al. (2005) "Charge Shift and Triplet State Formation in the 9-Mesityl-10-methylacridinium Cation," J. Am. Chem. Soc. 127: 16054-16064.
Benniston, et al. (2008) "Comment: Electron-transfer reactions in the 9-mesityl-10-methylacridinium ion: impurities, triplet states and infinitely long-lived charge-shift states?" Phys Chem Chem Phys. 10(33):5156-8.
Brachet et al., Visible light C—H amidation of heteroarenes with benzoyl azides. Chem Sci., 2015; 6: 987-92.
Fukuzumi, et al. (2004) "Electron-Transfer State of 9-Mesityl-10-methylacridinium Ion with a Much Longer Lifetime and Higher Energy Than That of the Natural Photosynthetic Reaction Center" J. Am. Chem. Soc. 126: 1600-1601.
Fukuzumi, et al. (2014) "Long-Lived Charge Separation and Applications in Artificial Photosynthesis," Acc. Chem. Res. 47: 1455-1464.
Gendron, et al. (2018), "Ring-Closing Synthesis of Dibenzothiophene Sulfonium Salts and Their Use as Leaving Groups for Aromatic 18F-Fluorination" J. Am. Chem. Soc. (2018), doi:10.1021/jacs.8b06730.
Hamilton, D.S. and Nicewicz, D.A. et al., Direct Catalytic Anti-Markovnikov Hydroetherification of Alkenols. J Am Chem Soc. 2012; 134(45): 18577-80.
Hartwig, Evolution of a Fourth Generation Catalyst for the Amination and Thioetherification of Aryl Halides. Acc Chem Res. 2008; 41(11):1534-44.
Ichiishi, et al. (2014) "Copper-Catalyzed [18F]Fluorination of (Mesityl)(aryl)iodonium Salts," Org. Lett. 16, 3224-3227 (2014).
Lee, et al. (2012) "Flouride-Derived Electrophilic Late-Stage Fluorination Reagent for PET Imaging," *Science* 334: 639-642.
Lee, et al. (2012) "Nickel-Mediated Oxidative Fluorination for PET Aqueous [$^{18}$F] Flouride," *J. Am. Chem. Soc.*, 134: 17456-17458.
Lee, et al. (2015) "Virtually instantaneous, room-temperature [(11)C]-cyanation using biaryl phosphine Pd(0) complexes," J. Am. Chem. Soc. 137: 648-651.
Liwosz, T. et al., Copper-Catalyzed Synthesis of N-Aryl and N-Sulfonyl Indoles from 2-Vinylanilines with 02 as Terminal Oxidant and TEMPO as Co-Catalyst. Synlett. 2014; 26(3):33.
Makaravage, et al. (2016) "Copper-Mediated Radiofluorinationof Arylstannanes with [$^{18}$F]KF," Org. Lett. 18: 5440-5443.
Matsubara et al., Synthesis of Anthranilic Acid Derivatives through Iron-Catalyzed Ortho Amination of Aromatic Carboxamides with N-Chloroamines. J Am Chem Soc. 2014; 136(2): 646-9.
McCammant, et al. (2017), "Cu-Mediated C—H 18F-Fluorination of Electron-Rich (Hetero)arenes," Org. Lett. 19, 3939-3942.
McManus, et al., Direct C—H Cyanation of Arenes via Organic Photoredox Catalysis, J Am Chem Soc 2017; 139: 2880-2883.
Morofuji et al., Direct C—N Coupling of Imidazoles with Aromatic and Benzylic Compounds via Electrooxidative C—H Functionalization. J Am Chem Soc. 2014; 136(12): 4496-9.
Mossine, et al. (2015) "Synthesis of [$^{18}$F]Arenes via the Cooper-Mediated [$^{18}$F]Fluorination of Boronic Acids," Org. Lett. 17: 5780-5783.
Narayanam (2017) "Synthesis of [18F]Fluoroarenes via Nucleophilic Radiofluorination of N-Arylsydnones," Angew. Chem. Int. Ed. 56, 13006-13010.
Neumann, et al. (2016) "Concerted nucleophilic aromatic substitution with 19F- and 18F-" Nature 534: 369-373.
Nguyen et al., Anti-Markovnikov hydroamination of alkenes catalyzed by a two-component organic photoredox system: direct access to phenethylamine derivatives. Angew Chem Int Ed Engl. 2014; 53(24):6198-201.
Nguyen et al., Anti-Markovnikov Hydroamination of Alkenes Catalyzed by an Organic Photoredox System. J Am Chem Soc. 2013; 135(26): 9588-91.
Nicewicz et al., Recent Applications of Organic Dyes as Photoredox Catalysts in Organic Synthesis. ACS Catal. 2014; 4(1): 355-60.
Ohkubo, et al. Selective photocatalytic aerobic bromination with hydrogen bromidevia an electron-transfer state of 9-mesityl-10-methylacridinium ion. Chem Sci. 2011; 2(4): 715-22.
Ohkubu et al., Oxygenation and chlorination of aromatic hydrocarbons with hydrochloric acid photosensitized by 9-mesityl-10-methylacridinium under visible light irradiation. Res Chem Intermed. 2013; 39:205-20.
Pan, et al. (1993) "Hydroxyl-radical-induced oxidation of cyclohexa-1,4-diene by O2 in aqueous solution. A pulse radiolysis and product study," J. Chem. Soc. Perkin Trans. 2: 9.
Perkowshi et al., Direct Catalytic Anti-Markovnikov Addition of Carboxylic Acids to Alkenes. J Am Chem Soc. 2013; 135(28):10334-7.
Preshlock, et al. (2016) "$^{18}$F-Labeling of Arenes and Heteroarenes for Application in Positron Emission Tomography," Chem. Rev. 116: 719-766.
Prier et al., Visible Light Photoredox Catalysis with Transition Metal Complexes: Applications in Organic Synthesis. Chem Rev. 2013; 113(7): 5322-63 (141 pages).
PubChem-SID 184611234, "9-Mesityl-2, 7-dimethyl-10-phenylacridin-10-ium tetrafluoroborate" (2014); p. 3.
Romero, et al. (2014) "Mechanistic insight into the photoredox catalysis of anti-markovnikov alkene hydrofunctionalization reactions," J. Am. Chem. Soc. 136: 17024-17035.
Schimler, et al. (2017) "Nucleophilic Deoxyfluorination of Phenols via Aryl Fluorosulfonate Intermediates," Journal of the American Chemical Society 139: 1452-1455.
Shrestha et al., Sterically Controlled, Palladium-Catalyzed Intermolecular Amination of Arenes. J Am Chem Soc. 2013; 135(23): 8480-3.
Simon M. Ametamey, et al. (2008) "Molecular imaging with PET," Chem. Rev. 108: 1501-1516.
Surry and Buchwald et al., Dialkylbiaryl phosphines in Pd-catalyzed amination: a user's guide. Chem Soc. 2011; 2(1): 27-50 (70 pages).
Tay, et al., Cation Radical Accelerated Nucleophilic Aromatic Substitution via Organic Photoredox Catalysis, J Am Chem Soc 2017; 139: 16100-16104.
Teare, et al. (2010) "Radiosynthesis and Evaluation of [18F]Selectfluor bis(triflate)" Angew. Chem. Int. Ed. 49, 6821-6824.
Tran, L.D. et al., Directed Amination of Non-Acidic Arene C—H Bonds by a Copper-Silver Catalytic System. Angew Chem Int Ed Engl. 2013; 52(23):6043-6.
Tredwell, et al. (2014) "A General Copper-Mediated Nucleophilic 18F Fluorination of Arenes," Angew. Chem. Int. Ed. 53, 7751-7755.
Tredwell, et al., 18F Labeling of Arenes, Angew Chem Int Ed 2012; 51: 11426-11437.
Truong, et al. (2013) "Copper-catalyzed, directing group-assisted fluorination of arene and heteroarene C—H bonds," Journal of the American Chemical Society 135: 9342-9345.
Tsang et al., Combined C—H Functionalization/C—N Bond Formation Route to Carbazoles. J Am Chem Soc. 2005; 127:14560-1.
Wang (2009) Versatile Pd(OTf)$_2$ 2H$_2$O-Catalyzed ortho-Fluorination Using NMP as a Promoter, Am Chem Soc. 131(22):7520-7521.
Xue, D. et al., Direct arylation of N-Heteroarenes with Aryldiazonium salts by Photoredox Catalysis in Water. Chem Eur J. 2014; 20(10):2960-5.
Yan, et al., Recent advances in radical-mediated florination through C—H and C—C bond cleavage, Science China Chemistry, 2017; 60(2): 214-222.

(56) References Cited

OTHER PUBLICATIONS

Requirement for Restriction issued on Apr. 25, 2018 by the U.S. Patent and Trademark Office for U.S. Appl. No. 15/826,092, filed Nov. 29, 2017 and issued as U.S. Pat. No. 10,399,947 on Sep. 3, 2019 (Applicant—The University of North Carolina at Chapel Hill) (17 pages).

Response to Requirement for Restriction filed on Jun. 22, 2018 with the U.S. Patent and Trademark Office for U.S. Appl. No. 15/826,092, filed Nov. 29, 2017 and issued as U.S. Pat. No. 10,399,947 on Sep. 3, 2019 (Applicant—The University of North Carolina at Chapel Hill) (13 pages).

Non-final Office Action issued on Oct. 5, 2018 by the U.S. Patent and Trademark Office for U.S. Appl. No. 15/826,092, filed Nov. 29, 2017 and issued as U.S. Pat. No. 10,399,947 on Sep. 3, 2019 (Applicant—The University of North Carolina at Chapel Hill) (10 pages).

Response to Office Action filed on Jan. 2, 2019 with the U.S. Patent and Trademark Office for U.S. Appl. No. 15/826,092, filed Nov. 29, 2017 and issued as U.S. Pat. No. 10,399,947 on Sep. 3, 2019 (Applicant—The University of North Carolina at Chapel Hill) (19 pages).

Notice of Allowance issued on Mar. 28, 2019 by the U.S. Patent and Trademark Office for U.S. Appl. No. 15/826,092, filed Nov. 29, 2017 and issued as U.S. Pat. No. 10,399,947 on Sep. 3, 2019 (Applicant—The University of North Carolina at Chapel Hill) (8 pages).

Amendment after Notice of Allowance filed on May 20, 2019 with the U.S. Patent and Trademark Office for U.S. Appl. No. 15/826,092, filed Nov. 29, 2017 and issued as U.S. Pat. No. 10,399,947 on Sep. 3, 2019 (Applicant—The University of North Carolina at Chapel Hill) (8 pages).

Notice of Allowance issued on Aug. 5, 2019 by the U.S. Patent and Trademark Office for U.S. Appl. No. 15/826,092, filed Nov. 29, 2017 and issued as U.S. Pat. No. 10,399,947 on Sep. 3, 2019 (Applicant—The University of North Carolina at Chapel Hill) (5 pages).

Non-final Office Action issued on Jun. 8, 2022 by the U.S. Patent and Trademark Office for U.S. Appl. No. 16/506,901, filed Jul. 9, 2019 and issued as U.S. Pat. No. 11,584,720 on Feb. 21, 2023 (Applicant—The University of North Carolina at Chapel Hill) (12 pages).

Response to Office Action filed on Jan. 2, 2019 with the U.S. Patent and Trademark Office for U.S. Appl. No. 16/506,901, filed Jul. 9, 2019 and issued as U.S. Pat. No. 11,584,720 on Feb. 21, 2023 (Applicant—The University of North Carolina at Chapel Hill) (13 pages).

Notice of Allowance issued on Aug. 5, 2019 by the U.S. Patent and Trademark Office for U.S. Appl. No. 16/506,901, filed Jul. 9, 2019 and issued as U.S. Pat. No. 11,584,720 on Feb. 21, 2023 (Applicant—The University of North Carolina at Chapel Hil) (10 pages).

International Search Report and Written Opinion mailed on Sep. 6, 2016 by the International Searching Authority for International Patent Application No. PCT/US2016/035549, which was filed on Jun. 2, 2016 and published as WO 2016/196816 on Dec. 8, 2016 (Applicant—The University of North Carolina at Chapel Hill) (7 pages).

International Preliminary Report on Patentability issued on Dec. 5, 2017 by the International Searching Authority for International Patent Application No. PCT/US2016/035549, which was filed on Jun. 2, 2016 and published as WO 2016/196816 on Dec. 8, 2016 (Applicant—The University of North Carolina at Chapel Hill) (6 pages).

International Search Report and Written Opinion mailed on Jun. 11, 2020 by the International Searching Authority for International Patent Application No. PCT/US2020/020232, which was filed on Feb. 27, 2020 (Applicant—The University of North Carolina at Chapel Hill) (10 pages).

International Preliminary Report on Patentability issued on Aug. 25, 2021 by the International Searching Authority for International Patent Application No. PCT/US2020/020232, which was filed on Feb. 27, 2020 (Applicant—The University of North Carolina at Chapel Hill) (8 pages).

* cited by examiner

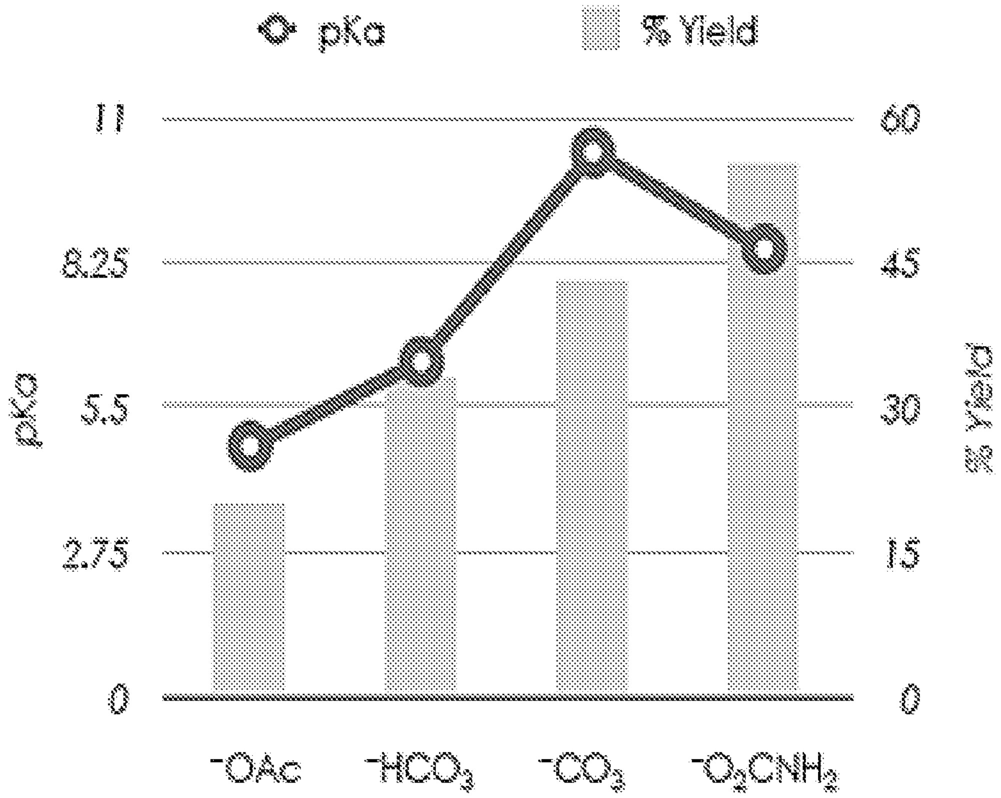
$$(H_4N)_n^+X^- \rightleftharpoons n\,NH_3 + HX$$

PHOTOREDOX-CATALYZED DIRECT C—H FUNCTIONALIZATION OF ARENES

CROSS-REFERENCE TO RELATED APPLICATIONS

This application is a continuation of U.S. application Ser. No. 16/506,901, filed Jul. 9, 2019, which a continuation of U.S. application Ser. No. 15/826,092, filed Nov. 29, 2017, which is a continuation of International Application No. PCT/US2016/035549 with an international filing date of Jun. 2, 2016, which claims priority to U.S. Provisional Application No. 62/170,632 filed on Jun. 3, 2015, the contents of which are incorporated herein by reference in their entireties.

BACKGROUND

Nitrogen-containing aromatic compounds are extremely important in the synthesis of pharmaceuticals and commodity chemicals. As such, new methods for the construction of nitrogen substituted arenes are in high demand. To achieve aryl C—N bond formation, previous methodologies have generally required a pre-installed functional handle on the arene in order to introduce the amine via a cross-coupling strategy (Belfield et al. (1999) *Tetrahedron* 55, 11399; Surry and Buchwald (2011) Chem. Soc. 2, 27; Hartwig (2008) *Acc. Chem. Res.* 41, 1534). More recent work has demonstrated the utility of arene C—H functionalization as a comparatively expedient strategy for the construction of N-arylated products; however, these methodologies are limited by several factors. The regiochemical outcome is largely dictated by a pre-installed Lewis basic directing group, which typically results in ortho selectivity (Tsang et al. (2005) *J Am. Chem. Soc.* 127, 14560; Antonchick et al. (2011) *Angew. Chem. Int. Ed.* 50, 8605; Matsubara et al. (2014) *J Am. Chem. Soc.* 136, 646; Tran et al. (2013) *Angew. Chem. Int. Ed.* 52, 6043). In the rare examples of arene amination where ortho addition is suppressed, differentiation between meta and para positions is not observed (Shrestha et al. (2013) *J Am. Chem. Soc.* 135, 8480). Additionally, these protocols often require superstoichiometric equivalents of both arene and a terminal oxidant in order to achieve synthetically useful yields (Allen et al. (2014) *J. Am. Chem. Soc.* 136, 5607; Brachet et al. (2015) *Chem. Sci.* Advance Article; Marchetti et al. *Org. Lett.* ASAP), limiting the value of this method as a tool for late stage functionalization. Despite recent advances in arene C—H functionalization, this methodology has continued to be restricted by the regioselectivity of the reaction and the substrate scope. Thus, there remains a need for direct aryl amination reactions that are tolerant to a wide range of substrates and that are regioselective.

SUMMARY

In accordance with the purpose(s) of the invention, as embodied and broadly described herein, the invention, in one aspect, relates to methods of synthesizing a substituted arene via direct C—H functionalization (e.g., amination).

Disclosed are methods of making a compound having a structure represented by a formula:

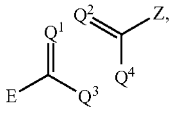

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; or wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; wherein Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —$NNR^4$, —OC(═O)$R^5$, and $Ar^1$; wherein $R^4$ is selected from hydrogen and C1-C8 alkyl; wherein $R^5$ is selected from C1-C8 alkyl; wherein $Ar^1$ is a 3- to 6-membered heterocycle substituted with 0, 1, 2, or 3 groups independently selected from halogen and C1-C8 alkyl, the method comprising the steps of: (a) reacting a compound having a structure represented by a formula:

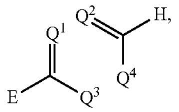

with a nucleophile selected from water, ammonia, a halide, a cyanide, an alcohol, a thiol, an amine, a hydrazine, a carbamate, a carboxylic acid, and an alkene, in the presence of a catalytically effective amount of an acridinium photocatalyst; and (b) reacting with an oxidant, thereby forming the compound.

Also disclosed are methods of making a compound having a structure represented by a formula:

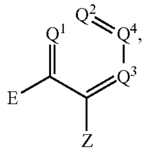

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; or wherein each of $Q^2$ and $Q^4$ is $CR^2$ and wherein each occurrence of $R^2$ are optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and —C(═O)$NR^{3a}R^{3b}$; wherein Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —$NNR^4$, —OC(═O)$R^5$, and $Ar^1$; wherein $R^4$ is selected from hydrogen and C1-C8 alkyl; wherein $R^5$ is selected from C1-C8 alkyl; wherein $Ar^1$ is a 3- to 6-membered heterocycle substituted with 0, 1, 2, or 3 groups independently selected from halogen and C1-C8 alkyl, the method comprising the steps of: (a) reacting a compound having a structure represented by a formula:

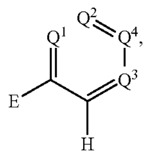

with a nucleophile selected from water, ammonia, a halide, a cyanide, an alcohol, a thiol, an amine, a hydrazine, a carbamate, a carboxylic acid, and an alkene, in the presence of a catalytically effective amount of an acridinium photocatalyst; and (b) reacting with an oxidant, thereby forming the compound.

Also disclosed are methods of making a compound having a structure represented by a formula selected from:

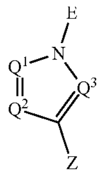

or

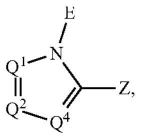

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; or wherein $R^1$ and $R^2$ are optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; wherein Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —$NNR^4$, —OC(═O)$R^5$, and $Ar^1$; wherein $R^4$ is selected from hydrogen and C1-C8 alkyl; wherein $R^5$ is selected from C1-C8 alkyl; and wherein $Ar^1$ is a 3- to 6-membered heterocycle substituted with 0, 1, 2, or 3 groups independently selected from halogen and C1-C8 alkyl, the method comprising the steps of: (a) reacting a compound having a structure represented by a formula selected from:

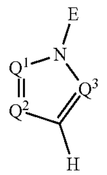

or

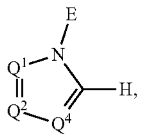

with a nucleophile selected from water, ammonia, a halide, a cyanide, an alcohol, a thiol, an amine, a hydrazine, a carbamate, a carboxylic acid, and an alkene, in the presence of a catalytically effective amount of an acridinium photocatalyst; and (b) reacting with an oxidant, thereby forming the compound are disclosed. In a further aspect, the electron donating group is selected from —OH, —SH, —$NH_2$, C1-C8 alkyl, C1-C8 alkoxy, C1-C8 thioalkoxy, C1-C8 silyloxy, C1-C8 alkylamino, (C1-C8)(C1-C8) dialkylamino, —OC(═O)$R^6$, —NHC(═O)$R^7$, —$OAr^2$, and $Ar^2$; wherein each of $R^6$ and $R^7$ is independently selected from C1-C8 alkyl; and wherein $Ar^2$ is selected from aryl and heteroaryl and substituted with 0, 1, 2, or 3 groups independently selected from halogen and C1-C8 alkyl.

Also disclosed are methods of C—H functionalization (e.g., amination) an activated arene in the presence of an acridinium photocatalyst.

Also disclosed are methods of C—H functionalization (e.g., amination) an activated arene in the absence of a transition metal catalyst.

Also disclosed are compounds having a structure represented by a formula:

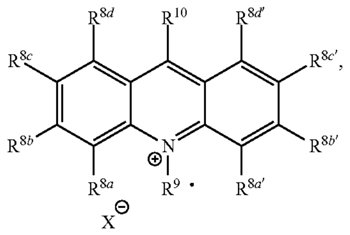

wherein X is selected from $BF_4$, TfO, $PF_6$, and $ClO_4$; wherein each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino, and phenyl substituted with 0, 1, 2, or 3 groups independently selected from halogen, —$CF_3$, —$NH_2$, C1-C4 alkyl, C1-C4 alkoxy, C1-C4 alkylamino, C1-C4 dialkylamino; wherein $R^9$ is selected from C1-C4 alkyl and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; and wherein $R^{10}$ is selected from C1-C4 alkyl and phenyl substituted with 0, 1, 2, or 3 groups independently selected from halogen and C1-C4 alkyl.

Also disclosed are catalyst systems comprising an acridinium photocatalyst, a nucleophile, and an oxidant.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying FIGURES, which are incorporated in and constitute a part of this specification, illustrate several aspects and together with the description serve to explain the principles of the invention.

FIG. 1 shows representative data indicating that the reaction yield is roughly correlated with the pKa of the conjugate acid.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "catalytically effective" refers to the amount of a catalyst that is sufficient to facilitate a reaction (e.g., C—H functionalization (e.g., amination) as disclosed herein).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more $—OCH_2CH_2O—$ units in the polyester, regardless of whether ethylene glycol was used to prepare the polyester. Similarly, a sebacic acid residue in a polyester refers to one or more $—CO(CH_2)_8CO—$ moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $(CH_2)_a—$, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2)π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NAiA^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula $N(\text{-alkyl})_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula C(O)OH.

The term "ester" as used herein is represented by the formula $OC(O)A^1$ or $C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula $(A^1O(O)C\text{-}A^2\text{-}C(O)O)_a$— or $(A^1O(O)C\text{-}A^2\text{-}OC(O))_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $-(A^1O-A^2O)_a-$, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide", as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $N_3$.

The term "nitro" as used herein is represented by the formula $-NO_2$.

The term "nitrile" or "cyano" as used herein is represented by the formula —CN.

The term "silyl" as used herein is represented by the formula $SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $S(O)A^1$, $S(O)_2A^1$, $-OS(O)_2A^1$, or $-OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula $-S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A'S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group is independently halogen; $-(CH_2)_{0-4}R^{\circ}$; $-(CH_2)_{0-4}OR^{\circ}$; $-O(CH_2)_{0-4}R^{\circ}$, $-O-(CH_2)_{0-4}C(O)OR^{\circ}$; $-(CH_2)_{0-4}CH(OR^{\circ})_2$; $-(CH_2)_{0-4}SR^{\circ}$; $-(CH_2)_{0-4}Ph$, which may be substituted with $R^{\circ}$; $-(CH_2)_{0-4}O(CH_2)_{0-1}Ph$ which may be substituted with $R^{\circ}$; $-CH{=}CHPh$, which may be substituted with $R^{\circ}$; $-(CH_2)_{0-4}O(CH_2)_{0-1}$-pyridyl which may be substituted with $R^{\circ}$; $-NO_2$; $-CN$; $-N_3$; $-(CH_2)_{0-4}N(R^{\circ})_2$; $-(CH_2)_{0-4}N(R^{\circ})C(O)R^{\circ}$; $-N(R^{\circ})C(S)R^{\circ}$; $-(CH_2)_{0-4}N(R^{\circ})C(O)NR^{\circ}_2$; $-N(R^{\circ})C(S)NR^{\circ}_2$; $-(CH_2)_{0-4}N(R^{\circ})C(O)OR^{\circ}$; $-N(R^{\circ})N(R^{\circ})C(O)R^{\circ}$; $-N(R^{\circ})N(R^{\circ})C(O)NR^{\circ}_2$; $-N(R^{\circ})N(R^{\circ})C(O)OR^{\circ}$; $-(CH_2)_{0-4}C(O)R^{\circ}$; $-C(S)R^{\circ}$; $-(CH_2)_{0-4}C(O)OR^{\circ}$; $-(CH_2)_{0-4}C(O)SR^{\circ}$; $-(CH_2)_{0-4}C(O)OSiR^{\circ}_3$; $-(CH_2)_{0-4}OC(O)R^{\circ}$; $-OC(O)(CH_2)_{0-4}SR-$, $SC(S)SR^{\circ}$; $-(CH_2)_{0-4}SC(O)R^{\circ}$; $-(CH_2)_{0-4}C(O)NR^{\circ}_2$; $-C(S)NR^{\circ}_2$; $-C(S)SR^{\circ}$; $-SC(S)SR^{\circ}$, $-(CH_2)_{0-4}OC(O)NR^{\circ}_2$; $-C(O)N(OR^{\circ})R^{\circ}$; $-C(O)C(O)R^{\circ}$; $-C(O)CH_2C(O)R^{\circ}$; $-C(NOR^{\circ})R^{\circ}$; $-(CH_2)_{0-4}SSR^{\circ}$; $-(CH_2)_{0-4}S(O)_2R^{\circ}$; $-(CH_2)_{0-4}S(O)_2OR^{\circ}$; $-(CH_2)_{0-4}OS(O)_2R^{\circ}$; $-S(O)_2NR^{\circ}_2$; $-(CH_2)_{0-4}S(O)R^{\circ}$; $-N(R^{\circ})S(O)_2NR^{\circ}_2$; $-N(R^{\circ})S(O)_2R^{\circ}$; $-N(OR^{\circ})R^{\circ}$; $-C(NH)NR^{\circ}_2$; $-P(O)_2R^{\circ}$; $-P(O)R^{\circ}_2$; $-OP(O)R^{\circ}_2$; $-OP(O)(OR^{\circ})_2$; $SiR^{\circ}_3$; $-(C_{1-4}$ straight or branched alkylene)$O-N(R^{\circ})_2$; or $-(C_{1-4}$ straight or branched alkylene)$C(O)O-N(R^{\circ})_2$, wherein each $R^{\circ}$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), is independently halogen, $-(CH_2)_{0-2}R^{\bullet}$, -(halo$R^{\bullet}$), $-(CH_2)_{0-2}OH$, $-(CH_2)_{0-2}OR^{\bullet}$, $-(CH_2)_{0-2}CH(OR^{\bullet})_2$; $-O$(halo$R^{\bullet}$), $-CN$, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-OSiR^{\bullet}_3$, $-C(O)SR^{\bullet}$, $-(C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\circ}$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^{\bullet}$, -(halo$R^{\bullet}$), $-OH$, $-OR^{\bullet}$, $-O$(halo$R^{\bullet}$), $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^{\dagger}$, $-NR^{\dagger}_2$, $-C(O)R^{\dagger}$, $-C(O)OR^{\dagger}$, $-C(O)C(O)R^{\dagger}$, $-C(O)CH_2C(O)R^{\dagger}$, $-S(O)_2R^{\dagger}$, $-S(O)_2NR^{\dagger}_2$, $-C(S)NR^{\dagger}_2$, $-C(NH)NR^{\dagger}_2$, or $-N(R^{\dagger})S(O)_2R^{\dagger}$; wherein each $R^{\dagger}$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ is independently halogen, —$R^{\bullet}$, -(halo$R^{\bullet}$), —OH, —$OR^{\bullet}$, —O(halo$R^{\bullet}$), —CN, —C(O)OH, —C(O)$OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

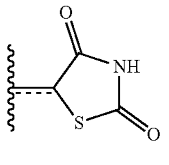

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and 1 or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

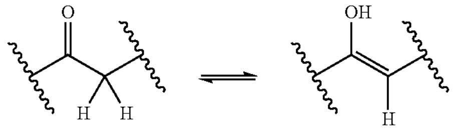

keto form enol form

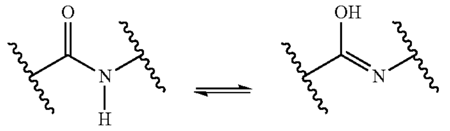

amide form imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

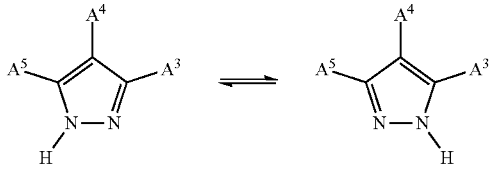

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

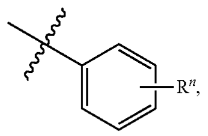

which is understood to be equivalent to a formula:

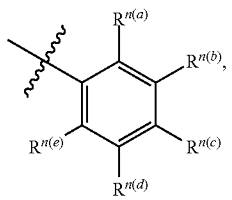

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C—F are considered disclosed. Likewise, any subset or combination of these is also disclosed. Thus, for example, the sub-group of A-E, B—F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. ARENE C—H FUNCTIONALIZATION

As nitrogen-containing aromatic compounds are highly prevalent in pharmaceuticals and natural products, the development of facile routes towards the synthesis of anilines and other nitrogen-containing heterocycles is highly sought after. Anilines are traditionally synthesized via arene nitration followed by hydrogenation or metal catalyzed reduction (Belfield et al. (1999) *Tetrahedron* 55, 11399). Nitration reactions, however, require strongly oxidizing, acidic conditions, which can limit the scope of the reaction due to a lack of functional group tolerance.

In order to overcome these shortcomings, cross-coupling reactions involving metal catalysts, generally palladium or copper-based catalysts, to couple amines with aryl halides or triflates were developed (e.g., Buchwald-Hartwig amination). Despite advancements in ligand design and amine nucleophile tolerance, cross-coupling systems continue to suffer from several limitations. For example, highly inert, anhydrous conditions are required to prevent catalyst decomposition. Additionally, arenes require prefunctionalization as a halide or a triflate (Surry et al. (2011) *Chem. Sci.* 2, 27; Hartwig, J. F. (2008) *Acc. Chem. Res.* 41, 1534). Finally, cross-coupling approaches are generally limited by steric hindrance such that amination ortho to another functional group can be very challenging, resulting in lower yields, as in the ortho-methoxy derivative.

To circumvent the requirement of prefunctionalized arenes, more recent work has demonstrated the utility of arene C—H functionalization as an alternative strategy for the construction of these aryl amines. Current methodologies are limited by several factors, including regioselectivity, necessity of superstoichiometric quantities of reagents, and, in many cases, non-atom economical oxidants.

The regiochemical outcome of a transition metal-catalyzed arene C—H functionalization is generally dictated by reliance on a preinstalled Lewis basic directing group (Matsubara et al. (2014) *J. Am. Chem. Soc.* 136, 646), which results in predominantly ortho-selectivity with respect to that functionality. Buchwald, in 2005, developed an intramolecular arene C—H amination reaction to form carbazoles from 2-acetaminobiphenyl derivatives (Tsang et al. (2005) *J. Am. Chem. Soc.* 127, 14560). A palladium catalyst was used along with a stoichiometric amount of a copper co-oxidant under aerobic conditions. The amide directed ortho-palladation would form the proposed metallocycle, which would undergo reductive elimination of the desired carbazole. Other groups have looked to utilize oxidants such as diacetoxyiodobenzene for intramolecular C—H aminations towards carbazoles (Antonchick et al. (2011) *Angew. Chem. Int. Ed.* 50, 8605). Methods in which the directing group can be removed following the amination have been reported, widening the scope of amination products that can be accessed (Tran et al. (2013) *Angew. Chem. Int. Ed.* 52, 6043).

Intermolecular arene C—H amination reactions have also been developed, many of which are metal-catalyzed and require directing groups to form ortho regioisomers. Shen, in 2010, developed an aerobic copper-mediated aryl amination reaction (Xu et al. (2014) *J. Org. Chem.* 79, 4414), in which use of a pyridine or pyrimidine directing group facilitated the addition of phthalimide nucleophiles to arenes with oxygen as a terminal oxidant.

While ortho-selectivity is prevalent, some examples of meta-selective arene amination reactions have also been reported. Hartwig recently demonstrated a sterically controlled intermolecular arene amination (Shrestha et al. (2013) J. Am. Chem. Soc. 135, 8480), using phthalimide as a nucleophile along with diacetoxyiodobenzene as a superstoichiometric terminal oxidant. While many reactions favored meta-functionalization, selectivity over para-functionalization was generally low. These reactions also required that the arene coupling partner was the solvent.

In 2011, DeBeof reported a metal-free intermolecular oxidative dual C—H and N—H bond functionalization reaction (Kantak et al. (2011) *J. Am. Chem. Soc.* 133, 1960). It was demonstrated that amide derivatives could add to various arenes; however, significant excesses of arene were required, in some cases even as solvent, to observe the desired reactivity. Diacetoxyiodobenzene was used as a superstoichiometric oxidant, and microwave irradiation could furnish the functionalized products. The authors proposed that the iodine reagent oxidizes the arene to the aryl radical cation, allowing for addition to the more electrophilic ortho- or para-positions on the arene intermediate. This was supported by the observed functionalization occurring at the ortho- and para-positions in roughly 1:1 ratios; however, minor amounts of meta-functionalized product were observed but never as the major isomer. DeBeof later demonstrated the use of a gold catalyst along with diacetoxyiodobenzene as the oxidant to selectively form para-functionalized products (Marchetti et al. (2015) *Org. Lett.* 17, 258). While this system improved upon previous regioselectivity, it required the arene to be used as the solvent, limiting potential applicability.

In 2014, Sanford developed a visible light photocatalyzed, $[Ir(ppy)_3]$ mediated system in which N-acyloxyphthalimide could form nitrogen centered radicals and subsequently add to arenes and heteroarenes (Allen et al. (2014) *J. Am. Chem. Soc.* 136, 5607). Many of the substrates were ortho-functionalized; however, Sanford was able to demonstrate meta-selectivity with pyridine derivatives. It is believed that visible light excites the iridium catalyst, which induces a SET process, cleaving the N—O bond of the acyloxyphthalimide to generate a nitrogen centered radical that can add to the arene. While no additional oxidants were required for this system, the authors reported using 10 equivalents of the arene as well as a prefunctionalized phthalimide.

Use of electrooxidative conditions to facilitate arene coupling can be effective but also problematic due to undesirable oxidation of functional groups in the substrates. Yoshida demonstrated the use of protected imidazoles in an electrooxidative coupling with both aromatic and benzylic electrophiles (Morofuji et al. (2014) J Am. Chem. Soc. 136, 4496). Protection of the imidazole or benzimidazole nucleophile prevented overoxidation of the imidazole products, which are susceptibile to electrochemical oxidation; however, treatment with base after the reaction was required to cleave the mesylate group.

To date, many ortho-selective aryl amination reactions have been developed; however, some meta-selective examples have also been reported. Furthermore, use of stoichiometric oxidants results in poor atom economy, demonstrating how use of molecular oxygen as an oxidant can be appealing in terms of minimizing waste. Excess arene (Brachet et al. (2014) *Advance Article*; Prier et al. (2013) *Chem. Rev.* 113, 5322), even in the form of the reaction solvent, often required to achieve synthetically useful yields, limiting applicability to easily attainable substrates.

Herein, an oxidative method of arene functionalization in which nucleophiles including, but not limited to, amines and halides can be added to arenes using an organic catalyst, i.e., an acridinium photocatalyst, where dioxygen ($O_2$) is the terminal oxidant is disclosed. This strategy constitutes a facile synthesis of para-substituted anilines via an arene C—H functionalization. It has been observed that a persistent radical additive or a precursor to an in situ generated persistent radical may improve chemical yields; however, addition of such an exogenous additive is not required under modified conditions. Unlike previous examples of direct aryl amination reported in the literature, this method does not stipulate a significant excess of either arene or amine. Anilines may be synthesized directly via addition of ammonia in the form of simple ammonium salts. Additionally, chlorinated and fluorinated arenes were detected when halide salts were employed, indicating that arene functionalization is feasible through this method with other classes of nucleophiles. This method does not rely on a Lewis basic substituent for regiochemical differentiation; thus, a greater variety of arene substitution patterns can be accessed. Lastly, the use of dioxygen as a reagent and an organic photocatalyst is an attractive alternative to the more expensive and environmentally noxious oxidants and transition metals employed in other methodologies.

C. PHOTOREDOX CHEMISTRY

Given that many organic compounds do not absorb in the visible region of the electromagnetic spectrum, various reactions have been developed that instead use ultraviolet light, which these molecules can absorb. To harness visible light instead, metal complexes such as $[Ru(byp)_3]^{2+}$ and $[Ir(ppy)_3]$ (Pirer et al. (2013) *Chem. Rev.* 113, 5322) and organic dyes such as methylene blue and eosin Y (Nicewicz and Nguyen (2014) *ACS Catal.* 4, 355), have been examined.

When looking to employ oxidative photoredox chemistry, identifying an appropriate catalyst can be challenging. For example, photocatalysts such as $[Ru(byp)_3]^{2+}$ ($E_{1/2}^{red*}$=+0.77 V vs. SCE) are capable of oxidizing electron-rich alkenes but not aliphatic alkenes. Similarly, eosin Y ($E_{1/}$ $_2{}^{red*}$=+0.79 V vs. SCE) is able to oxidize compounds in the same range. While ligand modification on various metal photocatalysts can facilitate oxidation of less oxidizable substrates, such derivatives generally do not possess oxidation potentials high enough to react with disubstituted alkenes.

The use of Fukuzumi's catalyst (Mes-Acr-$MeBF_4$) in anti-Markovnikov hydroetherification (Hamilton and Nicewicz (2012) *J. Am. Chem. Soc.* 134, 18577), hydroamination (Nguyen and Nicewicz (2013) *J. Am. Chem. Soc.* 135, 9588), and hydroacetoxylation (Perkowshi and Nicewicz (2013) *J. Am. Chem. Soc.* 135, 10334) has been previously demonstrated. In the intermolecular hydroamination reactions, several amides, sulfonimides, and nitrogen-containing heterocycles such as pyrazoles and triazoles, were used to functionalize alkenes (Nguyen et al. (2014) *Angew. Chem. Int. Ed.* 53, 6198). It has been theorized that after excitation by visible light (450 nm LEDs), Fukuzumi's catalyst can undergo single electron transfer (SET) from the olefin, generating a radical cation. Subsequent nucleophilic addition and H-atom donation affords the anti-Markovnikov adduct. This regioselective functionalization arises from the formation of the more stable benzylic radical.

In addition to alkenes, the mesityl acridinium catalyst has also been shown to oxidize sufficiently electron-rich arenes (Ohkuba et al. (2011) *Chem. Sci.* 2, 715). Here, the bromination of various electron-rich arenes using Fukuzumi's catalyst and hydrobromic acid under aerobic conditions was reported. Several methoxy-substituted arenes produced the desired bromination product in high yields in as little as 20 minutes, although some less electron-rich arenes required up to 16 hours for quantitative conversion. For methyl-substituted arenes, conversion of the starting material was still quantitative; however, the yields were significantly lower due to competing benzylic oxidation. It was proposed that the photocatalyst is excited, which can oxidize an electron-rich arene to a radical cation. Bromine addition followed by oxidation affords the corresponding arene derivative. This research was later extended to chlorination reactions with a similar aerobic system (Ohkubu et al. (2013) *Res. Chem. Intermed.* 39, 205). Highly oxidizable arenes such as trimethoxybenzenes furnished the chlorinated products; however, they were obtained in low yields (generally less than 25%).

D. SUBSTITUTED ARENES

In one aspect, substituted arenes are disclosed. In a further aspect, the arene ispara-substituted. In a still further aspect, the arene is ortho-substituted. In yet a further aspect, the arene is both para- and ortho-substituted.

It is contemplated that each disclosed derivative can be optionally further substituted. It is also contemplated that any one or more derivative can be optionally omitted from the invention. It is understood that a disclosed compound can be provided by the disclosed methods.

1. Structure

In one aspect, disclosed are compounds having a structure represented by a formula:

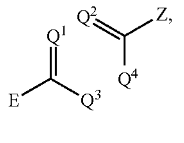

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; or wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; wherein Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —$NNR^4$, —OC(═O)$R^5$, and $Ar^1$; wherein $R^4$ is selected from hydrogen and C1-C8 alkyl; wherein $R^5$ is selected from C1-C8 alkyl; and wherein $Ar^1$ is a 3- to 6-membered heterocycle substituted with 0, 1, 2, or 3 groups independently selected from halogen and C1-C8 alkyl. In a further aspect, the electron donating group is selected from —OH, —SH, —$NH_2$, C1-C8 alkyl, C1-C8 alkoxy, C1-C8 thioalkoxy, C1-C8 silyloxy, C1-C8 alkylamino, (C1-C8)(C1-C8) dialkylamino, —OC(═O)$R^6$, —NHC(═O)$R^7$, —$OAr^2$, and $Ar^2$; wherein each of $R^6$ and $R^7$ is independently selected from C1-C8 alkyl; and wherein $Ar^2$ is selected from aryl and heteroaryl and substituted with 0, 1, 2, or 3 groups independently selected from halogen and C1-C8 alkyl. In a still further aspect, the electron donating group is selected from —OH, —SH, —$NH_2$, C1-C8 alkyl, C1-C8 alkoxy, C1-C8 thioalkoxy, C1-C8 alkylamino, (C1-C8)(C1-C8) dialkylamino, —OC(═O)$R^6$, —NHC(═O)$R^7$, and $Ar^2$; wherein each of $R^6$ and $R^7$ is independently selected from C1-C8 alkyl; and wherein $Ar^2$ is selected from aryl and heteroaryl and substituted with 0, 1, 2, or 3 groups independently selected from halogen and C1-C8 alkyl.

In one aspect, disclosed are compounds having a structure represented by a formula:

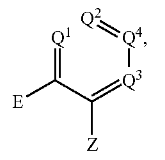

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; or wherein each of $Q^2$ and $Q^4$ is $CR^2$ and wherein each occurrence of $R^2$ are optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and —C(═O)$NR^{3a}R^{3b}$; wherein Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —$NNR^4$, —OC(═O)$R^5$, and $Ar^1$; wherein $R^4$ is selected from hydrogen and C1-C8 alkyl; wherein $R^5$ is selected from C1-C8 alkyl; and wherein $Ar^1$ is a 3- to 6-membered heterocycle substituted with 0, 1, 2, or 3 groups independently selected from halogen and C1-C8 alkyl. In a further aspect, the electron donating group is selected from —OH, —SH, —$NH_2$, C1-C8 alkyl, C1-C8 alkoxy, C1-C8 thioalkoxy, C1-C8 silyloxy, C1-C8 alkylamino, (C1-C8)(C1-C8) dialkylamino, —OC(═O)$R^6$, —NHC(═O)$R^7$, —$OAr^2$, and $Ar^2$; wherein each of $R^6$ and $R^7$ is independently selected from C1-C8 alkyl; and wherein $Ar^2$ is selected from aryl and heteroaryl and substituted with 0, 1, 2, or 3 groups independently selected from halogen and C1-C8 alkyl. In a still further aspect, the electron donating group is selected from —OH, —SH, —$NH_2$, C1-C8 alkyl, C1-C8 alkoxy, C1-C8 thioalkoxy, C1-C8 alkylamino, (C1-C8)(C1-C8) dialkylamino, —OC(═O)$R^6$, —NHC(═O)$R^7$, and $Ar^2$; wherein each of $R^6$ and $R^7$ is independently selected from C1-C8 alkyl; and wherein $Ar^2$ is selected from aryl and heteroaryl and substituted with 0, 1, 2, or 3 groups independently selected from halogen and C1-C8 alkyl.

In one aspect, disclosed are compounds having a structure represented by a formula:

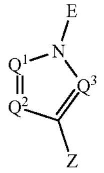

or

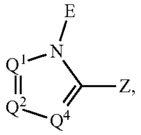

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; or wherein $R^1$ and $R^2$ are optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; wherein Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —$NNR^4$, —OC(═O)$R^5$, and $Ar^1$; wherein $R^4$ is selected from hydrogen and C1-C8 alkyl; wherein $R^5$ is selected from C1-C8 alkyl; and wherein $Ar^1$ is a 3- to 6-membered heterocycle substituted with 0, 1, 2, or 3 groups independently selected from halogen and C1-C8 alkyl. In a further aspect, the electron donating group is selected from —OH, —SH, —$NH_2$, C1-C8 alkyl, C1-C8 alkoxy, C1-C8 thioalkoxy, C1-C8 silyloxy, C1-C8 alkylamino, (C1-C8)(C1-C8) dialkylamino, —OC(═O)$R^6$, —NHC(═O)$R^7$, —$OAr^2$, and $Ar^2$; wherein each of $R^6$ and $R^7$ is independently selected from C1-C8 alkyl; and wherein $Ar^2$ is selected from aryl and heteroaryl and substituted with 0, 1, 2, or 3 groups independently selected from halogen and C1-C8 alkyl. In a still further aspect, the electron donating group is selected from —OH, —SH, —$NH_2$, C1-C8 alkyl, C1-C8 alkoxy, C1-C8 thioalkoxy, C1-C8 alkylamino, (C1-

C8)(C1-C8) dialkylamino, —OC(═O)$R^6$, —NHC(═O)$R^7$, and $Ar^2$; wherein each of $R^6$ and $R^7$ is independently selected from C1-C8 alkyl; and wherein $Ar^2$ is selected from aryl and heteroaryl and substituted with 0, 1, 2, or 3 groups independently selected from halogen and C1-C8 alkyl.

In a further aspect, a compound has a structure represented by a formula selected from:

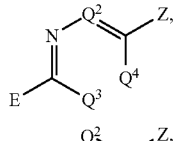 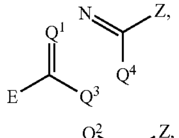

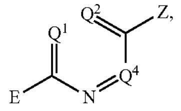 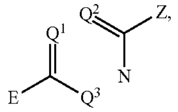

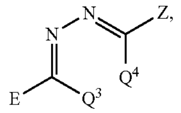 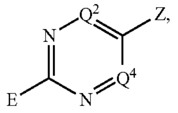

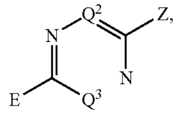 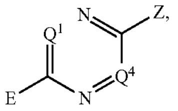

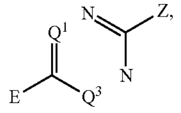 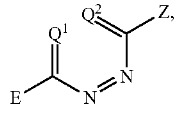

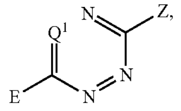 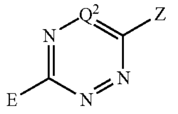

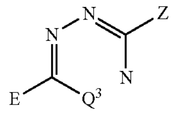 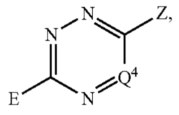 and

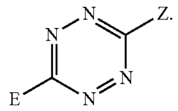

In a further aspect, a compound has a structure represented by a formula selected from:

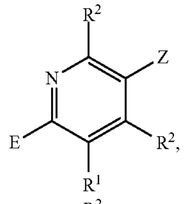 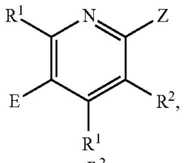

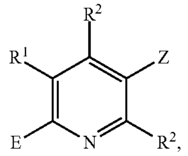 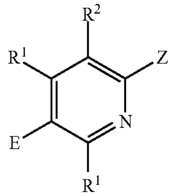 ,

-continued
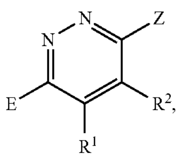 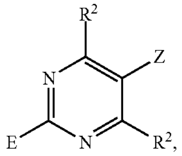
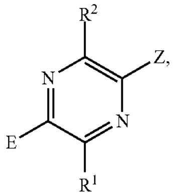 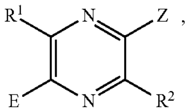
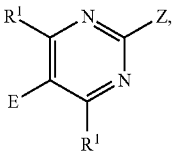 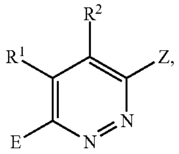
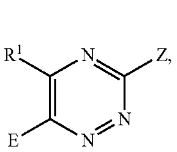 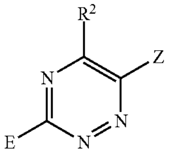
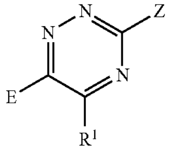 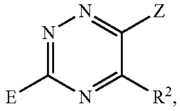 and
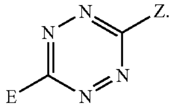
In a further aspect, a compound has a structure represented by a formula selected from:
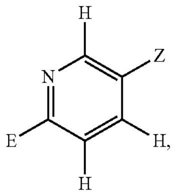 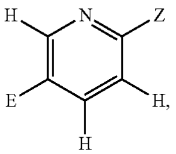
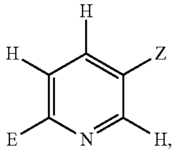 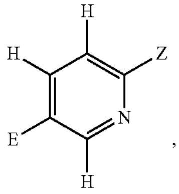 ,
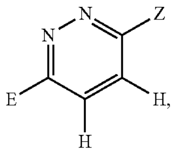 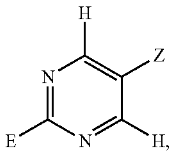
-continued
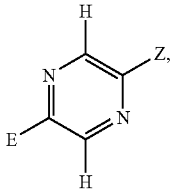 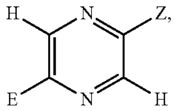
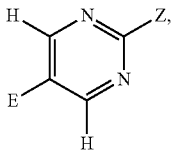 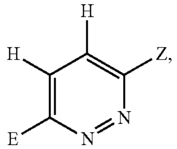
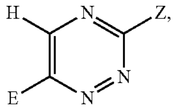 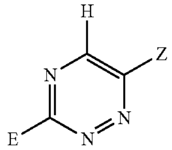
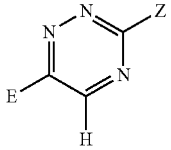 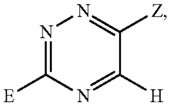 and
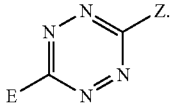
In a further aspect, a compound has a structure represented by a formula:
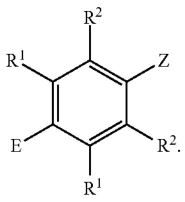
In a further aspect, a compound has a structure represented by a formula selected from:
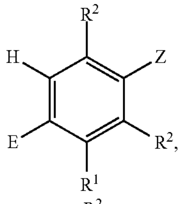 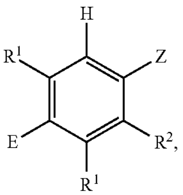
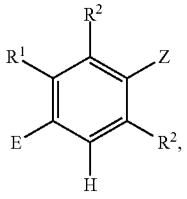 and 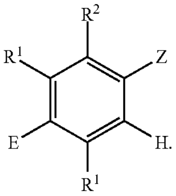
In a further aspect, a compound has a structure represented by a formula:

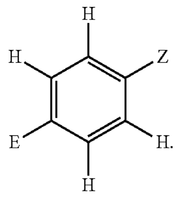

In a further aspect, a compound has a structure represented by a formula selected from:

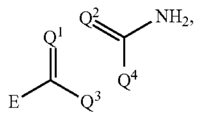
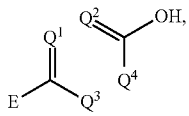
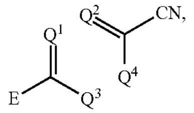
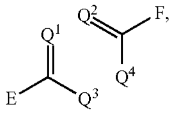
and
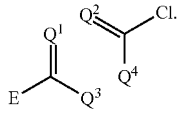

In a further aspect, a compound has a structure represented by a formula selected from:

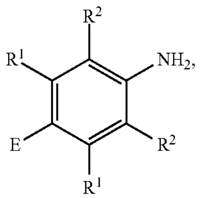
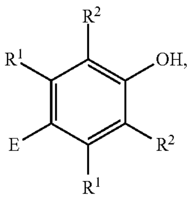
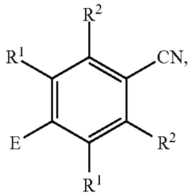
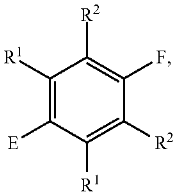
and
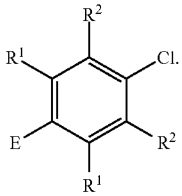

In a further aspect, a compound has a structure represented by a formula selected from:

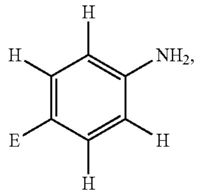
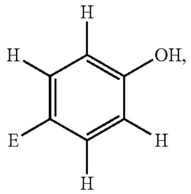

-continued

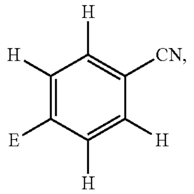
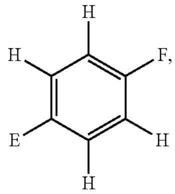
and
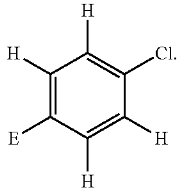

In a further aspect, a compound has a structure represented by a formula:

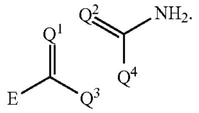

In a further aspect, a compound has a structure represented by a formula:

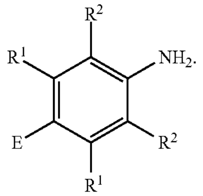

In a further aspect, a compound has a structure represented by a formula selected from:

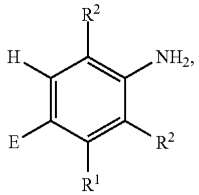
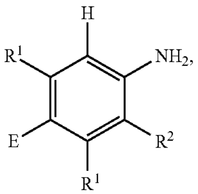
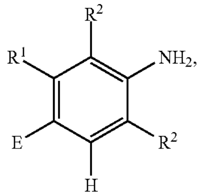
and
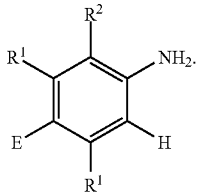

In a further aspect, a compound has a structure represented by a formula:

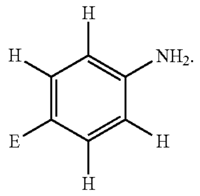

In a further aspect, a compound has a structure represented by a formula:

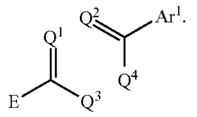

In a further aspect, a compound has a structure represented by a formula selected from:

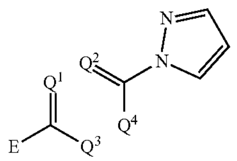

and

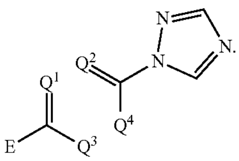

In a further aspect, a compound has a structure represented by a formula:

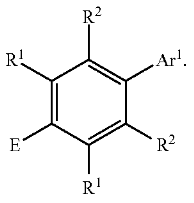

In a further aspect, a compound has a structure represented by a formula selected from:

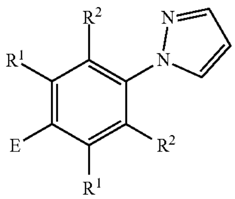

and

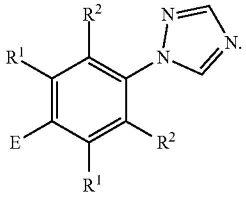

In a further aspect, a compound has a structure represented by a formula:

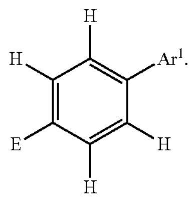

In a further aspect, a compound has a structure represented by a formula selected from:

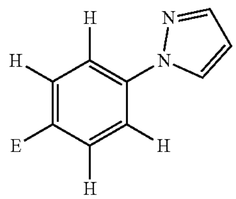

and

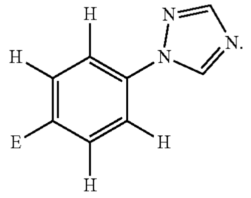

In a further aspect, a compound has a structure represented by a formula:

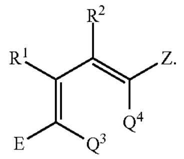

In a further aspect, a compound has a structure represented by a formula:

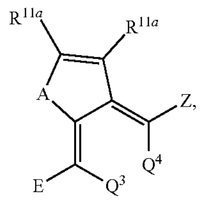

wherein A is selected from $CR^{12a}R^{12b}$, O, S, and $NR^{13}$; wherein each of $R^{12a}$, $R^{12b}$, and $R^{13}$, when present, is independently selected from hydrogen and C1-C4 alkyl; and wherein each of $R^{11a}$ and $R^{11b}$ is independently selected from hydrogen and C1-C4 alkyl.

In a further aspect, a compound has a structure represented by a formula selected from:

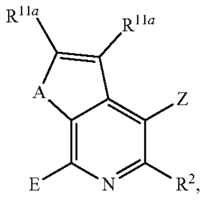

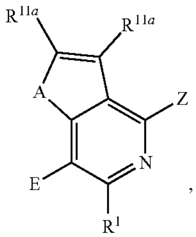

,

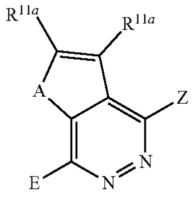

, and

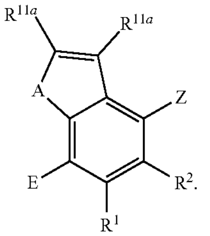

In a further aspect, a compound has a structure represented by a formula:

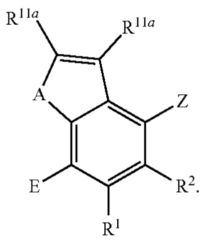

In a further aspect, a compound has a structure represented by a formula:

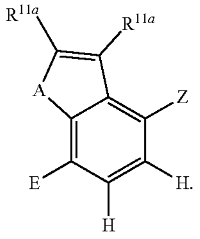

In a further aspect, a compound has a structure represented by a formula:

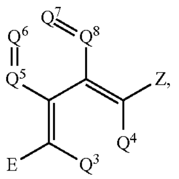

wherein each of $Q^5$, $Q^6$, $Q^7$, and $Q^8$ is independently selected from N and $CR^{14}$; and wherein each occurrence of $R^{14}$ is independently selected from hydrogen, halogen, C1-C8 alkyl, C1-C8 alkoxy, and $—C(=O)NR^{3a}R^{3b}$.

In a further aspect, a compound has a structure represented by a formula selected from:

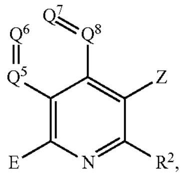

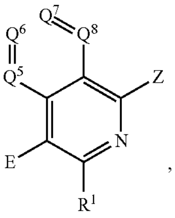

,

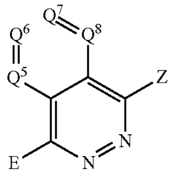

, and

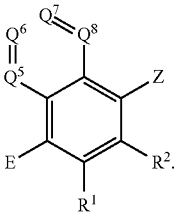

In a further aspect, a compound has a structure represented by a formula:

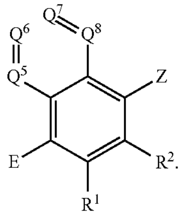

In a further aspect, a compound has a structure represented by a formula:

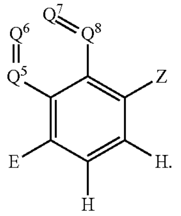

In a further aspect, a compound has a structure represented by a formula selected from:

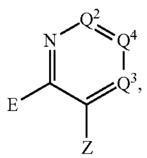

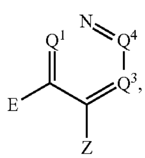

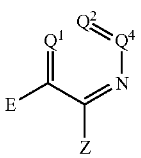

,

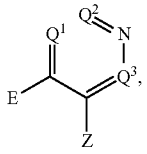

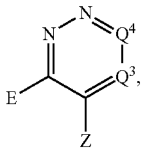

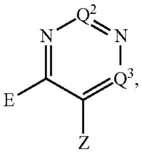

-continued
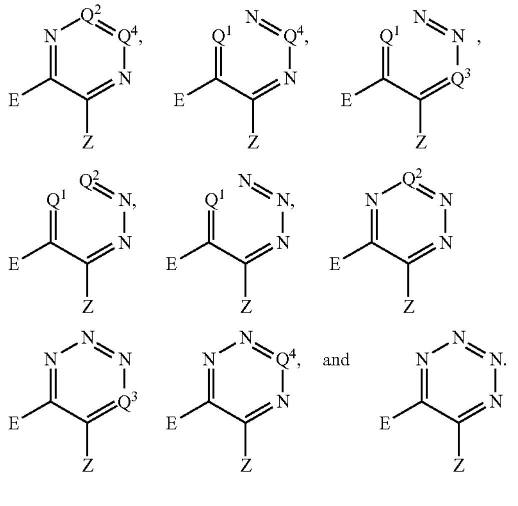
and
In a further aspect, a compound has a structure represented by a formula selected from:
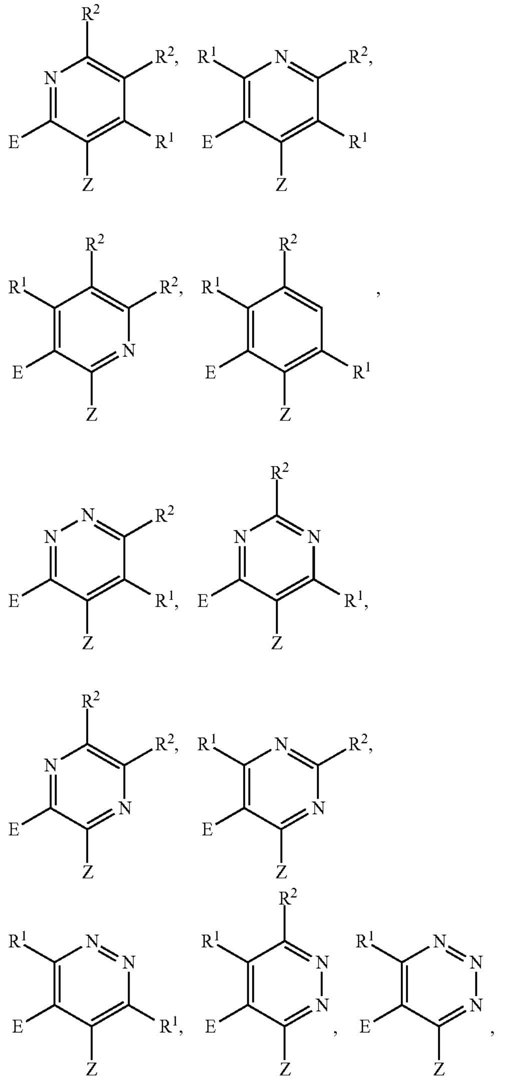
-continued
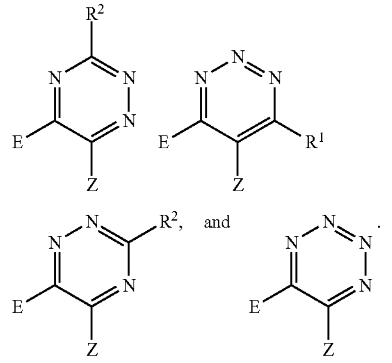
and
In a further aspect, a compound has a structure represented by a formula selected from:
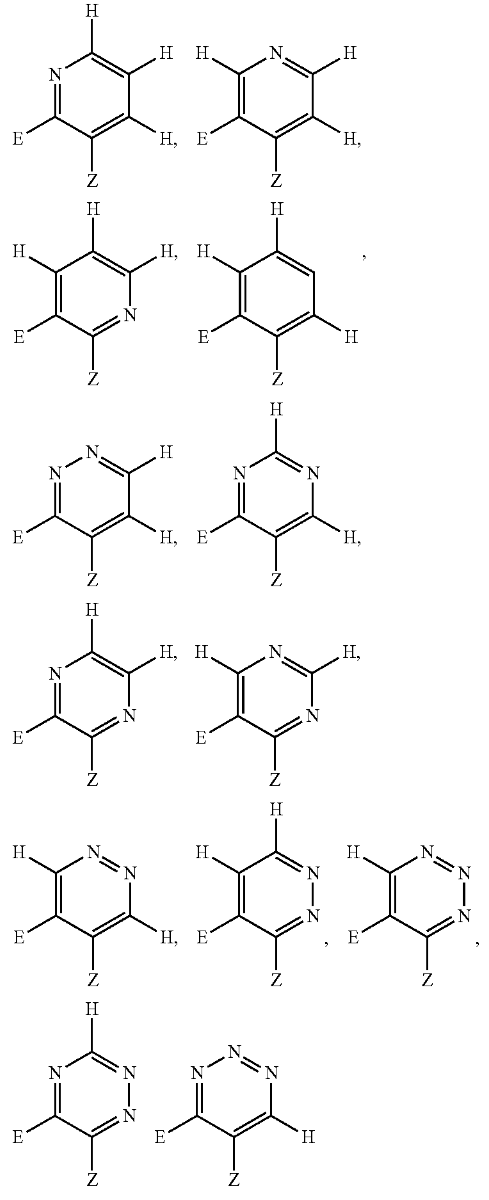

-continued

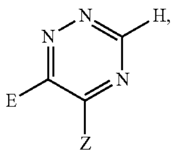

and

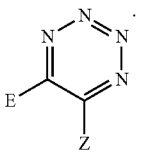

In a further aspect, a compound has a structure represented by a formula:

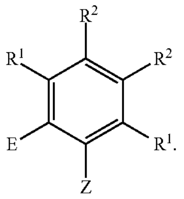

In a further aspect, a compound has a structure represented by a formula selected from:

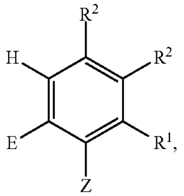

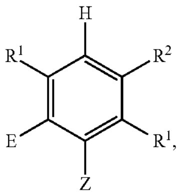

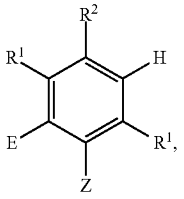

and

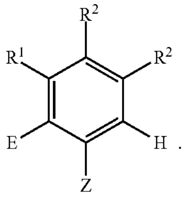

In a further aspect, a compound has a structure represented by a formula:

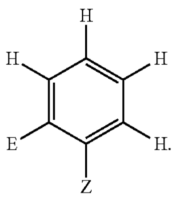

In a further aspect, a compound has a structure represented by a formula selected from:

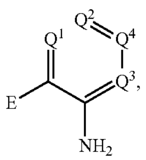

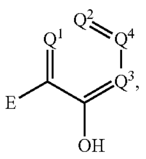

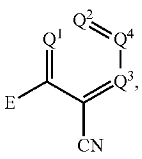

-continued

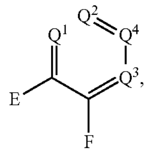

and

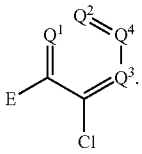

In a further aspect, a compound has a structure represented by a formula selected from:

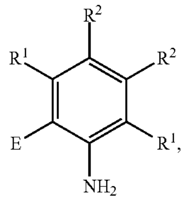

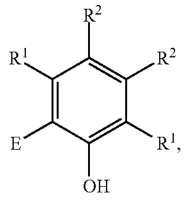

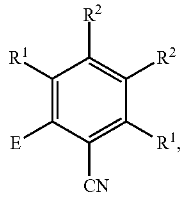

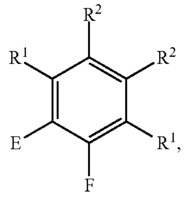

and

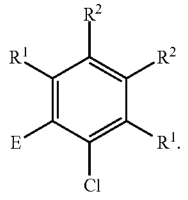

In a further aspect, a compound has a structure represented by a formula selected from:

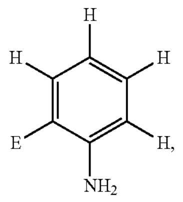

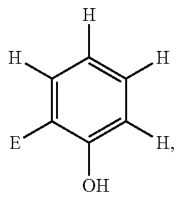

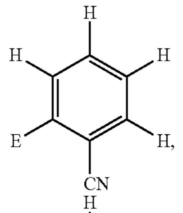

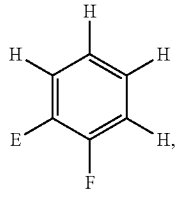

and

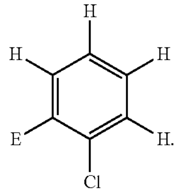

In a further aspect, a compound has a structure represented by a formula:

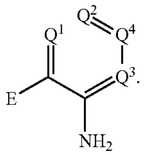

In a further aspect, a compound has a structure represented by a formula:

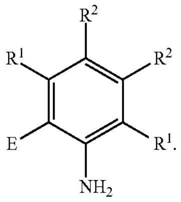

In a further aspect, a compound has a structure represented by a formula selected from:

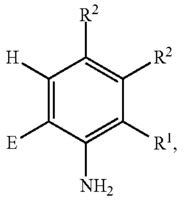

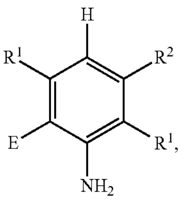

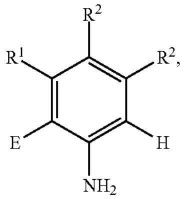

and

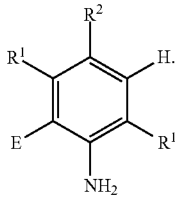

In a further aspect, a compound has a structure represented by a formula:

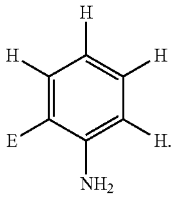

In a further aspect, a compound has a structure represented by a formula:

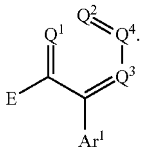

In a further aspect, a compound has a structure represented by a formula selected from:

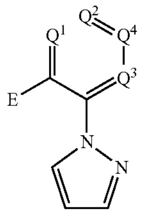

and

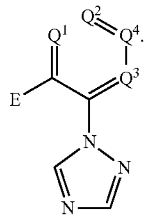

In a further aspect, a compound has a structure represented by a formula:

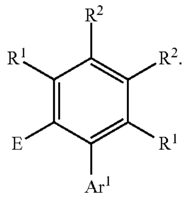

In a further aspect, a compound has a structure represented by a formula selected from:

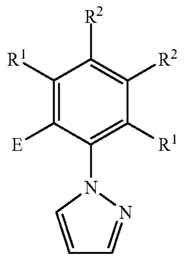

and

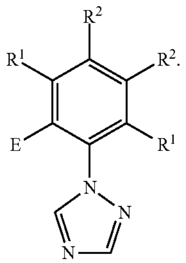

In a further aspect, a compound has a structure represented by a formula:

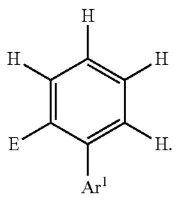

In a further aspect, a compound has a structure represented by a formula selected from:

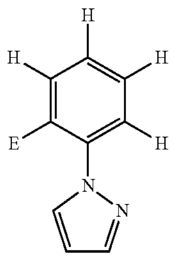

and

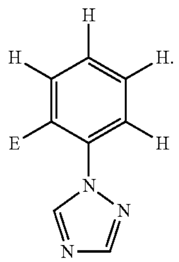

In a further aspect, a compound has a structure represented by a formula selected from:

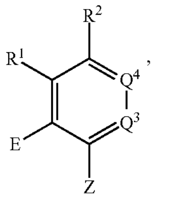

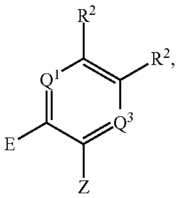

and

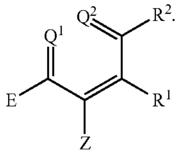

In a further aspect, a compound has a structure represented by a formula selected from:

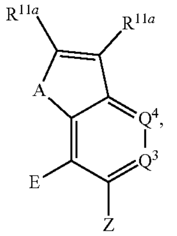

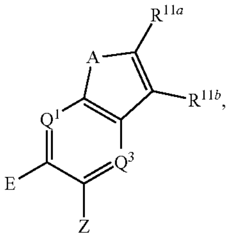

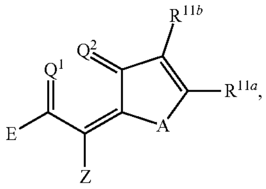

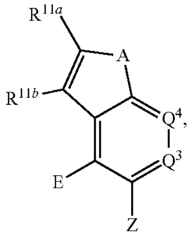

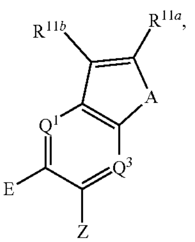

and

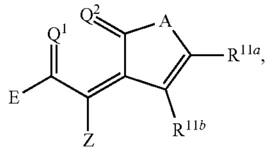

wherein A is selected from $CR^{12a}R^{12b}$, O, S, and $NR^{13}$; wherein each of $R^{12a}$, $R^{12b}$, and $R^{13}$, when present, is independently selected from hydrogen and C1-C4 alkyl; and wherein each of $R^{11a}$ and $R^{11b}$ is independently selected from hydrogen and C1-C4 alkyl.

In a further aspect, a compound has a structure represented by a formula selected from:

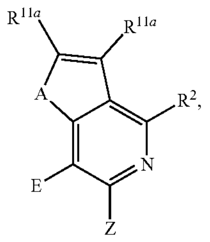

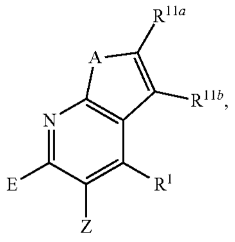

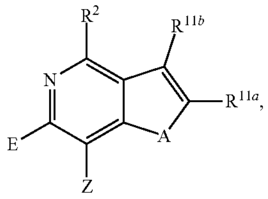

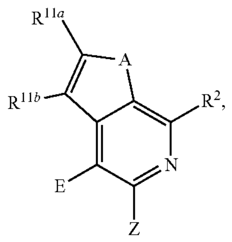

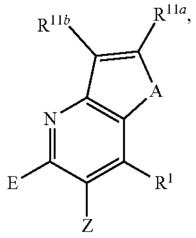

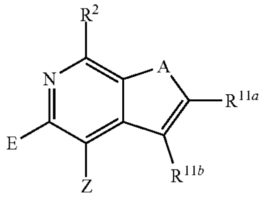

,

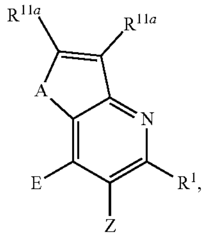

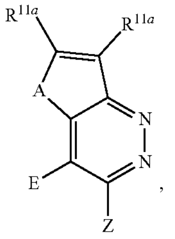

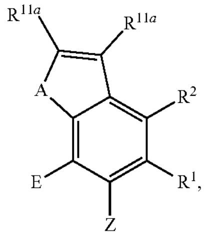

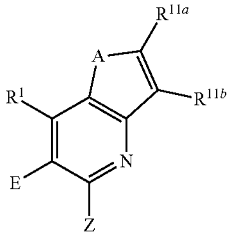

,

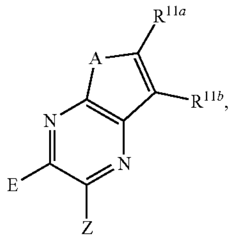

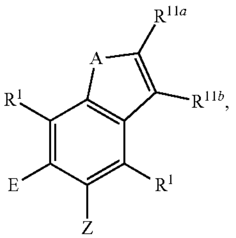

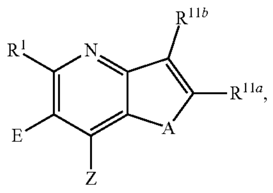

-continued
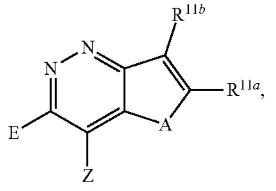
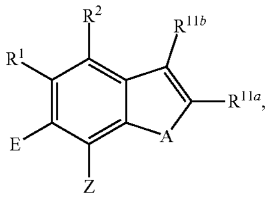
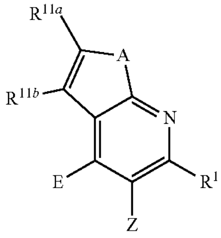
,
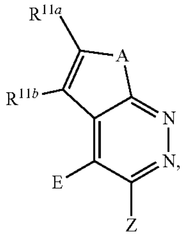
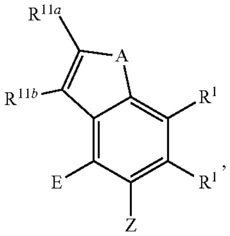
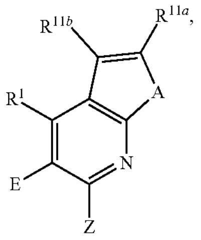
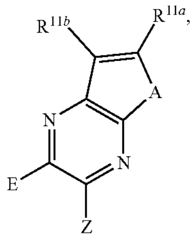
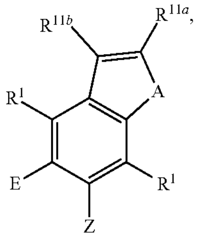
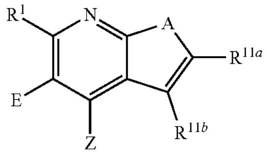
,
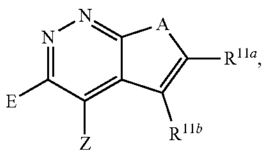
and
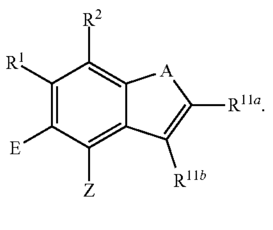
In a further aspect, a compound has a structure represented by a formula selected from:
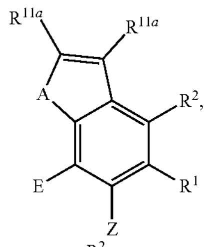
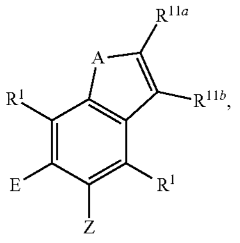
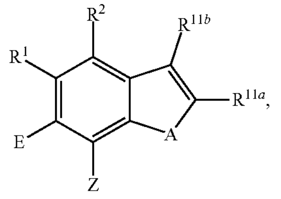
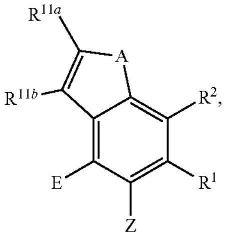
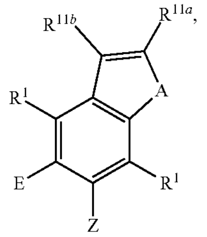
and
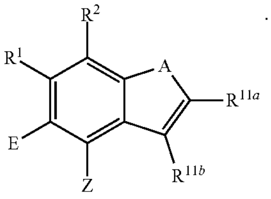
.
In a further aspect, a compound has a structure represented by a formula selected from:
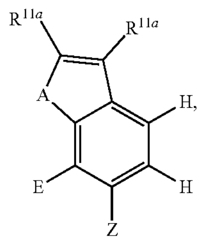
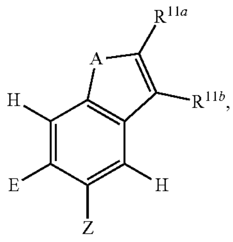
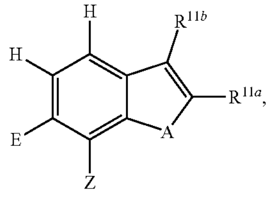
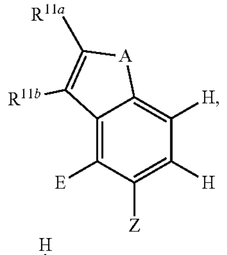
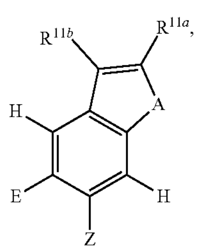
and
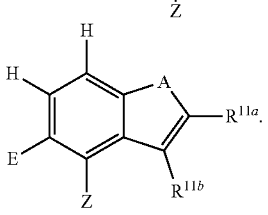
In a further aspect, a compound has a structure represented by a formula selected from:

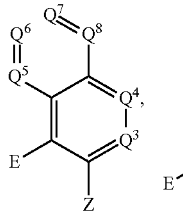
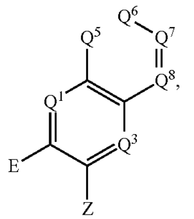
and
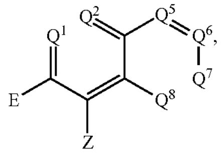

wherein each of $Q^5$, $Q^6$, $Q^7$, and $Q^8$ is independently selected from N and $CR^{14}$; and wherein each occurrence of $R^{14}$ is independently selected from hydrogen, halogen, C1-C8 alkyl, C1-C8 alkoxy, and —C(═O)$NR^{3a}R^{3b}$.

In a further aspect, a compound has a structure represented by a formula selected from:

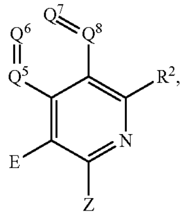
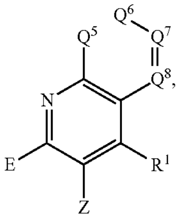
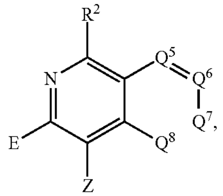
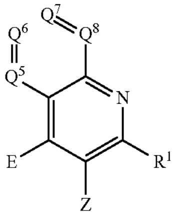
,
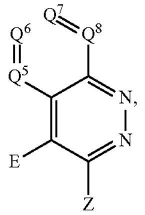
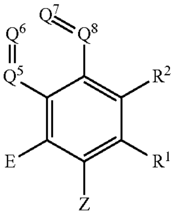
,
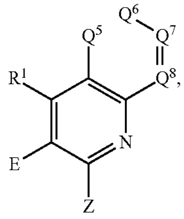
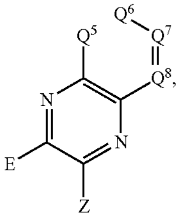
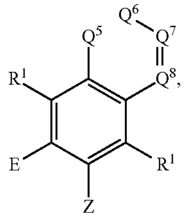
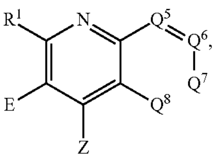

-continued

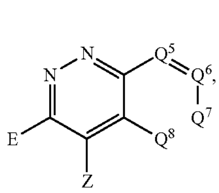
and
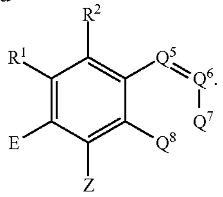

In a further aspect, a compound has a structure represented by a formula selected from:

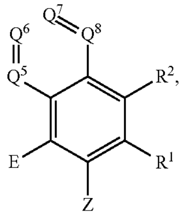
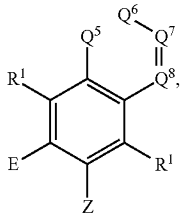
and
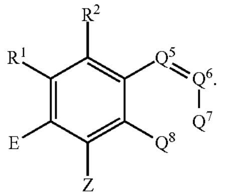

In a further aspect, a compound has a structure represented by a formula selected from:

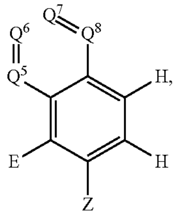
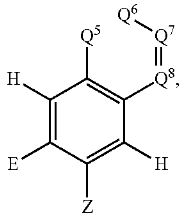
and
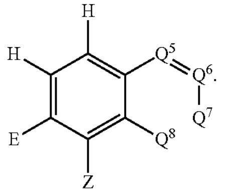

a. A Groups

In one aspect, A is selected from $CR^{12a}R^{12b}$, O, S, and $NR^{13}$. In a further aspect, A, when present, is selected from O, S, and $NR^{13}$. In a still further aspect, A is selected from S and $NR^{13}$. In yet a further aspect, A is selected from O and $NR^{13}$. In an even further aspect, A is $NR^{13}$. In a still further aspect, A is $CR^{12a}R^{12b}$. In yet a further aspect, A is O. In an even further aspect, A is S.

b. E Groups

In one aspect, E is an electron donating group. Exemplary electron donating groups are well known by those skilled in the art and include, but are not limited to, alkyl, alcohol, thioalcohol, alkoxy, thioalkoxy, silyloxy, amine, ester, amide, and aryl groups.

In a further aspect, the electron donating group is selected from —OH, —SH, —$NH_2$, C1-C8 alkyl, C1-C8 alkoxy, C1-C8 thioalkoxy, C1-C8 silyloxy, C1-C8 alkylamino, (C1-C8)(C1-C8) dialkylamino, —OC(═O)$R^6$, —NHC(═O)$R^7$, —O$Ar^2$, and $Ar^2$. In a still further aspect, the electron donating group is selected from —OH, —SH, —$NH_2$, C1-C8 alkyl, C1-C8 alkoxy, C1-C4 thioalkoxy, C1-C4 silyloxy, C1-C4 alkylamino, (C1-C4)(C1-C4) dialkylamino, —OC(═O)$R^6$, —NHC(═O)$R^7$, —O$Ar^2$, and $Ar^2$.

In a further aspect, the electron donating group is selected from —OH, —SH, —$NH_2$, C1-C8 alkyl, C1-C8 alkoxy, C1-C8 thioalkoxy, C1-C8 alkylamino, (C1-C8)(C1-C8) dialkylamino, —OC(═O)$R^6$, —NHC(═O)$R^7$, and $Ar^2$. In a still further aspect, the electron donating group is selected from —OH, —SH, —$NH_2$, C1-C8 alkyl, C1-C8 alkoxy, C1-C4 thioalkoxy, C1-C4 alkylamino, (C1-C4)(C1-C4) dialkylamino, —OC(═O)$R^6$, —NHC(═O)$R^7$, and $Ar^2$.

In a further aspect, the electron donating group is selected from —OH, —SH, —$NH_2$, C1-C8 alkyl, C1-C8 alkoxy, C1-C8 thioalkoxy, C1-C8 alkylamino, (C1-C8)(C1-C8) dialkylamino, —OC(═O)$R^6$, and —NHC(═O)$R^7$. In a still further aspect, the electron donating group is selected from —OH, —SH, —$NH_2$, C1-C8 alkyl, C1-C4 alkoxy, C1-C4 thioalkoxy, C1-C4 alkylamino, (C1-C4)(C1-C4) dialkylamino, —OC(═O)$R^6$, and —NHC(═O)$R^7$. In yet a further aspect, the electron donating group is selected from —OH, —SH, —$NH_2$, methyl, ethyl, n-propyl, iso-propyl, —$OCH_3$, —$OCH_2CH_3$, —$OCH_2CH_2CH_3$, —$OCH(CH_3)_2$, —$SCH_3$, —$SCH_2CH_3$, —$SCH_2CH_2CH_3$, —$SCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, —$N(CH(CH_3)_2)_2$, —OC(═O)$R^6$, and —NHC(═O)$R^7$. In an even further aspect, the electron donating group is selected from —OH, —SH, —$NH_2$, methyl, ethyl, —$OCH_3$, —$OCH_2CH_3$, —$SCH_3$, —$SCH_2CH_3$, —$NHCH_3$, —$NHCH_2CH_3$, —$N(CH_3)_2$, —$N(CH_3)(CH_2CH_3)$, —$N(CH_2CH_3)_2$, —OC(═O)$R^6$, and —NHC(═O)$R^7$. In a still further aspect, the electron donating group is selected from —OH, —SH, —$NH_2$, methyl, —$OCH_3$, —$SCH_3$, —$NHCH_3$, —$N(CH_3)_2$, —OC(═O)$R^6$, and —NHC(═O)$R^7$.

In a further aspect, the electron donating group is a C1-C8 silyloxy. In a still further aspect, the electron donating group is selected from trimethylsilyloxy, triisopropylsilyloxy, and tert-butyldimethylsilyloxy. In yet a further aspect, the electron donating group is selected from trimethylsilyloxy and triisopropylsilyloxy. In an even further aspect, the electron donating group is tert-butyldimethylsilyloxy. In a still further aspect, the electron donating group is triisopropylsilyloxy. In yet a further aspect, the electron donating group is trimethylsilyloxy.

In a further aspect, the electron donating group is selected from —OH, —SH, —$NH_2$, C1-C8 alkyl, C1-C8 alkoxy, C1-C8 thioalkoxy, C1-C8 alkylamino, and (C1-C8)(C1-C8) dialkylamino. In a still further aspect, the electron donating group is selected from —OH, —SH, —$NH_2$, C1-C8 alkyl, C1-C4 alkoxy, C1-C4 thioalkoxy, C1-C4 alkylamino, and (C1-C4)(C1-C4) dialkylamino. In yet a further aspect, the electron donating group is selected from —OH, —SH, —$NH_2$, methyl, ethyl, n-propyl, iso-propyl, —$OCH_3$, —$OCH_2CH_3$, —$OCH_2CH_2CH_3$, —$OCH(CH_3)_2$, —$SCH_3$, —$SCH_2CH_3$, —$SCH_2CH_2CH_3$, —$SCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In an even further aspect, the electron donating group is selected from —OH, —SH, —$NH_2$, methyl, ethyl, —$OCH_3$, —$OCH_2CH_3$, —$SCH_3$, —$SCH_2CH_3$, —$NHCH_3$, —$NHCH_2CH_3$, —$N(CH_3)_2$, —$N(CH_3)(CH_2CH_3)$, and —$N(CH_2CH_3)_2$. In a still further aspect, the electron donating group is selected from —OH, —SH, —$NH_2$, methyl, —$OCH_3$, —$SCH_3$, —$NHCH_3$, and —$N(CH_3)_2$.

In a further aspect, the electron donating group is selected from —OH, —SH, —$NH_2$, —OC(═O)$R^6$, —NHC(═O)$R^7$, —O$Ar^2$, and $Ar^2$. In a still further aspect, the electron donating group is selected from —OC(═O)$R^6$, —NHC(═O)$R^7$, —O$Ar^2$, and $Ar^2$. In yet a further aspect, the electron donating group is —O$Ar^2$.

In a further aspect, the electron donating group is selected from —OH, —SH, —$NH_2$, —OC(═O)$R^6$, —NHC(═O)$R^7$, and $Ar^2$. In a still further aspect, the electron donating group is selected from —OC(═O)$R^6$, —NHC(═O)$R^7$, and $Ar^2$. In yet a further aspect, the electron donating group is selected from —OC(═O)$R^6$ and —NHC(═O)$R^7$. In an even further aspect, the electron donating group is —OC(═O)$R^6$. In a still further aspect, the electron donating group is —NHC(═O)$R^7$. In yet a further aspect, the electron donating group is $Ar^2$.

In a further aspect, the electron donating group is selected from C1-C8 alkyl, C1-C8 alkoxy, C1-C8 thioalkoxy, C1-C8 alkylamino, and (C1-C8)(C1-C8) dialkylamino. In a still further aspect, the electron donating group is selected from C1-C8 alkyl, C1-C4 alkoxy, C1-C4 thioalkoxy, C1-C4 alkylamino, and (C1-C4)(C1-C4) dialkylamino. In yet a further aspect, the electron donating group is selected from methyl, ethyl, n-propyl, iso-propyl, —$OCH_3$, —$OCH_2CH_3$, —$OCH_2CH_2CH_3$, —$OCH(CH_3)_2$, —$SCH_3$, —$SCH_2CH_3$, —$SCH_2CH_2CH_3$, —$SCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In an even further aspect, the electron donating group is selected from methyl, ethyl, —$OCH_3$, —$OCH_2CH_3$, —$SCH_3$, —$SCH_2CH_3$, —$NHCH_3$, —$NHCH_2CH_3$, —$N(CH_3)_2$, —$N(CH_3)(CH_2CH_3)$, and —$N(CH_2CH_3)_2$. In a still further aspect, the electron donating group is selected from methyl, —$OCH_3$, —$SCH_3$, —$NHCH_3$, and —$N(CH_3)_2$.

In a further aspect, the electron donating group is selected from —OH, —SH, and —$NH_2$. In a still further aspect, the electron donating group is selected from —OH and —SH. In yet a further aspect, the electron donating group is selected from —OH and —$NH_2$. In an even further aspect, the electron donating group is selected from —SH and —$NH_2$. In a still further aspect, the electron donating group is —OH. In yet a further aspect, the electron donating group is —SH. In an even further aspect, the electron donating group is $NH_2$.

c. Z Groups

In one aspect, Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —NN$R^4$, —OC(═O)$R^5$, and $Ar^1$. In a further aspect, Z is selected from halogen, —CN, —$NH_2$, —OH, C1-C4 alkenyl, C1-C4 alkoxy, C1-C4 thioalkoxy, C1-C4 alkylamino, (C1-C4)(C1-C4) dialkylamino, arylamino, diarylamino, C1-C8 alkarylamino, —NN$R^4$, —OC(═O)$R^5$, and $Ar^1$.

In a further aspect, Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, and C1-C8 alkarylamino. In a still further aspect, Z is selected from halogen, —CN, —$NH_2$, —OH, C1-C4 alkenyl, C1-C4 alkoxy, C1-C4 thioalkoxy, C1-C4 alkylamino, (C1-C4)(C1-C4) dialkylamino, arylamino, diarylamino, and C1-C4 alkarylamino. In yet a further aspect, Z is selected from fluorine, chlorine, —CN, —$NH_2$, —OH, ethenyl, propenyl, —$OCH_3$, —$OCH_2CH_3$, —$OCH_2CH_2CH_3$, —$OCH(CH_3)_2$, —$SCH_3$, —$SCH_2CH_3$, —$SCH_2CH_2CH_3$, —$SCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, —$N(CH(CH_3)_2)_2$, —$NHAr^1$, —$N(Ar^1)_2$, —$N(CH_3)Ar^1$, —$N(CH_2CH_3)Ar^1$, —$N(CH_2CH_2CH_3)Ar^1$, and —$N(CH(CH_3)_2)Ar^1$. In an even further aspect, Z is selected from fluorine, chlorine, —CN, —$NH_2$, —OH, ethenyl, —$OCH_3$, —$OCH_2CH_3$, —$SCH_3$, —$SCH_2CH_3$, —$NHCH_3$, —$NHCH_2CH_3$, —$N(CH_3)_2$, —$N(CH_3)(CH_2CH_3)$, —$NHAr^1$, —$N(Ar^1)_2$, —$N(CH_3)Ar^1$, and —$N(CH_2CH_3)Ar^1$. In a still further aspect, Z is selected from fluorine, chlorine, —CN, —$NH_2$, —OH, —$OCH_3$, —$SCH_3$, —$NHCH_3$, —$N(CH_3)_2$, —$NHAr^1$, —$N(Ar^1)_2$, and —$N(CH_3)Ar^1$.

In a further aspect, Z is selected from C1-C8 alkenyl, C1-C8 alkoxy, C1-C8 thioalkoxy, C1-C8 alkylamino, (C1-C8)(C1-C8) dialkylamino, arylamino, diarylamino, and C1-C8 alkarylamino. In a still further aspect, Z is selected from C1-C4 alkenyl, C1-C4 alkoxy, C1-C4 thioalkoxy, C1-C4 alkylamino, (C1-C4)(C1-C4) dialkylamino, arylamino, diarylamino, and C1-C4 alkarylamino. In yet a further aspect, Z is selected from ethenyl, propenyl, —$OCH_3$, —$OCH_2CH_3$, —$OCH_2CH_2CH_3$, —$OCH(CH_3)_2$, —$SCH_3$, —$SCH_2CH_3$, —$SCH_2CH_2CH_3$, —$SCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, —$N(CH(CH_3)_2)_2$, —$NHAr^1$, —$N(Ar^1)_2$, —$N(CH_3)Ar^1$, —$N(CH_2CH_3)Ar^1$, —$N(CH_2CH_2CH_3)Ar^1$, and —$N(CH(CH_3)_2)Ar^1$. In an even further aspect, Z is selected from ethenyl, —$OCH_3$, —$OCH_2CH_3$, —$SCH_3$, —$SCH_2CH_3$, —$NHCH_3$, —$NHCH_2CH_3$, —$N(CH_3)_2$, —$N(CH_3)(CH_2CH_3)$, —$NHAr^1$, —$N(Ar^1)_2$, —$N(CH_3)Ar^1$, and —$N(CH_2CH_3)Ar^1$. In a still further aspect, Z is selected from —$OCH_3$, —$SCH_3$, —$NHCH_3$, —$N(CH_3)_2$, —$NHAr^1$, —$N(Ar^1)_2$, and —$N(CH_3)Ar^1$.

In a further aspect, Z is selected from halogen, —CN, —$NH_2$, —OH, —$NNR^4$, —$OC(=O)R^5$, and $Ar^1$. In a still further aspect, Z is selected from fluorine, chlorine, —CN, —$NH_2$, —OH, —$NNR^4$, —$OC(=O)R^5$, and $Ar^1$. In yet a further aspect, Z is selected from —$NNR^4$, —$OC(=O)R^5$, and $Ar^1$. In an even further aspect, Z is selected from —$OC(=O)R^5$ and $Ar^1$. In a still further aspect, Z is selected from —$NNR^4$ and —$OC(=O)R^5$. In yet a further aspect, Z is selected from —$NNR^4$ and $Ar^1$. In an even further aspect, Z is —$NNR^4$. In a still further aspect, Z is —$OC(=O)R^5$. In yet a further aspect, Z is $Ar^1$.

In a further aspect, Z is selected from —CN, —$NH_2$, and —OH. In a still further aspect, Z is selected from —$NH_2$, and —OH. In yet a further aspect, Z is selected from —CN and —$NH_2$. In an even further aspect, Z is selected from —CN and —OH. In a still further aspect, Z is —CN. In yet a further aspect, Z is —$NH_2$. In an even further aspect, Z is —OH.

In a further aspect, Z is selected from C1-C8 alkylamino, (C1-C8)(C1-C8) dialkylamino, arylamino, diarylamino, and C1-C8 alkarylamino. In a still further aspect, Z is selected from C1-C4 alkylamino, (C1-C4)(C1-C4) dialkylamino, arylamino, diarylamino, C1-C4 alkarylamino.

In a further aspect, Z is a halogen. In a still further aspect, Z is selected from fluorine and chlorine. In yet a further aspect, Z is chlorine. In an even further aspect, Z is fluorine.

d. $Q^1$, $Q^2$, $Q^3$, and $Q^4$ Groups

In one aspect, each of $Q^1$ and $Q^3$ is independently selected from N and $CR^1$ and each of $Q^2$ and $Q^4$ is independently selected from N and $CR^2$. In a further aspect, at least one of $Q^1$, $Q^2$, $Q^3$, and $Q^4$ is N. In a still further aspect, at least one of $Q^1$ and $Q^3$ is N. In yet a further aspect, at least one of $Q^2$ and $Q^4$ is N.

In one aspect, each of $Q^1$ and $Q^3$ is independently selected from N and $CR^1$ and each of $Q^2$ and $Q^4$ is $CR^2$. In a further aspect, each of $Q^1$ and $Q^3$ is $CR^1$ and each of $Q^2$ and $Q^4$ is $CR^2$.

In a further aspect, each of $Q^1$ and $Q^3$ is independently selected from N and $CR^1$. In a still further aspect, $Q^1$ is N and $Q^3$ is $CR^1$. In yet a further aspect, $Q^1$ is $CR^1$ and $Q^3$ is N. In an even further aspect, each of $Q^1$ and $Q^3$ is $CR^1$. In a still further aspect, each of $Q^1$ and $Q^3$ is N.

In a further aspect, each of $Q^2$ and $Q^4$ is independently selected from N and $CR^2$. In a still further aspect, $Q^2$ is N and $Q^4$ is $CR^2$. In yet a further aspect, $Q^2$ is $CR^2$ and $Q^4$ is N. In an even further aspect, each of $Q^2$ and $Q^4$ is $CR^2$. In a still further aspect, each of $Q^2$ and $Q^4$ is N.

e. $Q^5$, $Q^6$, $Q^7$, and $Q^8$ Groups

In one aspect, each of $Q^5$, $Q^6$, $Q^7$, and $Q^8$ is independently selected from N and $CR^{14}$. In a further aspect, at least one of $Q^5$, $Q^6$, $Q^7$, and $Q^8$ is N. In a still further aspect, at least one of $Q^5$, $Q^6$, $Q^7$, and $Q^8$ is $CR^{14}$. In yet a further aspect, each of $Q^5$, $Q^6$, $Q^7$, and $Q^8$ is $CR^{14}$.

f. R and $R^2$ Groups

In one aspect, each occurrence of $R^1$ and $R^2$ is independently selected from hydrogen, halogen, C1-C8 alkyl, C1-C8 alkoxy, and —$C(=O)NR^{3a}R^{3b}$, or $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —$C(=O)NR^{3a}R^{3b}$. In a further aspect, each occurrence of $R^1$ and $R^2$ is hydrogen.

In one aspect, each occurrence of $R^2$ is optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and —$C(=O)NR^{3a}R^{3b}$. In a further aspect, each occurrence of $R^2$ is optionally covalently bonded and, together with the intermediate atoms, comprise a 5- to 6-membered cycle or heterocycle substituted with 0, 1, 2, or 3 groups independently selected from halogen, C1-C4 alkyl, C1-C4 alkoxy, and —$C(=O)NR^{3a}R^{3b}$. In a still further aspect, each occurrence of $R^2$ is optionally covalently bonded and, together with the intermediate atoms, comprise a 5- to 6-membered cycle or heterocycle substituted with 0, 1, 2, or 3 groups independently selected from fluorine, chlorine, methyl, ethyl, n-propyl, iso-propyl, —$OCH_3$, —$OCH_2CH_3$, —$OCH_2CH_2CH_3$, —$OCH(CH_3)_2$, and —$C(=O)NR^{3a}R^{3b}$. In yet a further aspect, each occurrence of $R^2$ is optionally covalently bonded and, together with the intermediate atoms, comprise a 5- to 6-membered cycle or heterocycle substituted with 0, 1, 2, or 3 groups independently selected from fluorine, chlorine, methyl, ethyl, $—OCH_3$, $—OCH_2CH_3$, and $—C(═O)NR^{3a}R^{3b}$. In an even further aspect, each occurrence of $R^2$ is optionally covalently bonded and, together with the intermediate atoms, comprise a 5- to 6-membered cycle or heterocycle substituted with 0, 1, 2, or 3 groups independently selected from fluorine, chlorine, methyl, $—OCH_3$, and $—C(═O)NR^{3a}R^{3b}$.

In a further aspect, each occurrence of $R^1$ and $R^2$ is independently selected from hydrogen, halogen, C1-C8 alkyl, C1-C8 alkoxy, and $—C(═O)NR^{3a}R^{3b}$. In a still further aspect, each occurrence of $R^1$ and $R^2$ is independently selected from hydrogen, halogen, C1-C4 alkyl, C1-C4 alkoxy, and $—C(═O)NR^{3a}R^{3b}$. In yet a further aspect, each occurrence of $R^1$ and $R^2$ is independently selected from hydrogen, fluorine, chlorine, methyl, ethyl, n-propyl, iso-propyl, $—OCH_3$, $—OCH_2CH_3$, $—OCH_2CH_2CH_3$, $—OCH(CH_3)_2$, and $—C(═O)NR^{3a}R^{3b}$. In an even further aspect, each occurrence of $R^1$ and $R^2$ is independently selected from hydrogen, fluorine, chlorine, methyl, ethyl, $—OCH_3$, $—OCH_2CH_3$, and $—C(═O)NR^{3a}R^{3b}$. In a still further aspect, each occurrence of $R^1$ and $R^2$ is independently selected from hydrogen, fluorine, chlorine, methyl, $—OCH_3$, and $—C(═O)NR^{3a}R^{3b}$.

In a further aspect, each occurrence of $R^1$ and $R^2$ is independently selected from hydrogen, C1-C8 alkyl, C1-C8 alkoxy, and $—C(═O)NR^{3a}R^{3b}$. In a still further aspect, each occurrence of $R^1$ and $R^2$ is independently selected from hydrogen, C1-C4 alkyl, C1-C4 alkoxy, and $—C(═O)NR^{3a}R^{3b}$. In yet a further aspect, each occurrence of $R^1$ and $R^2$ is independently selected from hydrogen, methyl, ethyl, n-propyl, iso-propyl, $—OCH_3$, $—OCH_2CH_3$, $—OCH_2CH_2CH_3$, $—OCH(CH_3)_2$, and $—C(═O)NR^{3a}R^{3b}$. In an even further aspect, each occurrence of $R^1$ and $R^2$ is independently selected from hydrogen, methyl, ethyl, $—OCH_3$, $—OCH_2CH_3$, and $—C(═O)NR^{3a}R^{3b}$. In a still further aspect, each occurrence of $R^1$ and $R^2$ is independently selected from hydrogen, methyl, $—OCH_3$, and $—C(═O)NR^{3a}R^{3b}$.

In a further aspect, each occurrence of $R^1$ and $R^2$ is independently selected from hydrogen, C1-C8 alkyl, and C1-C8 alkoxy. In a still further aspect, each occurrence of $R^1$ and $R^2$ is independently selected from hydrogen, C1-C4 alkyl, and C1-C4 alkoxy. In yet a further aspect, each occurrence of $R^1$ and $R^2$ is independently selected from hydrogen, methyl, ethyl, n-propyl, iso-propyl, $—OCH_3$, $—OCH_2CH_3$, $—OCH_2CH_2CH_3$, and $—OCH(CH_3)_2$. In an even further aspect, each occurrence of $R^1$ and $R^2$ is independently selected from hydrogen, methyl, ethyl, $—OCH_3$, and $—OCH_2CH_3$. In a still further aspect, each occurrence of $R^1$ and $R^2$ is independently selected from hydrogen, methyl, and $—OCH_3$.

In a further aspect, each occurrence of $R^1$ and $R^2$ is independently selected from hydrogen and halogen. In a still further aspect, each occurrence of $R^1$ and $R^2$ is independently selected from hydrogen, fluorine, and chlorine. In yet a further aspect, each occurrence of $R^1$ and $R^2$ is independently selected from hydrogen and chlorine. In a still further aspect, each occurrence of $R^1$ and $R^2$ is independently selected from hydrogen and fluorine.

In a further aspect, $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and $—C(═O)NR^{3a}R^{3b}$. In a still further aspect, $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C4 alkyl, C1-C4 alkoxy, and $—C(═O)NR^{3a}R^{3b}$. In yet a further aspect, $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from fluorine, chlorine, methyl, ethyl, n-propyl, iso-propyl, $—OCH_3$, $—OCH_2CH_3$, $—OCH_2CH_2CH_3$, $—OCH(CH_3)_2$, and $—C(═O)NR^{3a}R^{3b}$. In an even further aspect, $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from fluorine, chlorine, methyl, ethyl, $—OCH_3$, $—OCH_2CH_3$, and $—C(═O)NR^{3a}R^{3b}$. In a still further aspect, $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from fluorine, chlorine, methyl, $—OCH_3$, and $—C(═O)NR^{3a}R^{3b}$.

In a further aspect, $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, —(C1-C8 alkyl)-$CO_2$—(C1-C4 alkyl), and $—C(═O)NR^{3a}R^{3b}$. In a still further aspect, $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C4 alkyl, C1-C4 alkoxy, —(C1-C4 alkyl)-$CO_2$—(C1-C2 alkyl), and $—C(═O)NR^{3a}R^{3b}$. In yet a further aspect, $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from fluorine, chlorine, methyl, ethyl, n-propyl, iso-propyl, $—OCH_3$, $—OCH_2CH_3$, $—OCH_2CH_2CH_3$, $—OCH(CH_3)_2$, $—CH(CH_3)CO_2CH_2CH_3$, $—CH(CH_3)CO_2CH_3$, and $—C(═O)NR^{3a}R^{3b}$. In an even further aspect, $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from fluorine, chlorine, methyl, ethyl, $—OCH_3$, $—OCH_2CH_3$, $—CH(CH_3)CO_2CH_3$, and $—C(═O)NR^{3a}R^{3b}$. In a still further aspect, $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from fluorine, chlorine, methyl, $—OCH_3$, $—CH(CH_3)CO_2CH_3$, and $—C(═O)NR^{3a}R^{3b}$.

In a further aspect, $R^1$ and $R^2$ are optionally covalently bonded and, together with the intermediate atoms, comprise a 5- to 6-membered cycle or heterocycle having 0, 1, or 2 heteroatoms and substituted with 0, 1, or 2 groups independently selected from halogen, C1-C8 alkyl, C1-C8 alkoxy, and $—C(═O)NR^{3a}R^{3b}$. In a still further aspect, $R^1$ and $R^2$ are optionally covalently bonded and, together with the intermediate atoms, comprise a 5- to 6-membered cycle or heterocycle having 0, 1, or 2 heteroatoms and substituted with 0 or 1 group selected from halogen, C1-C8 alkyl, C1-C8 alkoxy, and —C(=O)$NR^{3a}R^{3b}$. In yet a further aspect, $R^1$ and $R^2$ are optionally covalently bonded and, together with the intermediate atoms, comprise a 5- to 6-membered cycle or heterocycle having 0, 1, or 2 heteroatoms and monosubstituted with a group selected from halogen, C1-C8 alkyl, C1-C8 alkoxy, and —C(=O)$NR^{3a}R^{3b}$. In an even further aspect, $R^1$ and $R^2$ are optionally covalently bonded and, together with the intermediate atoms, comprise a 5- to 6-membered cycle or heterocycle having 0, 1, or 2 heteroatoms and unsubstituted.

In a further aspect, $R^1$ and $R^2$ are optionally covalently bonded and, together with the intermediate atoms, comprise a 5- to 6-membered cycle substituted with 0, 1, 2, or 3 groups independently selected from halogen, C1-C8 alkyl, C1-C8 alkoxy, and —C(=O)$NR^{3a}R^{3b}$. In a still further aspect, $R^1$ and $R^2$ are optionally covalently bonded and, together with the intermediate atoms, comprise a 5- to 6-membered cycle substituted with 0, 1, 2, or 3 groups independently selected from halogen, C1-C4 alkyl, C1-C4 alkoxy, and —C(=O)$NR^{3a}R^{3b}$. In yet a further aspect, $R^1$ and $R^2$ are optionally covalently bonded and, together with the intermediate atoms, comprise a 5- to 6-membered cycle substituted with 0, 1, 2, or 3 groups independently selected from fluorine, chlorine, methyl, ethyl, n-propyl, iso-propyl, —$OCH_3$, —$OCH_2CH_3$, —$OCH_2CH_2CH_3$, —$OCH(CH_3)_2$, and —C(=O)$NR^{3a}R^{3b}$. In an even further aspect, $R^1$ and $R^2$ are optionally covalently bonded and, together with the intermediate atoms, comprise a 5- to 6-membered cycle substituted with 0, 1, 2, or 3 groups independently selected from fluorine, chlorine, methyl, ethyl, —$OCH_3$, —$OCH_2CH_3$, and —C(=O)$NR^{3a}R^{3b}$. In a still further aspect, $R^1$ and $R^2$ are optionally covalently bonded and, together with the intermediate atoms, comprise a 5- to 6-membered cycle substituted with 0, 1, 2, or 3 groups independently selected from fluorine, chlorine, methyl, —$OCH_3$, and —C(=O)$NR^{3a}R^{3b}$.

In a further aspect, $R^1$ and $R^2$ are optionally covalently bonded and, together with the intermediate atoms, comprise a 5- to 6-membered cycle substituted with 0, 1, or 2 groups independently selected from halogen, C1-C8 alkyl, C1-C8 alkoxy, and —C(=O)$NR^{3a}R^{3b}$. In a still further aspect, $R^1$ and $R^2$ are optionally covalently bonded and, together with the intermediate atoms, comprise a 5- to 6-membered cycle substituted with 0 or 1 group selected from halogen, C1-C8 alkyl, C1-C8 alkoxy, and —C(=O)$NR^{3a}R^{3b}$. In yet a further aspect, $R^1$ and $R^2$ are optionally covalently bonded and, together with the intermediate atoms, comprise a 5- to 6-membered cycle monosubstituted with a group selected from halogen, C1-C8 alkyl, C1-C8 alkoxy, and —C(=O)$NR^{3a}R^{3b}$. In an even further aspect, $R^1$ and $R^2$ are optionally covalently bonded and, together with the intermediate atoms, comprise a 5- to 6-membered unsubstituted cycle.

In a further aspect, $R^1$ and $R^2$ are optionally covalently bonded and, together with the intermediate atoms, comprise a 5-membered cycle substituted with 0, 1, 2, or 3 groups independently selected from halogen, C1-C8 alkyl, C1-C8 alkoxy, and —C(=O)$NR^{3a}R^{3b}$. In a still further aspect, $R^1$ and $R^2$ are optionally covalently bonded and, together with the intermediate atoms, comprise a 5-membered cycle substituted with 0, 1, 2, or 3 groups independently selected from halogen, C1-C4 alkyl, C1-C4 alkoxy, and —C(=O)$NR^{3a}R^{3b}$. In yet a further aspect, $R^1$ and $R^2$ are optionally covalently bonded and, together with the intermediate atoms, comprise a 5-membered cycle substituted with 0, 1, 2, or 3 groups independently selected from fluorine, chlorine, methyl, ethyl, n-propyl, iso-propyl, —$OCH_3$, —$OCH_2CH_3$, —$OCH_2CH_2CH_3$, —$OCH(CH_3)_2$, and —C(=O)$NR^{3a}R^{3b}$. In an even further aspect, $R^1$ and $R^2$ are optionally covalently bonded and, together with the intermediate atoms, comprise a 5-membered cycle substituted with 0, 1, 2, or 3 groups independently selected from fluorine, chlorine, methyl, ethyl, —$OCH_3$, —$OCH_2CH_3$, and —C(=O)$NR^{3a}R^{3b}$. In a still further aspect, $R^1$ and $R^2$ are optionally covalently bonded and, together with the intermediate atoms, comprise a 5-membered cycle substituted with 0, 1, 2, or 3 groups independently selected from fluorine, chlorine, methyl, —$OCH_3$, and —C(=O)$NR^{3a}R^{3b}$.

In a further aspect, $R^1$ and $R^2$ are optionally covalently bonded and, together with the intermediate atoms, comprise a 5-membered cycle substituted with 0, 1, or 2 groups independently selected from halogen, C1-C8 alkyl, C1-C8 alkoxy, and —C(=O)$NR^{3a}R^{3b}$. In a still further aspect, $R^1$ and $R^2$ are optionally covalently bonded and, together with the intermediate atoms, comprise a 5-membered cycle substituted with 0 or 1 group selected from halogen, C1-C8 alkyl, C1-C8 alkoxy, and —C(=O)$NR^{3a}R^{3b}$. In yet a further aspect, $R^1$ and $R^2$ are optionally covalently bonded and, together with the intermediate atoms, comprise a 5-membered cycle monosubstituted with a group selected from halogen, C1-C8 alkyl, C1-C8 alkoxy, and —C(=O)$NR^{3a}R^{3b}$. In an even further aspect, $R^1$ and $R^2$ are optionally covalently bonded and, together with the intermediate atoms, comprise a 5-membered unsubstituted cycle.

In a further aspect, $R^1$ and $R^2$ are optionally covalently bonded and, together with the intermediate atoms, comprise a 6-membered cycle substituted with 0, 1, 2, or 3 groups independently selected from halogen, C1-C8 alkyl, C1-C8 alkoxy, and —C(=O)$NR^{3a}R^{3b}$. In a still further aspect, $R^1$ and $R^2$ are optionally covalently bonded and, together with the intermediate atoms, comprise a 6-membered cycle substituted with 0, 1, 2, or 3 groups independently selected from halogen, C1-C4 alkyl, C1-C4 alkoxy, and —C(=O)$NR^{3a}R^{3b}$. In yet a further aspect, $R^1$ and $R^2$ are optionally covalently bonded and, together with the intermediate atoms, comprise a 6-membered cycle substituted with 0, 1, 2, or 3 groups independently selected from fluorine, chlorine, methyl, ethyl, n-propyl, iso-propyl, —$OCH_3$, —$OCH_2CH_3$, —$OCH_2CH_2CH_3$, —$OCH(CH_3)_2$, and —C(=O)$NR^{3a}R^{3b}$. In an even further aspect, $R^1$ and $R^2$ are optionally covalently bonded and, together with the intermediate atoms, comprise a 6-membered cycle substituted with 0, 1, 2, or 3 groups independently selected from fluorine, chlorine, methyl, ethyl, —$OCH_3$, —$OCH_2CH_3$, and —C(=O)$NR^{3a}R^{3b}$. In a still further aspect, $R^1$ and $R^2$ are optionally covalently bonded and, together with the intermediate atoms, comprise a 6-membered cycle substituted with 0, 1, 2, or 3 groups independently selected from fluorine, chlorine, methyl, —$OCH_3$, and —C(=O)$NR^{3a}R^{3b}$.

In a further aspect, $R^1$ and $R^2$ are optionally covalently bonded and, together with the intermediate atoms, comprise a 6-membered cycle substituted with 0, 1, or 2 groups independently selected from halogen, C1-C8 alkyl, C1-C8 alkoxy, and —C(=O)$NR^{3a}R^{3b}$. In a still further aspect, $R^1$ and $R^2$ are optionally covalently bonded and, together with the intermediate atoms, comprise a 6-membered cycle substituted with 0 or 1 group selected from halogen, C1-C8 alkyl, C1-C8 alkoxy, and —C(=O)$NR^{3a}R^{3b}$. In yet a further aspect, $R^1$ and $R^2$ are optionally covalently bonded and, together with the intermediate atoms, comprise a 6-membered cycle monosubstituted with a group selected from halogen, C1-C8 alkyl, C1-C8 alkoxy, and —C(═O)$NR^{3a}R^{3b}$. In an even further aspect, $R^1$ and $R^2$ are optionally covalently bonded and, together with the intermediate atoms, comprise a 6-membered unsubstituted cycle.

In a further aspect, $R^1$ and $R^2$ are optionally covalently bonded and, together with the intermediate atoms, comprise a 5- to 6-membered heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$. In a still further aspect, $R^1$ and $R^2$ are optionally covalently bonded and, together with the intermediate atoms, comprise a 5- to 6-membered heterocycle substituted with 0, 1, 2, or 3 groups independently selected from halogen, C1-C4 alkyl, C1-C4 alkoxy, and —C(═O)$NR^{3a}R^{3b}$. In yet a further aspect, $R^1$ and $R^2$ are optionally covalently bonded and, together with the intermediate atoms, comprise a 5- to 6-membered heterocycle substituted with 0, 1, 2, or 3 groups independently selected from fluorine, chlorine, methyl, ethyl, n-propyl, iso-propyl, —$OCH_3$, —$OCH_2CH_3$, —$OCH_2CH_2CH_3$, —$OCH(CH_3)_2$, and —C(═O)$NR^{3a}R^{3b}$. In an even further aspect, $R^1$ and $R^2$ are optionally covalently bonded and, together with the intermediate atoms, comprise a 5- to 6-membered heterocycle substituted with 0, 1, 2, or 3 groups independently selected from fluorine, chlorine, methyl, ethyl, —$OCH_3$, —$OCH_2CH_3$, and —C(═O)$NR^{3a}R^{3b}$. In a still further aspect, $R^1$ and $R^2$ are optionally covalently bonded and, together with the intermediate atoms, comprise a 5- to 6-membered heterocycle substituted with 0, 1, 2, or 3 groups independently selected from fluorine, chlorine, methyl, —$OCH_3$, and —C(═O)$NR^{3a}R^{3b}$.

In a further aspect, $R^1$ and $R^2$ are optionally covalently bonded and, together with the intermediate atoms, comprise a 5- to 6-membered heterocycle substituted with 0, 1, or 2 groups independently selected from halogen, C1-C8 alkyl, C1-C8 alkoxy, and —C(═O)$NR^{3a}R^{3b}$. In a still further aspect, $R^1$ and $R^2$ are optionally covalently bonded and, together with the intermediate atoms, comprise a 5- to 6-membered heterocycle substituted with 0 or 1 group selected from halogen, C1-C8 alkyl, C1-C8 alkoxy, and —C(═O)$NR^{3a}R^{3b}$. In yet a further aspect, $R^1$ and $R^2$ are optionally covalently bonded and, together with the intermediate atoms, comprise a 5- to 6-membered heterocycle monosubstituted with a group selected from halogen, C1-C8 alkyl, C1-C8 alkoxy, and —C(═O)$NR^{3a}R^{3b}$. In an even further aspect, $R^1$ and $R^2$ are optionally covalently bonded and, together with the intermediate atoms, comprise a 5- to 6-membered unsubstituted heterocycle.

In a further aspect, $R^1$ and $R^2$ are optionally covalently bonded and, together with the intermediate atoms, comprise a 5-membered heterocycle substituted with 0, 1, 2, or 3 groups independently selected from halogen, C1-C8 alkyl, C1-C8 alkoxy, and —C(═O)$NR^{3a}R^{3b}$. In a still further aspect, $R^1$ and $R^2$ are optionally covalently bonded and, together with the intermediate atoms, comprise a 5-membered heterocycle substituted with 0, 1, 2, or 3 groups independently selected from halogen, C1-C4 alkyl, C1-C4 alkoxy, and —C(═O)$NR^{3a}R^{3b}$. In yet a further aspect, $R^1$ and $R^2$ are optionally covalently bonded and, together with the intermediate atoms, comprise a 5-membered heterocycle substituted with 0, 1, 2, or 3 groups independently selected from fluorine, chlorine, methyl, ethyl, n-propyl, iso-propyl, —$OCH_3$, —$OCH_2CH_3$, —$OCH_2CH_2CH_3$, —$OCH(CH_3)_2$, and —C(═O)$NR^{3a}R^{3b}$. In an even further aspect, $R^1$ and $R^2$ are optionally covalently bonded and, together with the intermediate atoms, comprise a 5-membered heterocycle substituted with 0, 1, 2, or 3 groups independently selected from fluorine, chlorine, methyl, ethyl, —$OCH_3$, —$OCH_2CH_3$, and —C(═O)$NR^{3a}R^{3b}$. In a still further aspect, $R^1$ and $R^2$ are optionally covalently bonded and, together with the intermediate atoms, comprise a 5-membered heterocycle substituted with 0, 1, 2, or 3 groups independently selected from fluorine, chlorine, methyl, —$OCH_3$, and —C(═O)$NR^{3a}R^{3b}$.

In a further aspect, $R^1$ and $R^2$ are optionally covalently bonded and, together with the intermediate atoms, comprise a 5-membered heterocycle substituted with 0, 1, or 2 groups independently selected from halogen, C1-C8 alkyl, C1-C8 alkoxy, and —C(═O)$NR^{3a}R^{3b}$. In a still further aspect, $R^1$ and $R^2$ are optionally covalently bonded and, together with the intermediate atoms, comprise a 5-membered heterocycle substituted with 0 or 1 group selected from halogen, C1-C8 alkyl, C1-C8 alkoxy, and —C(═O)$NR^{3a}R^{3b}$. In yet a further aspect, $R^1$ and $R^2$ are optionally covalently bonded and, together with the intermediate atoms, comprise a 5-membered heterocycle monosubstituted with a group selected from halogen, C1-C8 alkyl, C1-C8 alkoxy, and —C(═O)$NR^{3a}R^{3b}$. In an even further aspect, $R^1$ and $R^2$ are optionally covalently bonded and, together with the intermediate atoms, comprise a 5-membered unsubstituted heterocycle.

In a further aspect, $R^1$ and $R^2$ are optionally covalently bonded and, together with the intermediate atoms, comprise a 6-membered heterocycle substituted with 0, 1, 2, or 3 groups independently selected from halogen, C1-C8 alkyl, C1-C8 alkoxy, and —C(═O)$NR^{3a}R^{3b}$. In a still further aspect, $R^1$ and $R^2$ are optionally covalently bonded and, together with the intermediate atoms, comprise a 6-membered heterocycle substituted with 0, 1, 2, or 3 groups independently selected from halogen, C1-C4 alkyl, C1-C4 alkoxy, and —C(═O)$NR^{3a}R^{3b}$. In yet a further aspect, $R^1$ and $R^2$ are optionally covalently bonded and, together with the intermediate atoms, comprise a 6-membered heterocycle substituted with 0, 1, 2, or 3 groups independently selected from fluorine, chlorine, methyl, ethyl, n-propyl, iso-propyl, —$OCH_3$, —$OCH_2CH_3$, —$OCH_2CH_2CH_3$, —$OCH(CH_3)_2$, and —C(═O)$NR^{3a}R^{3b}$. In an even further aspect, $R^1$ and $R^2$ are optionally covalently bonded and, together with the intermediate atoms, comprise a 6-membered heterocycle substituted with 0, 1, 2, or 3 groups independently selected from fluorine, chlorine, methyl, ethyl, —$OCH_3$, —$OCH_2CH_3$, and —C(═O)$NR^{3a}R^{3b}$. In a still further aspect, $R^1$ and $R^2$ are optionally covalently bonded and, together with the intermediate atoms, comprise a 6-membered heterocycle substituted with 0, 1, 2, or 3 groups independently selected from fluorine, chlorine, methyl, —$OCH_3$, and —C(═O)$NR^{3a}R^{3b}$.

In a further aspect, $R^1$ and $R^2$ are optionally covalently bonded and, together with the intermediate atoms, comprise a 6-membered heterocycle substituted with 0, 1, or 2 groups independently selected from halogen, C1-C8 alkyl, C1-C8 alkoxy, and —C(═O)$NR^{3a}R^{3b}$. In a still further aspect, $R^1$ and $R^2$ are optionally covalently bonded and, together with the intermediate atoms, comprise a 6-membered heterocycle substituted with 0 or 1 group selected from halogen, C1-C8 alkyl, C1-C8 alkoxy, and —C(═O)$NR^{3a}R^{3b}$. In yet a further aspect, $R^1$ and $R^2$ are optionally covalently bonded and, together with the intermediate atoms, comprise a 6-membered heterocycle monosubstituted with a group selected from halogen, C1-C8 alkyl, C1-C8 alkoxy, and —C(═O)$NR^{3a}R^{3b}$. In an even further aspect, $R^1$ and $R^2$ are optionally covalently bonded and, together with the intermediate atoms, comprise a 6-membered unsubstituted heterocycle.

In a further aspect, each occurrence of $R^2$ is optionally covalently bonded and, together with the intermediate atoms, comprise a 5- to 6-membered cycle substituted with 0, 1, 2, or 3 groups independently selected from halogen, C1-C8 alkyl, C1-C8 alkoxy, and —C(═O)$NR^{3a}R^{3b}$. In a still further aspect, each occurrence of $R^2$ is optionally covalently bonded and, together with the intermediate atoms, comprise a 5- to 6-membered cycle substituted with 0, 1, 2, or 3 groups independently selected from halogen, C1-C4 alkyl, C1-C4 alkoxy, and —C(═O)$NR^{3a}R^{3b}$. In yet a further aspect, each occurrence of $R^2$ is optionally covalently bonded and, together with the intermediate atoms, comprise a 5- to 6-membered cycle substituted with 0, 1, 2, or 3 groups independently selected from fluorine, chlorine, methyl, ethyl, n-propyl, iso-propyl, —$OCH_3$, —$OCH_2CH_3$, —$OCH_2CH_2CH_3$, —$OCH(CH_3)_2$, and —C(═O)$NR^{3a}R^{3b}$. In an even further aspect, each occurrence of $R^2$ is optionally covalently bonded and, together with the intermediate atoms, comprise a 5- to 6-membered cycle substituted with 0, 1, 2, or 3 groups independently selected from fluorine, chlorine, methyl, ethyl, —$OCH_3$, —$OCH_2CH_3$, and —C(═O)$NR^{3a}R^{3b}$. In a still further aspect, each occurrence of $R^2$ is optionally covalently bonded and, together with the intermediate atoms, comprise a 5- to 6-membered cycle substituted with 0, 1, 2, or 3 groups independently selected from fluorine, chlorine, methyl, —$OCH_3$, and —C(═O)$NR^{3a}R^{3b}$.

In a further aspect, each occurrence of $R^2$ is optionally covalently bonded and, together with the intermediate atoms, comprise a 5- to 6-membered cycle substituted with 0, 1, or 2 groups independently selected from halogen, C1-C8 alkyl, C1-C8 alkoxy, and —C(═O)$NR^{3a}R^{3b}$. In a still further aspect, each occurrence of $R^2$ is optionally covalently bonded and, together with the intermediate atoms, comprise a 5- to 6-membered cycle substituted with 0 or 1 group selected from halogen, C1-C8 alkyl, C1-C8 alkoxy, and —C(═O)$NR^{3a}R^{3b}$. In yet a further aspect, each occurrence of $R^2$ is optionally covalently bonded and, together with the intermediate atoms, comprise a 5- to 6-membered cycle monosubstituted with a group selected from halogen, C1-C8 alkyl, C1-C8 alkoxy, and —C(═O)$NR^{3a}R^{3b}$. In an even further aspect, each occurrence of $R^2$ is optionally covalently bonded and, together with the intermediate atoms, comprise a 5- to 6-membered unsubstituted cycle.

In a further aspect, each occurrence of $R^2$ is optionally covalently bonded and, together with the intermediate atoms, comprise a 5-membered cycle substituted with 0, 1, 2, or 3 groups independently selected from halogen, C1-C8 alkyl, C1-C8 alkoxy, and —C(═O)$NR^{3a}R^{3b}$. In a still further aspect, each occurrence of $R^2$ is optionally covalently bonded and, together with the intermediate atoms, comprise a 5-membered cycle substituted with 0, 1, 2, or 3 groups independently selected from halogen, C1-C4 alkyl, C1-C4 alkoxy, and —C(═O)$NR^{3a}R^{3b}$. In yet a further aspect, each occurrence of $R^2$ is optionally covalently bonded and, together with the intermediate atoms, comprise a 5-membered cycle substituted with 0, 1, 2, or 3 groups independently selected from fluorine, chlorine, methyl, ethyl, n-propyl, iso-propyl, —$OCH_3$, —$OCH_2CH_3$, —$OCH_2CH_2CH_3$, —$OCH(CH_3)_2$, and —C(═O)$NR^{3a}R^{3b}$. In an even further aspect, each occurrence of $R^2$ is optionally covalently bonded and, together with the intermediate atoms, comprise a 5-membered cycle substituted with 0, 1, 2, or 3 groups independently selected from fluorine, chlorine, methyl, ethyl, —$OCH_3$, —$OCH_2CH_3$, and —C(═O)$NR^{3a}R^{3b}$. In a still further aspect, each occurrence of $R^2$ is optionally covalently bonded and, together with the intermediate atoms, comprise a 5-membered cycle substituted with 0, 1, 2, or 3 groups independently selected from fluorine, chlorine, methyl, —$OCH_3$, and —C(═O)$NR^{3a}R^{3b}$.

In a further aspect, each occurrence of $R^2$ is optionally covalently bonded and, together with the intermediate atoms, comprise a 5-membered cycle substituted with 0, 1, or 2 groups independently selected from halogen, C1-C8 alkyl, C1-C8 alkoxy, and —C(═O)$NR^{3a}R^{3b}$. In a still further aspect, each occurrence of $R^2$ is optionally covalently bonded and, together with the intermediate atoms, comprise a 5-membered cycle substituted with 0 or 1 group selected from halogen, C1-C8 alkyl, C1-C8 alkoxy, and —C(═O)$NR^{3a}R^{3b}$. In yet a further aspect, each occurrence of $R^2$ is optionally covalently bonded and, together with the intermediate atoms, comprise a 5-membered cycle monosubstituted with a group selected from halogen, C1-C8 alkyl, C1-C8 alkoxy, and —C(═O)$NR^{3a}R^{3b}$. In an even further aspect, each occurrence of $R^2$ is optionally covalently bonded and, together with the intermediate atoms, comprise a 5-membered unsubstituted cycle.

In a further aspect, each occurrence of $R^2$ is optionally covalently bonded and, together with the intermediate atoms, comprise a 6-membered cycle substituted with 0, 1, 2, or 3 groups independently selected from halogen, C1-C8 alkyl, C1-C8 alkoxy, and —C(═O)$NR^{3a}R^{3b}$. In a still further aspect, each occurrence of $R^2$ is optionally covalently bonded and, together with the intermediate atoms, comprise a 6-membered cycle substituted with 0, 1, 2, or 3 groups independently selected from halogen, C1-C4 alkyl, C1-C4 alkoxy, and —C(═O)$NR^{3a}R^{3b}$. In yet a further aspect, each occurrence of $R^2$ is optionally covalently bonded and, together with the intermediate atoms, comprise a 6-membered cycle substituted with 0, 1, 2, or 3 groups independently selected from fluorine, chlorine, methyl, ethyl, n-propyl, iso-propyl, —$OCH_3$, —$OCH_2CH_3$, —$OCH_2CH_2CH_3$, —$OCH(CH_3)_2$, and —C(═O)$NR^{3a}R^{3b}$. In an even further aspect, each occurrence of $R^2$ is optionally covalently bonded and, together with the intermediate atoms, comprise a 6-membered cycle substituted with 0, 1, 2, or 3 groups independently selected from fluorine, chlorine, methyl, ethyl, —$OCH_3$, —$OCH_2CH_3$, and —C(═O)$NR^{3a}R^{3b}$. In a still further aspect, each occurrence of $R^2$ is optionally covalently bonded and, together with the intermediate atoms, comprise a 6-membered cycle substituted with 0, 1, 2, or 3 groups independently selected from fluorine, chlorine, methyl, —$OCH_3$, and —C(═O)$NR^{3a}R^{3b}$.

In a further aspect, each occurrence of $R^2$ is optionally covalently bonded and, together with the intermediate atoms, comprise a 6-membered cycle substituted with 0, 1, or 2 groups independently selected from halogen, C1-C8 alkyl, C1-C8 alkoxy, and —C(═O)$NR^{3a}R^{3b}$. In a still further aspect, each occurrence of $R^2$ is optionally covalently bonded and, together with the intermediate atoms, comprise a 6-membered cycle substituted with 0 or 1 group selected from halogen, C1-C8 alkyl, C1-C8 alkoxy, and —C(═O)$NR^{3a}R^{3b}$. In yet a further aspect, each occurrence of $R^2$ is optionally covalently bonded and, together with the intermediate atoms, comprise a 6-membered cycle monosubstituted with a group selected from halogen, C1-C8 alkyl, C1-C8 alkoxy, and —C(═O)$NR^{3a}R^{3b}$. In an even further aspect, each occurrence of $R^2$ is optionally covalently bonded and, together with the intermediate atoms, comprise a 6-membered unsubstituted cycle.

In a further aspect, each occurrence of $R^2$ is optionally covalently bonded and, together with the intermediate atoms, comprise a 5- to 6-membered heterocycle substituted with 0, 1, 2, or 3 groups independently selected from halogen, C1-C8 alkyl, C1-C8 alkoxy, and —C(=O)NR$^{3a}$R$^{3b}$. In a still further aspect, each occurrence of $R^2$ is optionally covalently bonded and, together with the intermediate atoms, comprise a 5- to 6-membered heterocycle substituted with 0, 1, 2, or 3 groups independently selected from halogen, C1-C4 alkyl, C1-C4 alkoxy, and —C(=O)NR$^{3a}$R$^{3b}$. In yet a further aspect, each occurrence of $R^2$ is optionally covalently bonded and, together with the intermediate atoms, comprise a 5- to 6-membered heterocycle substituted with 0, 1, 2, or 3 groups independently selected from fluorine, chlorine, methyl, ethyl, n-propyl, iso-propyl, —$OCH_3$, —$OCH_2CH_3$, —$OCH_2CH_2CH_3$, —$OCH(CH_3)_2$, and —C(=O)NR$^{3a}$R$^{3b}$. In an even further aspect, each occurrence of $R^2$ is optionally covalently bonded and, together with the intermediate atoms, comprise a 5- to 6-membered heterocycle substituted with 0, 1, 2, or 3 groups independently selected from fluorine, chlorine, methyl, ethyl, —$OCH_3$, —$OCH_2CH_3$, and —C(=O)NR$^{3a}$R$^{3b}$. In a still further aspect, each occurrence of $R^2$ is optionally covalently bonded and, together with the intermediate atoms, comprise a 5- to 6-membered heterocycle substituted with 0, 1, 2, or 3 groups independently selected from fluorine, chlorine, methyl, —$OCH_3$, and —C(=O)NR$^{3a}$R$^{3b}$.

In a further aspect, each occurrence of $R^2$ is optionally covalently bonded and, together with the intermediate atoms, comprise a 5- to 6-membered heterocycle substituted with 0, 1, or 2 groups independently selected from halogen, C1-C8 alkyl, C1-C8 alkoxy, and —C(=O)NR$^{3a}$R$^{3b}$. In a still further aspect, each occurrence of $R^2$ is optionally covalently bonded and, together with the intermediate atoms, comprise a 5- to 6-membered heterocycle substituted with 0 or 1 group selected from halogen, C1-C8 alkyl, C1-C8 alkoxy, and —C(=O)NR$^{3a}$R$^{3b}$. In yet a further aspect, each occurrence of $R^2$ is optionally covalently bonded and, together with the intermediate atoms, comprise a 5- to 6-membered heterocycle monosubstituted with a group selected from halogen, C1-C8 alkyl, C1-C8 alkoxy, and —C(=O)NR$^{3a}$R$^{3b}$. In an even further aspect, each occurrence of $R^2$ is optionally covalently bonded and, together with the intermediate atoms, comprise a 5- to 6-membered unsubstituted heterocycle.

In a further aspect, each occurrence of $R^2$ is optionally covalently bonded and, together with the intermediate atoms, comprise a 5-membered heterocycle substituted with 0, 1, 2, or 3 groups independently selected from halogen, C1-C8 alkyl, C1-C8 alkoxy, and —C(=O)NR$^{3a}$R$^{3b}$. In a still further aspect, each occurrence of $R^2$ is optionally covalently bonded and, together with the intermediate atoms, comprise a 5-membered heterocycle substituted with 0, 1, 2, or 3 groups independently selected from halogen, C1-C4 alkyl, C1-C4 alkoxy, and —C(=O)NR$^{3a}$R$^{3b}$. In yet a further aspect, each occurrence of $R^2$ is optionally covalently bonded and, together with the intermediate atoms, comprise a 5-membered heterocycle substituted with 0, 1, 2, or 3 groups independently selected from fluorine, chlorine, methyl, ethyl, n-propyl, iso-propyl, —$OCH_3$, —$OCH_2CH_3$, —$OCH_2CH_2CH_3$, —$OCH(CH_3)_2$, and —C(=O)NR$^{3a}$R$^{3b}$. In an even further aspect, each occurrence of $R^2$ is optionally covalently bonded and, together with the intermediate atoms, comprise a 5-membered heterocycle substituted with 0, 1, 2, or 3 groups independently selected from fluorine, chlorine, methyl, ethyl, —$OCH_3$, —$OCH_2CH_3$, and —C(=O)NR$^{3a}$R$^{3b}$. In a still further aspect, each occurrence of $R^2$ is optionally covalently bonded and, together with the intermediate atoms, comprise a 5-membered heterocycle substituted with 0, 1, 2, or 3 groups independently selected from fluorine, chlorine, methyl, —$OCH_3$, and —C(=O)NR$^{3a}$R$^{3b}$.

In a further aspect, each occurrence of $R^2$ is optionally covalently bonded and, together with the intermediate atoms, comprise a 5-membered heterocycle substituted with 0, 1, or 2 groups independently selected from halogen, C1-C8 alkyl, C1-C8 alkoxy, and —C(=O)NR$^{3a}$R$^{3b}$. In a still further aspect, each occurrence of $R^2$ is optionally covalently bonded and, together with the intermediate atoms, comprise a 5-membered heterocycle substituted with 0 or 1 group selected from halogen, C1-C8 alkyl, C1-C8 alkoxy, and —C(=O)NR$^{3a}$R$^{3b}$. In yet a further aspect, each occurrence of $R^2$ is optionally covalently bonded and, together with the intermediate atoms, comprise a 5-membered heterocycle monosubstituted with a group selected from halogen, C1-C8 alkyl, C1-C8 alkoxy, and —C(=O)NR$^{3a}$R$^{3b}$. In an even further aspect, each occurrence of $R^2$ is optionally covalently bonded and, together with the intermediate atoms, comprise a 5-membered unsubstituted heterocycle.

In a further aspect, each occurrence of $R^2$ is optionally covalently bonded and, together with the intermediate atoms, comprise a 6-membered heterocycle substituted with 0, 1, 2, or 3 groups independently selected from halogen, C1-C8 alkyl, C1-C8 alkoxy, and —C(=O)NR$^{3a}$R$^{3b}$. In a still further aspect, each occurrence of $R^2$ is optionally covalently bonded and, together with the intermediate atoms, comprise a 6-membered heterocycle substituted with 0, 1, 2, or 3 groups independently selected from halogen, C1-C4 alkyl, C1-C4 alkoxy, and —C(=O)NR$^{3a}$R$^{3b}$. In yet a further aspect, each occurrence of $R^2$ is optionally covalently bonded and, together with the intermediate atoms, comprise a 6-membered heterocycle substituted with 0, 1, 2, or 3 groups independently selected from fluorine, chlorine, methyl, ethyl, n-propyl, iso-propyl, —$OCH_3$, —$OCH_2CH_3$, —$OCH_2CH_2CH_3$, —$OCH(CH_3)_2$, and —C(=O)NR$^{3a}$R$^{3b}$. In an even further aspect, each occurrence of $R^2$ is optionally covalently bonded and, together with the intermediate atoms, comprise a 6-membered heterocycle substituted with 0, 1, 2, or 3 groups independently selected from fluorine, chlorine, methyl, ethyl, —$OCH_3$, —$OCH_2CH_3$, and —C(=O)NR$^{3a}$R$^{3b}$. In a still further aspect, each occurrence of $R^2$ is optionally covalently bonded and, together with the intermediate atoms, comprise a 6-membered heterocycle substituted with 0, 1, 2, or 3 groups independently selected from fluorine, chlorine, methyl, —$OCH_3$, and —C(=O)NR$^{3a}$R$^{3b}$.

In a further aspect, each occurrence of $R^2$ is optionally covalently bonded and, together with the intermediate atoms, comprise a 6-membered heterocycle substituted with 0, 1, or 2 groups independently selected from halogen, C1-C8 alkyl, C1-C8 alkoxy, and —C(=O)NR$^{3a}$R$^{3b}$. In a still further aspect, each occurrence of $R^2$ is optionally covalently bonded and, together with the intermediate atoms, comprise a 6-membered heterocycle substituted with 0 or 1 group selected from halogen, C1-C8 alkyl, C1-C8 alkoxy, and —C(=O)NR$^{3a}$R$^{3b}$. In yet a further aspect, each occurrence of $R^2$ is optionally covalently bonded and, together with the intermediate atoms, comprise a 6-membered heterocycle monosubstituted with a group selected from halogen, C1-C8 alkyl, C1-C8 alkoxy, and —C(=O)NR$^{3a}$R$^{3b}$. In an even further aspect, each occurrence of $R^2$ is optionally covalently bonded and, together with the intermediate atoms, comprise a 6-membered unsubstituted heterocycle.

g. $R^{3a}$ and $R^{3b}$ Groups

In one aspect, each of $R^{3a}$ and $R^{3b}$ is independently selected from hydrogen and C1-C4 alkyl. In a further aspect, each of $R^{3a}$ and $R^{3b}$ is independently selected from hydrogen, methyl, ethyl, n-propyl, and iso-propyl. In a still further aspect, each of $R^{3a}$ and $R^{3b}$ is independently selected from hydrogen, methyl, and ethyl. In yet a further aspect, each of $R^{3a}$ and $R^{3b}$ is independently selected from hydrogen and ethyl. In an even further aspect, each of $R^{3a}$ and $R^{3b}$ is independently selected from hydrogen and methyl. In a still further aspect, each of $R^{3a}$ and $R^{3b}$ is hydrogen.

In a further aspect, each of $R^{3a}$ and $R^{3b}$ is independently selected from C1-C4 alkyl. In a still further aspect, each of $R^{3a}$ and $R^{3b}$ is independently selected from methyl, ethyl, n-propyl, and iso-propyl. In yet a further aspect, each of $R^{3a}$ and $R^{3b}$ is independently selected from methyl and ethyl. In an even further aspect, each of $R^{3a}$ and $R^{3b}$ is ethyl. In a still further aspect, each of $R^{3a}$ and $R^{3b}$ is methyl.

In a further aspect, $R^{3a}$ is hydrogen and $R^{3b}$ is C1-C4 alkyl. In a still further aspect, $R^{3a}$ is hydrogen and $R^{3b}$ is selected from methyl, ethyl, n-propyl, and iso-propyl. In yet a further aspect, $R^{3a}$ is hydrogen and $R^{3b}$ is selected from methyl and ethyl. In an even further aspect, $R^{3a}$ is hydrogen and $R^{3b}$ is ethyl. In a still further aspect, $R^{3a}$ is hydrogen and $R^{3b}$ is methyl.

h. $R^4$ Groups

In one aspect, $R^4$ is selected from hydrogen and C1-C8 alkyl. In a further aspect, $R^4$ is selected from hydrogen and C1-C4 alkyl. In a still further aspect, $R^4$ is selected from hydrogen, methyl, ethyl, n-propyl, and iso-propyl. In yet a further aspect, $R^4$ is hydrogen.

In a further aspect, $R^4$ is C1-C8 alkyl. In a still further aspect, $R^4$ is selected from methyl, ethyl, n-propyl, iso-propyl, n-butyl, sec-butyl, iso-butyl, and tert-butyl. In yet a further aspect, $R^4$ is selected from methyl, ethyl, n-propyl, and iso-propyl. In an even further aspect, $R^4$ is selected from methyl and ethyl. In a still further aspect, $R^4$ is ethyl. In yet a further aspect, $R^4$ is methyl.

i. $R^5$ Groups

In one aspect, $R^5$ is C1-C8 alkyl. In a further aspect, $R^5$ is selected from methyl, ethyl, n-propyl, iso-propyl, n-butyl, sec-butyl, iso-butyl, and tert-butyl. In a still further aspect, $R^5$ is selected from methyl, ethyl, n-propyl, and iso-propyl. In yet a further aspect, $R^5$ is selected from methyl and ethyl. In an even further aspect, $R^5$ is ethyl. In a still further aspect, $R^5$ is methyl.

j. $R^6$ and $R^7$ Groups

In one aspect, each of $R^6$ and $R^7$ is independently selected from C1-C8 alkyl. In a further aspect, each of $R^6$ and $R^7$ is independently selected from methyl, ethyl, n-propyl, iso-propyl, n-butyl, sec-butyl, iso-butyl, and tert-butyl. In a still further aspect, each of $R^6$ and $R^7$ is independently selected from methyl, ethyl, n-propyl, and iso-propyl. In yet a further aspect, each of $R^6$ and $R^7$ is independently selected from methyl and ethyl. In an even further aspect, each of $R^6$ and $R^7$ is ethyl. In a still further aspect, each of $R^6$ and $R^7$ is methyl.

k. $R^{11a}$ and $R^{11b}$ Groups

In one aspect, each of $R^{11a}$ and $R^{11b}$ is independently selected from hydrogen and C1-C4 alkyl. In a further aspect, each of $R^{11a}$ and $R^{11b}$ is independently selected from hydrogen, methyl, ethyl, n-propyl, and iso-propyl. In a still further aspect, each of $R^{11a}$ and $R^{11b}$ is independently selected from hydrogen, methyl, and ethyl. In yet a further aspect, each of $R^{11a}$ and $R^{11b}$ is independently selected from hydrogen and ethyl. In an even further aspect, each of $R^{11a}$ and $R^{11b}$ is independently selected from hydrogen and methyl. In a still further aspect, each of $R^{11a}$ and $R^{11b}$ is hydrogen.

In a further aspect, each of $R^{11a}$ and $R^{11b}$ is independently selected from C1-C4 alkyl. In a still further aspect, each of $R^{11a}$ and $R^{11b}$ is independently selected from methyl, ethyl, n-propyl, and iso-propyl. In yet a further aspect, each of $R^{11a}$ and $R^{11b}$ is independently selected from methyl and ethyl. In an even further aspect, each of $R^{11a}$ and $R^{11b}$ is ethyl. In a still further aspect, each of $R^{11a}$ and $R^{11b}$ is methyl.

In a further aspect, $R^{11a}$ is hydrogen and $R^{11b}$ is C1-C4 alkyl. In a still further aspect, $R^{11a}$ is hydrogen and $R^{11b}$ is selected from methyl, ethyl, n-propyl, and iso-propyl. In yet a further aspect, $R^{11a}$ is hydrogen and $R^{11b}$ is selected from methyl and ethyl. In an even further aspect, $R^{11a}$ is hydrogen and $R^{11b}$ is ethyl. In a still further aspect, $R^{11a}$ is hydrogen and $R^{11b}$ is methyl.

l. $R^{12a}$, $R^{12b}$, and $R^{13}$ Groups

In one aspect, each of $R^{12a}$, $R^{12b}$, and $R^{13}$, when present, is independently selected from hydrogen and C1-C4 alkyl. In a further aspect, each of $R^{12}$, $R^{12b}$, and $R^{13}$, when present, is independently selected from hydrogen, methyl, ethyl, n-propyl, and iso-propyl. In a still further aspect, each of $R^{12a}$, $R^{12b}$, and $R^{13}$, when present, is independently selected from hydrogen, methyl, and ethyl. In yet a further aspect, each of $R^{12}$, $R^{12b}$, and $R^{13}$, when present, is independently selected from hydrogen and ethyl. In an even further aspect, each of $R^{12}$, $R^{12b}$, and $R^{13}$, when present, is independently selected from hydrogen and methyl. In a still further aspect, each of $R^{12a}$, $R^{12b}$, and $R^{13}$, when present, is hydrogen.

In a further aspect, each of $R^{12}$, $R^{12b}$, and $R^{13}$, when present, is independently selected from C1-C4 alkyl. In a still further aspect, each of $R^{12}$, $R^{12b}$, and $R^{13}$, when present, is independently selected from methyl, ethyl, n-propyl, and iso-propyl. In yet a further aspect, each of $R^1$, $R^{12b}$, and $R^{13}$, when present, is independently selected from methyl and ethyl. In an even further aspect, each of $R^{12a}$, $R^{12b}$, and $R^{13}$, when present, is ethyl. In a still further aspect, each of $R^{12a}$, $R^{12b}$, and $R^{13}$, when present, is methyl.

In a further aspect, $R^{12a}$, when present, is hydrogen and $R^{12b}$, when present, is C1-C4 alkyl. In a still further aspect, $R^{12a}$, when present, is hydrogen and $R^{12b}$, when present, is selected from methyl, ethyl, n-propyl, and iso-propyl. In yet a further aspect, $R^{12a}$, when present, is hydrogen and $R^{12b}$, when present, is selected from methyl and ethyl. In an even further aspect, $R^{12a}$, when present, is hydrogen and $R^{12b}$, when present, is ethyl. In a still further aspect, $R^{12a}$a when present, is hydrogen and $R^{12b}$, when present, is methyl.

m. $R^4$ Groups

In one aspect, each occurrence of $R^{14}$ is independently selected from hydrogen, halogen, C1-C8 alkyl, C1-C8 alkoxy, and —C(═O)NR$^{3a}$R$^{3b}$. In a further aspect, each occurrence of $R^{14}$ is independently selected from hydrogen, halogen, C1-C4 alkyl, C1-C4 alkoxy, and —C(═O)NR$^{3a}$R$^{3b}$. In a still further aspect, each occurrence of $R^{14}$ is independently selected from hydrogen, fluorine, chlorine, methyl, ethyl, n-propyl, iso-propyl, —$OCH_3$, —$OCH_2CH_3$, —$OCH_2CH_2CH_3$, —$OCH(CH_3)_2$, and —C(═O)NR$^{3a}$R$^{3b}$. In yet a further aspect, each occurrence of $R^{14}$ is independently selected from hydrogen, fluorine, chlorine, methyl, ethyl, —$OCH_3$, —$OCH_2CH_3$, and —C(═O)NR$^{3a}$R$^{3b}$. In an even further aspect, each occurrence of $R^{14}$ is independently selected from hydrogen, fluorine, chlorine, methyl, —$OCH_3$, and —C(═O)NR$^{3a}$R$^{3b}$.

In a further aspect, each occurrence of $R^{14}$ is independently selected from hydrogen, C1-C8 alkyl, C1-C8 alkoxy, and —C(═O)NR$^{3a}$R$^{3b}$. In a still further aspect, each occurrence of $R^{14}$ is independently selected from hydrogen, C1-C4 alkyl, C1-C4 alkoxy, and —C(═O)$NR^{3a}R^{3b}$. In yet a further aspect, each occurrence of $R^{14}$ is independently selected from hydrogen, methyl, ethyl, n-propyl, iso-propyl, —$OCH_3$, —$OCH_2CH_3$, —$OCH_2CH_2CH_3$, —$OCH(CH_3)_2$, and —C(═O)$NR^{3a}R^{3b}$. In an even further aspect, each occurrence of $R^{14}$ is independently selected from hydrogen, methyl, ethyl, —$OCH_3$, —$OCH_2CH_3$, and —C(═O)$NR^{3a}R^{3b}$. In a still further aspect, each occurrence of $R^{14}$ is independently selected from hydrogen, methyl, —$OCH_3$, and —C(═O)$NR^{3a}R^{3b}$.

In a further aspect, each occurrence of $R^{14}$ is independently selected from hydrogen, C1-C8 alkyl, and C1-C8 alkoxy. In a still further aspect, each occurrence of $R^{14}$ is independently selected from hydrogen, C1-C4 alkyl, and C1-C4 alkoxy. In yet a further aspect, each occurrence of $R^{14}$ is independently selected from hydrogen, methyl, ethyl, n-propyl, iso-propyl, —$OCH_3$, —$OCH_2CH_3$, —$OCH_2CH_2CH_3$, and —$OCH(CH_3)_2$. In an even further aspect, each occurrence of $R^{14}$ is independently selected from hydrogen, methyl, ethyl, —$OCH_3$, and —$OCH_2CH_3$. In a still further aspect, each occurrence of $R^{14}$ is independently selected from hydrogen, methyl, and —$OCH_3$.

In a further aspect, each occurrence of $R^{14}$ is independently selected from hydrogen and halogen. In a still further aspect, each occurrence of $R^{14}$ is independently selected from hydrogen, fluorine, and chlorine. In yet a further aspect, each occurrence of $R^{14}$ is independently selected from hydrogen and chlorine. In a still further aspect, each occurrence of $R^{14}$ is independently selected from hydrogen and fluorine. In yet a further aspect, each occurrence of $R^{14}$ is hydrogen.

n. $Ar^1$ Groups

In one aspect, $Ar^1$ is a 3- to 6-membered heterocycle substituted with 0, 1, 2, or 3 groups independently selected from halogen and C1-C8 alkyl. In a further aspect, $Ar^1$ is a 3- to 6-membered heterocycle substituted with 0, 1, 2, or 3 groups independently selected from halogen and C1-C4 alkyl.

In a further aspect, $Ar^1$ is a 3- to 6-membered heterocycle substituted with 0, 1, or 2 groups independently selected from halogen and C1-C8 alkyl. In a still further aspect, $Ar^1$ is a 3- to 6-membered heterocycle substituted with 0 or 1 group selected from halogen and C1-C8 alkyl. In yet a further aspect, $Ar^1$ is a 3- to 6-membered heterocycle monosubstituted with a group selected from halogen and C1-C8 alkyl. In an even further aspect, $Ar^1$ is a 3- to 6-membered unsubstituted heterocycle.

In a further aspect, $Ar^1$ is a 3- to 6-membered heterocycle substituted with 0, 1, 2, or 3 groups independently selected from fluorine, chlorine, and C1-C8 alkyl. In a still further aspect, $Ar^1$ is a 3- to 6-membered heterocycle substituted with 0, 1, 2, or 3 groups independently selected from fluorine, chlorine, methyl, ethyl, iso-propyl, n-propyl, iso-butyl, sec-butyl, n-butyl, and tert-butyl. In yet a further aspect, $Ar^1$ is a 3- to 6-membered heterocycle substituted with 0, 1, 2, or 3 groups independently selected from fluorine, chlorine, methyl, ethyl, iso-propyl, and n-propyl. In an even further aspect, $Ar^1$ is a 3- to 6-membered heterocycle substituted with 0, 1, 2, or 3 groups independently selected from fluorine, chlorine, methyl, and ethyl. In a still further aspect, $Ar^1$ is a 3- to 6-membered heterocycle substituted with 0, 1, 2, or 3 groups independently selected from fluorine, chlorine, and methyl.

In a further aspect, $Ar^1$ is a 3- to 6-membered nitrogen-containing heterocycle substituted with 0, 1, 2, or 3 groups independently selected from halogen and C1-C8 alkyl. In a still further aspect, $Ar^1$ is a 3- to 6-membered nitrogen-containing heterocycle substituted with 0, 1, or 2 groups independently selected from halogen and C1-C8 alkyl. In yet a further aspect, $Ar^1$ is a 3- to 6-membered nitrogen-containing heterocycle substituted with 0 or 1 group selected from halogen and C1-C8 alkyl. In an even further aspect, $Ar^1$ is a 3- to 6-membered nitrogen-containing heterocycle monosubstituted with a group selected from halogen and C1-C8 alkyl. In a still further aspect, $Ar^1$ is a 3- to 6-membered unsubstituted nitrogen-containing heterocycle.

In a further aspect, $Ar^1$ is a 3- to 6-membered nitrogen-containing heterocycle substituted with 0, 1, 2, or 3 groups independently selected from fluorine, chlorine, and C1-C8 alkyl. In a still further aspect, $Ar^1$ is a 3- to 6-membered nitrogen-containing heterocycle substituted with 0, 1, 2, or 3 groups independently selected from fluorine, chlorine, methyl, ethyl, iso-propyl, n-propyl, iso-butyl, sec-butyl, n-butyl, and tert-butyl. In yet a further aspect, $Ar^1$ is a 3- to 6-membered nitrogen-containing heterocycle substituted with 0, 1, 2, or 3 groups independently selected from fluorine, chlorine, methyl, ethyl, iso-propyl, and n-propyl. In an even further aspect, $Ar^1$ is a 3- to 6-membered nitrogen-containing heterocycle substituted with 0, 1, 2, or 3 groups independently selected from fluorine, chlorine, methyl, and ethyl. In a still further aspect, $Ar^1$ is a 3- to 6-membered nitrogen-containing heterocycle substituted with 0, 1, 2, or 3 groups independently selected from fluorine, chlorine, and methyl.

In a further aspect, $Ar^1$ is a 3-membered heterocycle substituted with 0, 1, 2, or 3 groups independently selected from halogen and C1-C8 alkyl. In a still further aspect, $Ar^1$ is a 3-membered heterocycle substituted with 0, 1, or 2 groups independently selected from halogen and C1-C8 alkyl. In yet a further aspect, $Ar^1$ is a 3-membered heterocycle substituted with 0 or 1 group selected from halogen and C1-C8 alkyl. In an even further aspect, $Ar^1$ is a 3-membered heterocycle monosubstituted with a group selected from halogen and C1-C8 alkyl. In a still further aspect, $Ar^1$ is a 3-membered unsubstituted heterocycle.

In a further aspect, $Ar^1$ is a 3-membered heterocycle substituted with 0, 1, 2, or 3 groups independently selected from fluorine, chlorine, and C1-C8 alkyl. In a still further aspect, $Ar^1$ is a 3-membered heterocycle substituted with 0, 1, 2, or 3 groups independently selected from fluorine, chlorine, methyl, ethyl, iso-propyl, n-propyl, iso-butyl, sec-butyl, n-butyl, and tert-butyl. In yet a further aspect, $Ar^1$ is a 3-membered heterocycle substituted with 0, 1, 2, or 3 groups independently selected from fluorine, chlorine, methyl, ethyl, iso-propyl, and n-propyl. In an even further aspect, $Ar^1$ is a 3-membered heterocycle substituted with 0, 1, 2, or 3 groups independently selected from fluorine, chlorine, methyl, and ethyl. In a still further aspect, $Ar^1$ is a 3-membered heterocycle substituted with 0, 1, 2, or 3 groups independently selected from fluorine, chlorine, and methyl.

In a further aspect, $Ar^1$ is a 4-membered heterocycle substituted with 0, 1, 2, or 3 groups independently selected from halogen and C1-C8 alkyl. In a still further aspect, $Ar^1$ is a 4-membered heterocycle substituted with 0, 1, or 2 groups independently selected from halogen and C1-C8 alkyl. In yet a further aspect, $Ar^1$ is a 4-membered heterocycle substituted with 0 or 1 group selected from halogen and C1-C8 alkyl. In an even further aspect, $Ar^1$ is a 4-membered heterocycle monosubstituted with a group selected from halogen and C1-C8 alkyl. In a still further aspect, $Ar^1$ is a 4-membered unsubstituted heterocycle.

In a further aspect, $Ar^1$ is a 4-membered heterocycle substituted with 0, 1, 2, or 3 groups independently selected from fluorine, chlorine, and C1-C8 alkyl. In a still further aspect, $Ar^1$ is a 4-membered heterocycle substituted with 0, 1, 2, or 3 groups independently selected from fluorine, chlorine, methyl, ethyl, iso-propyl, n-propyl, iso-butyl, sec-butyl, n-butyl, and tert-butyl. In yet a further aspect, $Ar^1$ is a 4-membered heterocycle substituted with 0, 1, 2, or 3 groups independently selected from fluorine, chlorine, methyl, ethyl, iso-propyl, and n-propyl. In an even further aspect, $Ar^1$ is a 4-membered heterocycle substituted with 0, 1, 2, or 3 groups independently selected from fluorine, chlorine, methyl, and ethyl. In a still further aspect, $Ar^1$ is a 4-membered heterocycle substituted with 0, 1, 2, or 3 groups independently selected from fluorine, chlorine, and methyl.

In a further aspect, $Ar^1$ is a 5-membered heterocycle substituted with 0, 1, 2, or 3 groups independently selected from halogen and C1-C8 alkyl. In a still further aspect, $Ar^1$ is a 5-membered heterocycle substituted with 0, 1, or 2 groups independently selected from halogen and C1-C8 alkyl. In yet a further aspect, $Ar^1$ is a 5-membered heterocycle substituted with 0 or 1 group selected from halogen and C1-C8 alkyl. In an even further aspect, $Ar^1$ is a 5-membered heterocycle monosubstituted with a group selected from halogen and C1-C8 alkyl. In a still further aspect, $Ar^1$ is a 5-membered unsubstituted heterocycle.

In a further aspect, $Ar^1$ is a 5-membered heterocycle substituted with 0, 1, 2, or 3 groups independently selected from fluorine, chlorine, and C1-C8 alkyl. In a still further aspect, $Ar^1$ is a 5-membered heterocycle substituted with 0, 1, 2, or 3 groups independently selected from fluorine, chlorine, methyl, ethyl, iso-propyl, n-propyl, iso-butyl, sec-butyl, n-butyl, and tert-butyl. In yet a further aspect, $Ar^1$ is a 5-membered heterocycle substituted with 0, 1, 2, or 3 groups independently selected from fluorine, chlorine, methyl, ethyl, iso-propyl, and n-propyl. In an even further aspect, $Ar^1$ is a 5-membered heterocycle substituted with 0, 1, 2, or 3 groups independently selected from fluorine, chlorine, methyl, and ethyl. In a still further aspect, $Ar^1$ is a 5-membered heterocycle substituted with 0, 1, 2, or 3 groups independently selected from fluorine, chlorine, and methyl.

In a further aspect, $Ar^1$ is a 6-membered heterocycle substituted with 0, 1, 2, or 3 groups independently selected from halogen and C1-C8 alkyl. In a still further aspect, $Ar^1$ is a 6-membered heterocycle substituted with 0, 1, or 2 groups independently selected from halogen and C1-C8 alkyl. In yet a further aspect, $Ar^1$ is a 6-membered heterocycle substituted with 0 or 1 group selected from halogen and C1-C8 alkyl. In an even further aspect, $Ar^1$ is a 6-membered heterocycle monosubstituted with a group selected from halogen and C1-C8 alkyl. In a still further aspect, $Ar^1$ is a 6-membered unsubstituted heterocycle.

In a further aspect, $Ar^1$ is a 6-membered heterocycle substituted with 0, 1, 2, or 3 groups independently selected from fluorine, chlorine, and C1-C8 alkyl. In a still further aspect, $Ar^1$ is a 6-membered heterocycle substituted with 0, 1, 2, or 3 groups independently selected from fluorine, chlorine, methyl, ethyl, iso-propyl, n-propyl, iso-butyl, sec-butyl, n-butyl, and tert-butyl. In yet a further aspect, $Ar^1$ is a 6-membered heterocycle substituted with 0, 1, 2, or 3 groups independently selected from fluorine, chlorine, methyl, ethyl, iso-propyl, and n-propyl. In an even further aspect, $Ar^1$ is a 6-membered heterocycle substituted with 0, 1, 2, or 3 groups independently selected from fluorine, chlorine, methyl, and ethyl. In a still further aspect, $Ar^1$ is a 6-membered heterocycle substituted with 0, 1, 2, or 3 groups independently selected from fluorine, chlorine, and methyl.

In a further aspect, $Ar^1$ is pyrazole substituted with 0, 1, 2, or 3 groups independently selected from halogen and C1-C8 alkyl. In a still further aspect, $Ar^1$ is a 3- to 6-membered nitrogen-containing heterocycle substituted with 0, 1, or 2 groups independently selected from halogen and C1-C8 alkyl. In yet a further aspect, $Ar^1$ is pyrazole substituted with 0 or 1 group selected from halogen and C1-C8 alkyl. In an even further aspect, $Ar^1$ is pyrazole monosubstituted with a group selected from halogen and C1-C8 alkyl. In a still further aspect, $Ar^1$ is unsubstituted pyrazole.

In a further aspect, $Ar^1$ is pyrazole substituted with 0, 1, 2, or 3 groups independently selected from fluorine, chlorine, and C1-C8 alkyl. In a still further aspect, $Ar^1$ is pyrazole substituted with 0, 1, 2, or 3 groups independently selected from fluorine, chlorine, methyl, ethyl, iso-propyl, n-propyl, iso-butyl, sec-butyl, n-butyl, and tert-butyl. In yet a further aspect, $Ar^1$ is pyrazole substituted with 0, 1, 2, or 3 groups independently selected from fluorine, chlorine, methyl, ethyl, iso-propyl, and n-propyl. In an even further aspect, $Ar^1$ is pyrazole substituted with 0, 1, 2, or 3 groups independently selected from fluorine, chlorine, methyl, and ethyl. In a still further aspect, $Ar^1$ is pyrazole substituted with 0, 1, 2, or 3 groups independently selected from fluorine, chlorine, and methyl.

In a further aspect, $Ar^1$ is triazole substituted with 0, 1, 2, or 3 groups independently selected from halogen and C1-C8 alkyl. In a still further aspect, $Ar^1$ is a 3- to 6-membered nitrogen-containing heterocycle substituted with 0, 1, or 2 groups independently selected from halogen and C1-C8 alkyl. In yet a further aspect, $Ar^1$ is triazole substituted with 0 or 1 group selected from halogen and C1-C8 alkyl. In an even further aspect, $Ar^1$ is triazole monosubstituted with a group selected from halogen and C1-C8 alkyl. In a still further aspect, $Ar^1$ is unsubstituted triazole.

In a further aspect, $Ar^1$ is triazole substituted with 0, 1, 2, or 3 groups independently selected from fluorine, chlorine, and C1-C8 alkyl. In a still further aspect, $Ar^1$ is triazole substituted with 0, 1, 2, or 3 groups independently selected from fluorine, chlorine, methyl, ethyl, iso-propyl, n-propyl, iso-butyl, sec-butyl, n-butyl, and tert-butyl. In yet a further aspect, $Ar^1$ is triazole substituted with 0, 1, 2, or 3 groups independently selected from fluorine, chlorine, methyl, ethyl, iso-propyl, and n-propyl. In an even further aspect, $Ar^1$ is triazole substituted with 0, 1, 2, or 3 groups independently selected from fluorine, chlorine, methyl, and ethyl. In a still further aspect, $Ar^1$ is triazole substituted with 0, 1, 2, or 3 groups independently selected from fluorine, chlorine, and methyl.

o. $Ar^2$ Groups

In one aspect, $Ar^2$ is selected from aryl and heteroaryl and substituted with 0, 1, 2, or 3 groups independently selected from halogen and C1-C8 alkyl. In a further aspect, $Ar^2$ is selected from aryl and heteroaryl and substituted with 0, 1, 2, or 3 groups independently selected from halogen and C1-C4 alkyl.

In a further aspect, $Ar^2$ is selected from aryl and heteroaryl and substituted with 0, 1, 2, or 3 groups independently selected from halogen, —$NH_2$, C1-C8 alkyl, C1-C8 alkylamino, (C1-C8)(C1-C8) dialkylamino, C1-C8 aminoalkyl, and —$N(CO_2(C1\text{-}C8\ alkyl))_2$. In a still further aspect, $Ar^2$ is selected from aryl and heteroaryl and substituted with 0, 1, 2, or 3 groups independently selected from halogen, —$NH_2$, C1-C4 alkyl, C1-C4 alkylamino, (C1-C4)(C1-C4) dialkylamino, C1-C4 aminoalkyl, and —$N(CO_2(C1\text{-}C4\ alkyl))_2$.

In a further aspect, $Ar^2$ is selected from aryl and heteroaryl and substituted with 0, 1, 2, or 3 groups independently selected from —$NH_2$, C1-C8 alkylamino, (C1-C8)(C1-C8) dialkylamino, C1-C8 aminoalkyl, and —$N(CO_2(C1\text{-}C8\ alkyl))_2$. In a still further aspect, $Ar^2$ is selected from aryl and heteroaryl and substituted with 0, 1, 2, or 3 groups independently selected from $-NH_2$, C1-C4 alkylamino, (C1-C4)(C1-C4) dialkylamino, C1-C4 aminoalkyl, and $-N(CO_2(C1\text{-}C4\ alkyl))_2$. In yet a further aspect, $Ar^2$ is selected from aryl and heteroaryl and substituted with 0, 1, 2, or 3 groups independently selected from $-NH_2$, $-NHCH_3$, $-NHCH_2CH_3$, $-NHCH_2CH_2CH_3$, $-NHCH(CH_3)_2$, $-N(CH_3)_2$, $-N(CH_3)(CH_2CH_3)$, $-N(CH_3)(CH_2CH_2CH_3)$, $-N(CH_3)(CH(CH_3)_2)$, $-N(CH_2CH_3)_2$, $-N(CH_2CH_3)(CH_2CH_2CH_3)$, $-N(CH_2CH_3)(CH(CH_3)_2)$, $-N(CH_2CH_2CH_3)_2$, $-N(CH_2CH_2CH_3)(CH(CH_3)_2)$, $-N(CH(CH_3)_2)_2$, $-CH_2NH_2$, $-CH_2CH_2NH_2$, $-CH_2CH(CO_2CH_3)NHCO_2C(CH_3)_3$, $-N(CO_2CH_3)_2$, $-N(CO_2CH_2CH_3)_2$, $-N(CO_2CH_2CH_2CH_3)_2$, $-N(CO_2CH(CH_3)_2)_2$, and $-N(CO_2C(CH_3)_3)_2$.

In a further aspect, $Ar^2$ is selected from aryl and heteroaryl and substituted with 0, 1, or 2 groups independently selected from halogen and C1-C8 alkyl. In a still further aspect, $Ar^2$ is selected from aryl and heteroaryl and substituted with 0 or 1 group selected from halogen and C1-C8 alkyl. In yet a further aspect, $Ar^2$ is selected from aryl and heteroaryl and monosubstituted with a group selected from halogen and C1-C8 alkyl. In an even further aspect, $Ar^2$ is selected from aryl and heteroaryl and is unsubstituted.

In a further aspect, $Ar^2$ is selected from aryl and heteroaryl and substituted with 0, 1, 2, or 3 groups independently selected from fluorine, chlorine, and C1-C8 alkyl. In a still further aspect, $Ar^2$ is selected from aryl and heteroaryl and substituted with 0, 1, 2, or 3 groups independently selected from fluorine, chlorine, methyl, ethyl, iso-propyl, n-propyl, iso-butyl, sec-butyl, n-butyl, and tert-butyl. In yet a further aspect, $Ar^2$ is selected from aryl and heteroaryl and substituted with 0, 1, 2, or 3 groups independently selected from fluorine, chlorine, methyl, ethyl, iso-propyl, and n-propyl. In an even further aspect, $Ar^2$ is selected from aryl and heteroaryl and substituted with 0, 1, 2, or 3 groups independently selected from fluorine, chlorine, methyl, and ethyl. In a still further aspect, $Ar^2$ is selected from aryl and heteroaryl and substituted with 0, 1, 2, or 3 groups independently selected from fluorine, chlorine, and methyl.

In a further aspect, $Ar^2$ is aryl substituted with 0, 1, 2, or 3 groups independently selected from halogen and C1-C8 alkyl. In a still further aspect, $Ar^2$ is aryl substituted with 0, 1, or 2 groups independently selected from halogen and C1-C8 alkyl. In yet a further aspect, $Ar^2$ is aryl substituted with 0 or 1 group selected from halogen and C1-C8 alkyl. In an even further aspect, $Ar^2$ is aryl monosubstituted with a group selected from halogen and C1-C8 alkyl. In a still further aspect, $Ar^2$ is unsubstituted aryl.

In a further aspect, $Ar^2$ is aryl substituted with 0, 1, 2, or 3 groups independently selected from fluorine, chlorine, and C1-C8 alkyl. In a still further aspect, $Ar^2$ is aryl substituted with 0, 1, 2, or 3 groups independently selected from fluorine, chlorine, methyl, ethyl, iso-propyl, n-propyl, iso-butyl, sec-butyl, n-butyl, and tert-butyl. In yet a further aspect, $Ar^2$ is aryl substituted with 0, 1, 2, or 3 groups independently selected from fluorine, chlorine, methyl, ethyl, iso-propyl, and n-propyl. In an even further aspect, $Ar^2$ is aryl substituted with 0, 1, 2, or 3 groups independently selected from fluorine, chlorine, methyl, and ethyl. In a still further aspect, $Ar^2$ is aryl substituted with 0, 1, 2, or 3 groups independently selected from fluorine, chlorine, and methyl.

In a further aspect, $Ar^2$ is phenyl substituted with 0, 1, 2, or 3 groups independently selected from halogen and C1-C8 alkyl. In a still further aspect, $Ar^2$ is phenyl substituted with 0, 1, or 2 groups independently selected from halogen and C1-C8 alkyl. In yet a further aspect, $Ar^2$ is phenyl substituted with 0 or 1 group selected from halogen and C1-C8 alkyl. In an even further aspect, $Ar^2$ is phenyl monosubstituted with a group selected from halogen and C1-C8 alkyl. In a still further aspect, $Ar^2$ is unsubstituted phenyl.

In a further aspect, $Ar^2$ is phenyl substituted with 0, 1, 2, or 3 groups independently selected from fluorine, chlorine, and C1-C8 alkyl. In a still further aspect, $Ar^2$ is phenyl substituted with 0, 1, 2, or 3 groups independently selected from fluorine, chlorine, methyl, ethyl, iso-propyl, n-propyl, iso-butyl, sec-butyl, n-butyl, and tert-butyl. In yet a further aspect, $Ar^2$ is phenyl substituted with 0, 1, 2, or 3 groups independently selected from fluorine, chlorine, methyl, ethyl, iso-propyl, and n-propyl. In an even further aspect, $Ar^2$ is phenyl substituted with 0, 1, 2, or 3 groups independently selected from fluorine, chlorine, methyl, and ethyl. In a still further aspect, $Ar^2$ is phenyl substituted with 0, 1, 2, or 3 groups independently selected from fluorine, chlorine, and methyl.

In a further aspect, $Ar^2$ is heteroaryl substituted with 0, 1, 2, or 3 groups independently selected from halogen and C1-C8 alkyl. In a still further aspect, $Ar^2$ is heteroaryl substituted with 0, 1, or 2 groups independently selected from halogen and C1-C8 alkyl. In yet a further aspect, $Ar^2$ is heteroaryl substituted with 0 or 1 group selected from halogen and C1-C8 alkyl. In an even further aspect, $Ar^2$ is heteroaryl monosubstituted with a group selected from halogen and C1-C8 alkyl. In a still further aspect, $Ar^2$ is unsubstituted heteroaryl.

In a further aspect, $Ar^2$ is heteroaryl substituted with 0, 1, 2, or 3 groups independently selected from fluorine, chlorine, and C1-C8 alkyl. In a still further aspect, $Ar^2$ is heteroaryl substituted with 0, 1, 2, or 3 groups independently selected from fluorine, chlorine, methyl, ethyl, iso-propyl, n-propyl, iso-butyl, sec-butyl, n-butyl, and tert-butyl. In yet a further aspect, $Ar^2$ is heteroaryl substituted with 0, 1, 2, or 3 groups independently selected from fluorine, chlorine, methyl, ethyl, iso-propyl, and n-propyl. In an even further aspect, $Ar^2$ is heteroaryl substituted with 0, 1, 2, or 3 groups independently selected from fluorine, chlorine, methyl, and ethyl. In a still further aspect, $Ar^2$ is heteroaryl substituted with 0, 1, 2, or 3 groups independently selected from fluorine, chlorine, and methyl.

In a further aspect, $Ar^2$ is pyridinyl substituted with 0, 1, 2, or 3 groups independently selected from halogen and C1-C8 alkyl. In a still further aspect, $Ar^2$ is pyridinyl substituted with 0, 1, or 2 groups independently selected from halogen and C1-C8 alkyl. In yet a further aspect, $Ar^2$ is pyridinyl substituted with 0 or 1 group selected from halogen and C1-C8 alkyl. In an even further aspect, $Ar^2$ is pyridinyl monosubstituted with a group selected from halogen and C1-C8 alkyl. In a still further aspect, $Ar^2$ is unsubstituted pyridinyl.

In a further aspect, $Ar^2$ is pyridinyl substituted with 0, 1, 2, or 3 groups independently selected from fluorine, chlorine, and C1-C8 alkyl. In a still further aspect, $Ar^2$ is pyridinyl substituted with 0, 1, 2, or 3 groups independently selected from fluorine, chlorine, methyl, ethyl, iso-propyl, n-propyl, iso-butyl, sec-butyl, n-butyl, and tert-butyl. In yet a further aspect, $Ar^2$ is pyridinyl substituted with 0, 1, 2, or 3 groups independently selected from fluorine, chlorine, methyl, ethyl, iso-propyl, and n-propyl. In an even further aspect, $Ar^2$ is pyridinyl substituted with 0, 1, 2, or 3 groups independently selected from fluorine, chlorine, methyl, and ethyl. In a still further aspect, $Ar^2$ is pyridinyl substituted with 0, 1, 2, or 3 groups independently selected from fluorine, chlorine, and methyl.

In a further aspect, $Ar^2$ is a purine substituted with 0, 1, 2, or 3 groups independently selected from halogen, $-NH_2$, C1-C8 alkyl, C1-C8 alkylamino, (C1-C8)(C1-C8) dialkylamino, C1-C8 aminoalkyl, and —$N(CO_2$(C1-C8 alkyl$))_2$. In a still further aspect, $Ar^2$ is a purine substituted with 0, 1, or 2 groups independently selected from halogen, —$NH_2$, C1-C8 alkyl, C1-C8 alkylamino, (C1-C8)(C1-C8) dialkylamino, C1-C8 aminoalkyl, and —$N(CO_2$(C1-C8 alkyl$))_2$. In yet a further aspect, $Ar^2$ is a purine substituted with 0 or 1 group selected from halogen, —$NH_2$, C1-C8 alkyl, C1-C8 alkylamino, (C1-C8)(C1-C8) dialkylamino, C1-C8 aminoalkyl, and —$N(CO_2$(C1-C8 alkyl$))_2$. In an even further aspect, $Ar^2$ is a purine monosubstituted with a group selected from halogen, —$NH_2$, C1-C8 alkyl, C1-C8 alkylamino, (C1-C8)(C1-C8) dialkylamino, C1-C8 aminoalkyl, and —$N(CO_2$(C1-C8 alkyl$))_2$. In a still further aspect, $Ar^2$ is an unsubstituted purine.

In a further aspect, $Ar^2$ is a purine substituted with 0, 1, 2, or 3 groups independently selected from fluorine, chlorine, —$NH_2$, C1-C8 alkyl, C1-C8 alkylamino, (C1-C8)(C1-C8) dialkylamino, C1-C8 aminoalkyl, and —$N(CO_2$(C1-C8 alkyl$))_2$. In a still further aspect, $Ar^2$ is a purine substituted with 0, 1, 2, or 3 groups independently selected from fluorine, chlorine, methyl, ethyl, iso-propyl, n-propyl, isobutyl, sec-butyl, n-butyl, tert-butyl, —$NH_2$, C1-C4 alkylamino, (C1-C4)(C1-C4) dialkylamino, C1-C4 aminoalkyl, and —$N(CO_2$(C1-C4 alkyl$))_2$. In yet a further aspect, $Ar^2$ is a purine substituted with 0, 1, 2, or 3 groups independently selected from fluorine, chlorine, methyl, ethyl, iso-propyl, n-propyl, —$NH_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, —$N(CH(CH_3)_2)_2$, —$CH_2NH_2$, —$CH_2CH_2NH_2$, —$CH_2CH(CO_2CH_3)NHCO_2C(CH_3)_3$, —$N(CO_2CH_3)_2$, —$N(CO_2CH_2CH_3)_2$, —$N(CO_2CH_2CH_2CH_3)_2$, —$N(CO_2CH(CH_3)_2)_2$, and —$N(CO_2C(CH_3)_3)_2$. In an even further aspect, $Ar^2$ is a purine substituted with 0, 1, 2, or 3 groups independently selected from fluorine, chlorine, methyl, ethyl, —$NH_2$, —$NHCH_3$, —$NHCH_2CH_3$, —$N(CH_3)_2$, —$N(CH_3)(CH_2CH_3)$, —$N(CH_2CH_3)_2$, —$CH_2NH_2$, —$CH_2CH_2NH_2$, —$CH_2CH(CO_2CH_3)NHCO_2C(CH_3)_3$, —$N(CO_2CH_3)_2$, —$N(CO_2CH_2CH_3)_2$, and —$N(CO_2C(CH_3)_3)_2$. In a still further aspect, $Ar^2$ is a purine substituted with 0, 1, 2, or 3 groups independently selected from fluorine, chlorine, methyl, —$NH_2$, —$NHCH_3$, —$N(CH_3)_2$, —$CH_2NH_2$, —$CH_2CH(CO_2CH_3)NHCO_2C(CH_3)_3$, and —$N(CO_2C(CH_3)_3)_2$.

2. Example Structures

In one aspect, a compound can be present as:

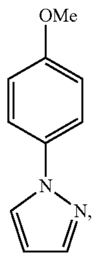
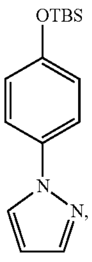
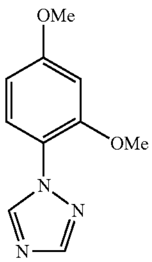
,

-continued

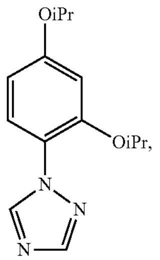
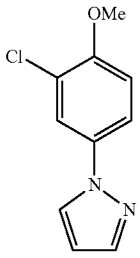
,
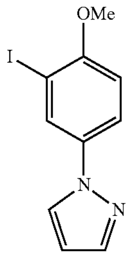
,

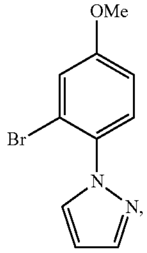
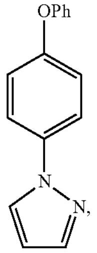
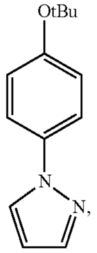
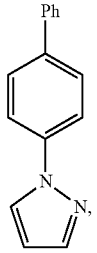

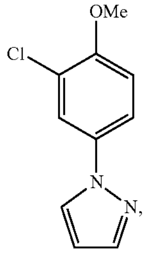
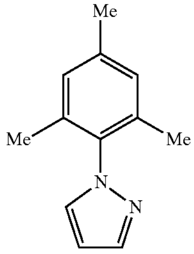
,
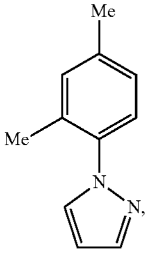

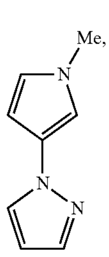
,
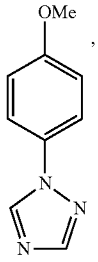
,
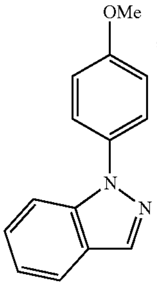
,
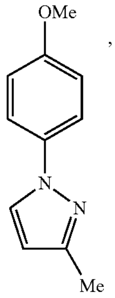

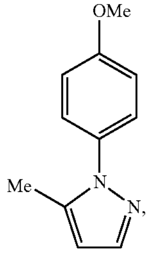
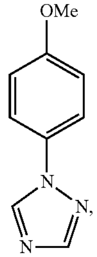
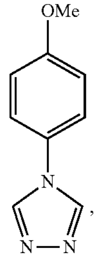
,

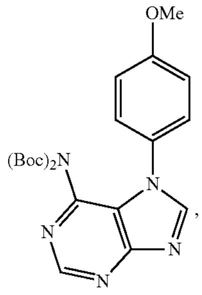
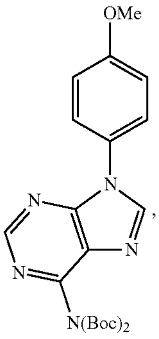

-continued

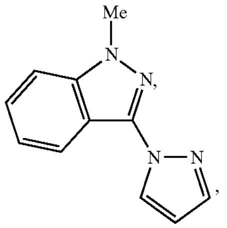

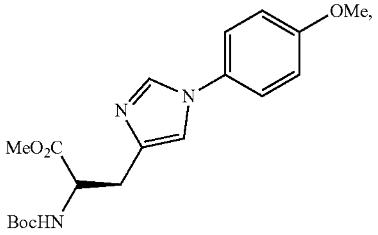

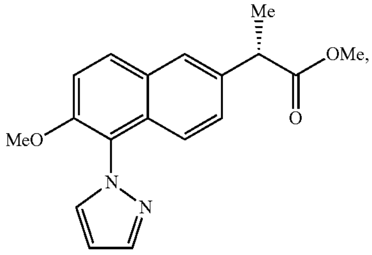

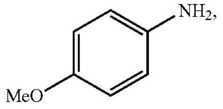

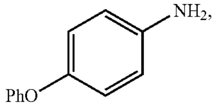

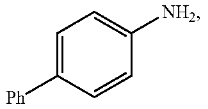

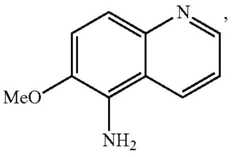

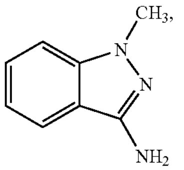

or

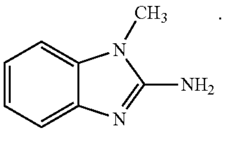

.

E. ACRIDINIUM PHOTOCATALYSTS

In one aspect, acridinium photocatalysts are disclosed. It is contemplated that each disclosed derivative can be optionally further substituted. It is also contemplated that any one or more derivative can be optionally omitted from the invention. It is understood that a disclosed compound can be provided by the disclosed methods.

1. Structure

In one aspect, disclosed are acridinium photocatalysts having a structure represented by a formula:

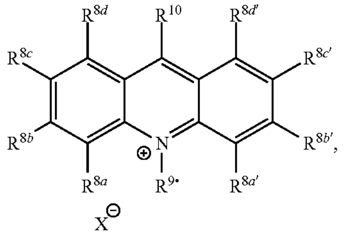

wherein X is selected from $BF_4$, TfO, $PF_6$, and $ClO_4$; wherein each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino, and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; wherein $R^9$ is selected from C1-C4 alkyl and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; and wherein $R^{10}$ is selected from C1-C4 alkyl and phenyl substituted with 0, 1, 2, or 3 groups independently selected from halogen and C1-C4 alkyl.

In a further aspect, the acridinium photocatalyst has a structure selected from:

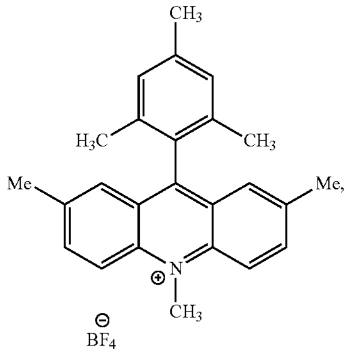

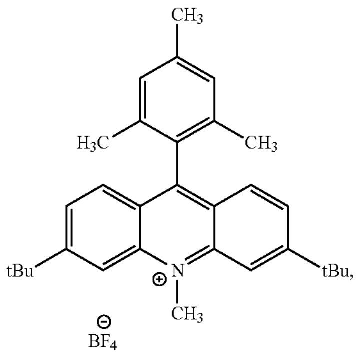

-continued

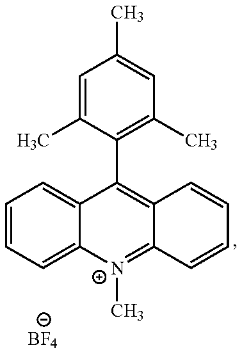
,

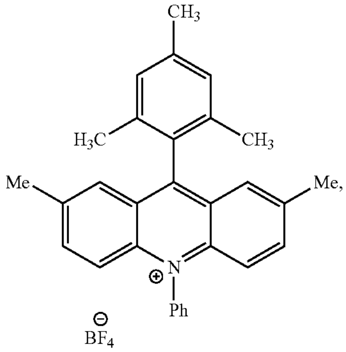
,

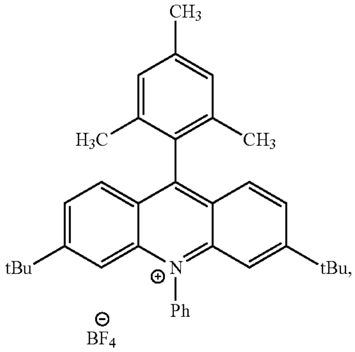
, and

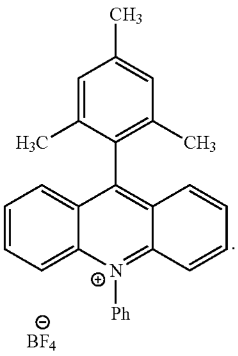
.

In a further aspect, the acridinium photocatalyst has a structure:

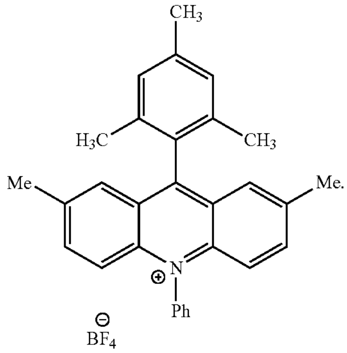
.

a. X Groups

In one aspect, X is selected from $BF_4$, TfO, $PF_6$, and $ClO_4$. In a further aspect, X is selected from $BF_4$, TfO, and $PF_6$. In a still further aspect, X is selected from $BF_4$ and $PF_6$. In yet a further aspect, X is $ClO_4$. In an even further aspect, X is TfO. In a still further aspect, X is $BF_4$. In yet a further aspect, X is $PF_6$.

b. $R^{8a}$, $R^{8b}$, $R^{8c}$, $R^{8d}$, $R^{8a'}$, $R^{8b'}$, $R^{8c'}$, and $R^{8d'}$ Groups In one aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino, and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino.

In a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino. In a still further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, methyl, ethyl, n-propyl, iso-propyl, —$OCH_3$, —$OCH_2CH_3$, —$OCH_2CH_2CH_3$, —$OCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In yet a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, methyl, ethyl, —$OCH_3$, —$OCH_2CH_3$, —$OCH(CH_3)_2$, —$NHCH_3$, —$N(CH_3)_2$, —$N(CH_3)(CH_2CH_3)$, and —$N(CH_2CH_3)_2$. In an even further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, methyl, —$OCH_3$, —$OCH(CH_3)_2$, —$NHCH_3$, and —$N(CH_3)_2$.

In a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, C1-C4 alkyl, C1-C4 alkoxy, C1-C4 alkylamino, C1-C4 dialkylamino. In a still further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, methyl, ethyl, n-propyl, iso-propyl, —$OCH_3$, —$OCH_2CH_3$, —$OCH_2CH_2CH_3$, —$OCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In yet a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, methyl, ethyl, —$OCH_3$, —$OCH_2CH_3$, —$OCH(CH_3)_2$, —$NHCH_3$, —$N(CH_3)_2$, —$N(CH_3)(CH_2CH_3)$, and —$N(CH_2CH_3)_2$. In an even further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, methyl, —$OCH_3$, —$OCH(CH_3)_2$, —$NHCH_3$, and —$N(CH_3)_2$.

In a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and C1-C4 alkyl. In a still further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, methyl, ethyl, n-propyl, and iso-propyl. In yet a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, methyl, and ethyl. In an even further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and methyl.

In a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and halogen. In a still further aspect, each of $R^{8a}$, $R^{8b}$, $R^{8'}$, $R^{8d}$, $R^{8a'}$, $R^{8b'}$, $R^{8c'}$, and $R^{8d'}$ is independently selected from hydrogen, fluorine, and chlorine. In yet a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and fluorine. In an even further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and chlorine.

In a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino. In a still further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and phenyl substituted with 0, 1, or 2 groups independently selected from halogen, —$CF_3$, —$NH_2$, C1-C4 alkyl, C1-C4 alkoxy, C1-C4 alkylamino, (C1-C4)(C1-C4) dialkylamino. In yet a further aspect, each of $R^{8a}$, $R^{8b}$, $R^{8c}$, $R^{8d}$, $R^{8a'}$, $R^{8b'}$, $R^{8c}$, and $R^{8d'}$ is independently selected from hydrogen and phenyl substituted with 0 or 1 group selected from halogen, —$CF_3$, —$NH_2$, C1-C4 alkyl, C1-C4 alkoxy, C1-C4 alkylamino, (C1-C4)(C1-C4) dialkylamino. In an even further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and phenyl monosubstituted with a group selected from halogen, —$CF_3$, —$NH_2$, C1-C4 alkyl, C1-C4 alkoxy, C1-C4 alkylamino, (C1-C4)(C1-C4) dialkylamino. In a still further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and unsubstituted phenyl.

In a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and phenyl substituted with 0, 1, 2, or 3 groups independently selected from halogen, —$CF_3$, —$NH_2$, methyl, ethyl, n-propyl, iso-propyl, —$OCH_3$, —$OCH_2CH_3$, —$OCH_2CH_2CH_3$, —$OCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In a still further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and phenyl substituted with 0, 1, 2, or 3 groups independently selected from fluorine, chlorine, —$CF_3$, —$NH_2$, methyl, ethyl, —$OCH_3$, —$OCH_2CH_3$, —$NHCH_3$, —$NHCH_2CH_3$, —$N(CH_3)_2$, —$N(CH_3)(CH_2CH_3)$, and —$N(CH_2CH_3)_2$. In yet a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and phenyl substituted with 0, 1, 2, or 3 groups independently selected from fluorine, chlorine, —$CF_3$, —$NH_2$, methyl, —$OCH_3$, —$NHCH_3$, and —$N(CH_3)_2$.

c. $R^9$ Groups

In one aspect, $R^9$ is selected from C1-C4 alkyl and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino.

In a further aspect, $R^9$ is C1-C4 alkyl. In a still further aspect, $R^9$ is selected from methyl, ethyl, n-propyl, and iso-propyl. In yet a further aspect, $R^9$ is selected from methyl and ethyl. In an even further aspect, $R^9$ is ethyl. In a still further aspect, $R^9$ is methyl.

In a further aspect, $R^9$ is phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino. In a still further aspect, $R^9$ is phenyl substituted with 0, 1, or 2 groups independently selected from halogen, —$CF_3$, —$NH_2$, C1-C4 alkyl, C1-C4 alkoxy, C1-C4 alkylamino, (C1-C4)(C1-C4) dialkylamino. In yet a further aspect, $R^9$ is phenyl substituted with 0 or 1 group selected from halogen, —$CF_3$, —$NH_2$, C1-C4 alkyl, C1-C4 alkoxy, C1-C4 alkylamino, (C1-C4)(C1-C4) dialkylamino. In an even further aspect, $R^9$ is phenyl monosubstituted with a group selected from halogen, —$CF_3$, —$NH_2$, C1-C4 alkyl, C1-C4 alkoxy, C1-C4 alkylamino, (C1-C4)(C1-C4) dialkylamino. In a still further aspect, $R^9$ is unsubstituted phenyl.

In a further aspect, $R^9$ is phenyl substituted with 0, 1, 2, or 3 groups independently selected from fluorine, chlorine, —$CF_3$, —$NH_2$, methyl, ethyl, n-propyl, iso-propyl, —$OCH_3$, —$OCH_2CH_3$, —$OCH_2CH_2CH_3$, —$OCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In a still further aspect, $R^9$ is phenyl substituted with 0, 1, 2, or 3 groups independently selected from fluorine, chlorine, —$CF_3$, —$NH_2$, methyl, ethyl, —$OCH_3$, —$OCH_2CH_3$, —$OCH(CH_3)_2$, —$NHCH_3$, —$NHCH_2CH_3$, —$N(CH_3)_2$, —$N(CH_3)(CH_2CH_3)$, and —$N(CH_2CH_3)_2$. In yet a further aspect, $R^9$ is phenyl substituted with 0, 1, 2, or 3 groups independently selected from fluorine, chlorine, methyl, —$CF_3$, —$NH_2$, —$OCH_3$, —$NHCH_3$, and —$N(CH_3)_2$.

d. $R^{10}$ Groups

In one aspect, $R^{10}$ is selected from C1-C4 alkyl and phenyl substituted with 0, 1, 2, or 3 groups independently selected from halogen and C1-C4 alkyl.

In a further aspect, $R^{10}$ is C1-C4 alkyl. In a still further aspect, $R^{10}$ is selected from methyl, ethyl, n-propyl, and iso-propyl. In yet a further aspect, $R^{10}$ is selected from methyl and ethyl. In an even further aspect, $R^{10}$ is ethyl. In a still further aspect, $R^{10}$ is methyl.

In a further aspect, $R^{10}$ is phenyl substituted with 0, 1, 2, or 3 groups independently selected from halogen and C1-C4 alkyl. In a still further aspect, $R^{10}$ is phenyl substituted with 0, 1, or 2 groups independently selected from halogen and C1-C4 alkyl. In yet a further aspect, $R^{10}$ is phenyl substituted with 0 or 1 group selected from halogen and C1-C4 alkyl. In an even further aspect, $R^{10}$ is phenyl monosubstituted with a group selected from halogen and C1-C4 alkyl. In a still further aspect, $R^{10}$ is unsubstituted phenyl.

In a further aspect, $R^{10}$ is phenyl substituted with 0, 1, 2, or 3 groups independently selected from fluorine, chlorine, methyl, ethyl, n-propyl, iso-propyl, n-butyl, sec-butyl, iso-butyl, and tert-butyl. In a still further aspect, $R^{10}$ is phenyl substituted with 0, 1, 2, or 3 groups independently selected from fluorine, chlorine, methyl, ethyl, n-propyl, and iso-propyl. In yet a further aspect, $R^{10}$ is phenyl substituted with 0, 1, 2, or 3 groups independently selected from fluorine, chlorine, methyl, and ethyl. In an even further aspect, $R^{10}$ is phenyl substituted with 0, 1, 2, or 3 groups independently selected from fluorine, chlorine, and methyl.

In a further aspect, $R^{10}$ is phenyl substituted with 0, 1, 2, or 3 groups independently selected from methyl, ethyl, n-propyl, iso-propyl, n-butyl, sec-butyl, iso-butyl, and tert-butyl. In a still further aspect, $R^{10}$ is phenyl substituted with 0, 1, 2, or 3 groups independently selected from methyl, ethyl, n-propyl, and iso-propyl. In yet a further aspect, $R^{10}$ is phenyl substituted with 0, 1, 2, or 3 groups independently selected from methyl, and ethyl. In an even further aspect, $R^{10}$ is phenyl substituted with 0, 1, 2, or 3 methyl groups.

2. Example Photocatalyst Structures

In one aspect, an acridinium photocatalyst can be present as:

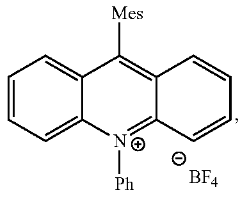

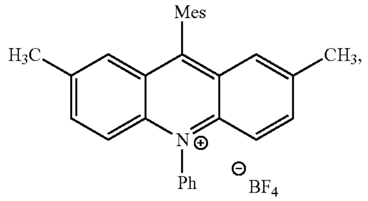

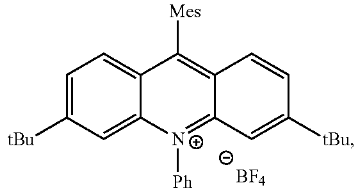

or

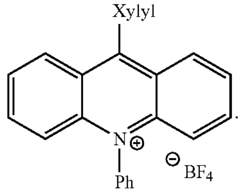

F. METHODS OF MAKING SUBSTITUTED ARENES

In one aspect, methods of making a compound having a structure represented by a formula:

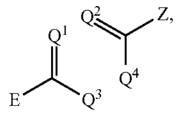

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; or wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; wherein Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —$NNR^4$, —OC(═O)$R^5$, and $Ar^1$; wherein $R^4$ is selected from hydrogen and C1-C8 alkyl; wherein $R^5$ is selected from C1-C8 alkyl; wherein $Ar^1$ is a 3- to 6-membered heterocycle substituted with 0, 1, 2, or 3 groups independently selected from halogen and C1-C8 alkyl, the method comprising the steps of: (a) reacting a compound having a structure represented by a formula:

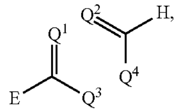

with a nucleophile selected from water, ammonia, a halide, a cyanide, an alcohol, a thiol, an amine, a hydrazine, a carbamate, a carboxylic acid, and an alkene, in the presence of a catalytically effective amount of an acridinium photocatalyst; and (b) reacting with an oxidant, thereby forming the compound are disclosed. In a further aspect, the electron donating group is selected from —OH, —SH, —$NH_2$, C1-C8 alkyl, C1-C8 alkoxy, C1-C8 thioalkoxy, C1-C8 silyloxy, C1-C8 alkylamino, (C1-C8)(C1-C8) dialkylamino, —OC(═O)$R^6$, —NHC(═O)$R^7$, —$OAr^2$, and $Ar^2$; wherein each of $R^6$ and $R^7$ is independently selected from C1-C8 alkyl; and wherein $Ar^2$ is selected from aryl and heteroaryl and substituted with 0, 1, 2, or 3 groups independently selected from halogen and C1-C8 alkyl. In a still further aspect, the electron donating group is selected from —OH, —SH, —$NH_2$, C1-C8 alkyl, C1-C8 alkoxy, C1-C8 thioalkoxy, C1-C8 alkylamino, (C1-C8)(C1-C8) dialkylamino, —OC(═O)$R^6$, —NHC(═O)$R^7$, and $Ar^2$; wherein each of $R^6$ and $R^7$ is independently selected from C1-C8 alkyl; and wherein $Ar^2$ is selected from aryl and heteroaryl and substituted with 0, 1, 2, or 3 groups independently selected from halogen and C1-C8 alkyl.

In one aspect, methods of making a compound having a structure represented by a formula:

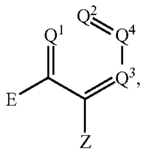

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; or wherein each of $Q^2$ and $Q^4$ is $CR^2$ and wherein each occurrence of $R^2$ are optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and —C(═O)$NR^{3a}R^{3b}$; wherein Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —$NNR^4$, —OC(═O)$R^5$, and $Ar^1$; wherein $R^4$ is selected from hydrogen and C1-C8 alkyl; wherein $R^5$ is selected from C1-C8 alkyl; wherein $Ar^1$ is a 3- to 6-membered heterocycle substituted with 0, 1, 2, or 3 groups independently selected from halogen and C1-C8 alkyl, the method comprising the steps of: (a) reacting a compound having a structure represented by a formula:

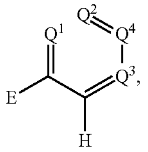

with a nucleophile selected from water, ammonia, a halide, a cyanide, an alcohol, a thiol, an amine, a hydrazine, a carbamate, a carboxylic acid, and an alkene, in the presence of a catalytically effective amount of an acridinium photocatalyst; and (b) reacting with an oxidant, thereby forming the compound are disclosed. In a further aspect, the electron donating group is selected from —OH, —SH, —$NH_2$, C1-C8 alkyl, C1-C8 alkoxy, C1-C8 thioalkoxy, C1-C8 silyloxy, C1-C8 alkylamino, (C1-C8)(C1-C8) dialkylamino, —OC(═O)$R^6$, —NHC(═O)$R^7$, —$OAr^2$, and $Ar^2$; wherein each of $R^6$ and $R^7$ is independently selected from C1-C8 alkyl; and wherein $Ar^2$ is selected from aryl and heteroaryl and substituted with 0, 1, 2, or 3 groups independently selected from halogen and C1-C8 alkyl. In a still further aspect, the electron donating group is selected from —OH, —SH, —$NH_2$, C1-C8 alkyl, C1-C8 alkoxy, C1-C8 thioalkoxy, C1-C8 alkylamino, (C1-C8)(C1-C8) dialkylamino, —OC(═O)$R^6$, —NHC(═O)$R^7$, and $Ar^2$; wherein each of $R^6$ and $R^7$ is independently selected from C1-C8 alkyl; and wherein $Ar^2$ is selected from aryl and heteroaryl and substituted with 0, 1, 2, or 3 groups independently selected from halogen and C1-C8 alkyl.

In one aspect, methods of making a compound having a structure represented by a formula selected from:

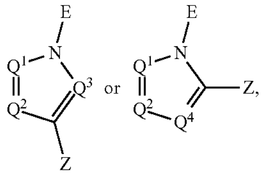

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; or wherein $R^1$ and $R^2$ are optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; wherein Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —$NNR^4$, —OC(═O)$R^5$, and $Ar^1$; wherein $R^4$ is selected from hydrogen and C1-C8 alkyl; wherein $R^5$ is selected from C1-C8 alkyl; and wherein $Ar^1$ is a 3- to 6-membered heterocycle substituted with 0, 1, 2, or 3 groups independently selected from halogen and C1-C8 alkyl, the method comprising the steps of: (a) reacting a compound having a structure represented by a formula selected from:

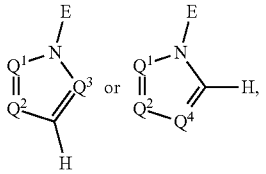

with a nucleophile selected from water, ammonia, a halide, a cyanide, an alcohol, a thiol, an amine, a hydrazine, a carbamate, a carboxylic acid, and an alkene, in the presence of a catalytically effective amount of an acridinium photocatalyst; and (b) reacting with an oxidant, thereby forming the compound are disclosed. In a further aspect, the electron donating group is selected from —OH, —SH, —$NH_2$, C1-C8 alkyl, C1-C8 alkoxy, C1-C8 thioalkoxy, C1-C8 silyloxy, C1-C8 alkylamino, (C1-C8)(C1-C8) dialkylamino, —OC(═O)$R^6$, —NHC(═O)$R^7$, —$OAr^2$, and $Ar^2$; wherein each of $R^6$ and $R^7$ is independently selected from C1-C8 alkyl; and wherein $Ar^2$ is selected from aryl and heteroaryl and substituted with 0, 1, 2, or 3 groups independently selected from halogen and C1-C8 alkyl. In a still further aspect, the electron donating group is selected from —OH, —SH, —$NH_2$, C1-C8 alkyl, C1-C8 alkoxy, C1-C8 thioalkoxy, C1-C8 alkylamino, (C1-C8)(C1-C8) dialkylamino, —OC(═O)$R^6$, —NHC(═O)$R^7$, and $Ar^2$; wherein each of $R^6$ and $R^7$ is independently selected from C1-C8 alkyl; and wherein $Ar^2$ is selected from aryl and heteroaryl and substituted with 0, 1, 2, or 3 groups independently selected from halogen and C1-C8 alkyl.

In a further aspect, the catalytically effective amount is of from about 0.01 mol % to about 15 mol %. In a still further aspect, the catalytically effective amount is of from about 0.01 mol % to about 12 mol %. In yet a further aspect, the catalytically effective amount is of from about 0.01 mol % to about 10 mol %. In an even further aspect, the catalytically effective amount is of from about 0.01 mol % to about 7 mol %. In a still further aspect, the catalytically effective amount is of from about 0.01 mol % to about 5 mol %. In yet a further aspect, the catalytically effective amount is of from about 0.01 mol % to about 2 mol %. In an even further aspect, the catalytically effective amount is of from about 0.01 mol % to about 1 mol %. In a still further aspect, the catalytically effective amount is of from about 0.01 mol % to about 0.1 mol %.

In a further aspect, the catalytically effective amount is of from about 0.1 mol % to about 10 mol %. In a still further aspect, the catalytically effective amount is of from about 0.1 mol % to about 7 mol %. In a still further aspect, the catalytically effective amount is of from about 0.1 mol % to about 5 mol %. In yet a further aspect, the catalytically effective amount is of from about 0.1 mol % to about 2 mol %. In an even further aspect, the catalytically effective amount is of from about 0.1 mol % to about 1 mol %. In a still further aspect, the catalytically effective amount is 5 mol %.

In a further aspect, the catalytically effective amount is of from about 0.1 mol % to about 15 mol %. In a still further aspect, the catalytically effective amount is of from about 1 mol % to about 15 mol %. In yet a further aspect, the catalytically effective amount is of from about 2 mol % to about 15 mol %. In an even further aspect, the catalytically effective amount is of from about 5 mol % to about 15 mol %. In a still further aspect, the catalytically effective amount is of from about 7 mol % to about 15 mol %. In yet a further aspect, the catalytically effective amount is of from about 10 mol % to about 15 mol %. In an even further aspect, the catalytically effective amount is of from about 12 mol % to about 15 mol %.

In a further aspect, the acridinium photocatalyst has a structure represented by a formula:

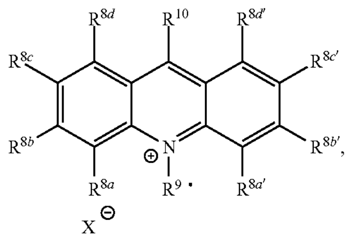

wherein X is selected from $BF_4$, TfO, $PF_6$, and $ClO_4$; wherein each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino, and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; wherein $R^9$ is selected from C1-C4 alkyl and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; and wherein $R^{10}$ is selected from C1-C4 alkyl and phenyl substituted with 0, 1, 2, or 3 groups independently selected from halogen and C1-C4 alkyl.

In a further aspect, the acridinium photocatalyst has a structure selected from:

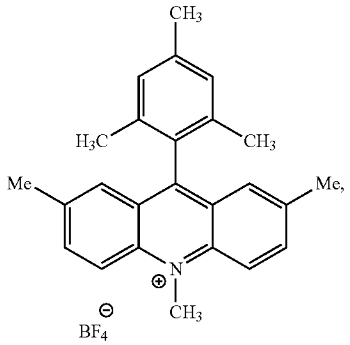

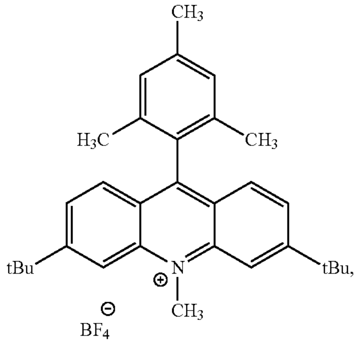

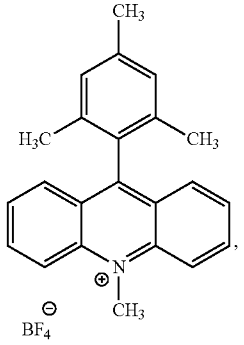

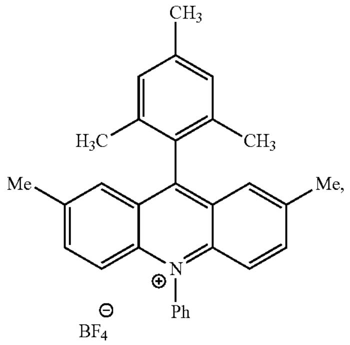

-continued

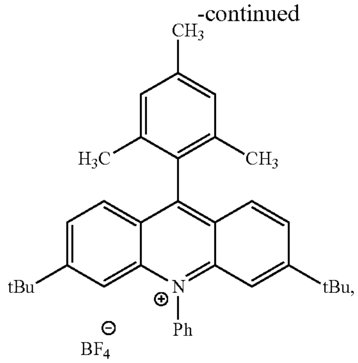

and

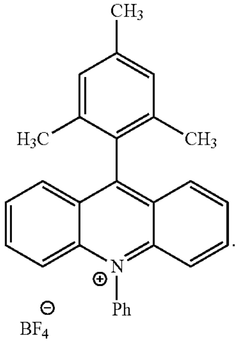

In a further aspect, the acridinium photocatalyst has a structure:

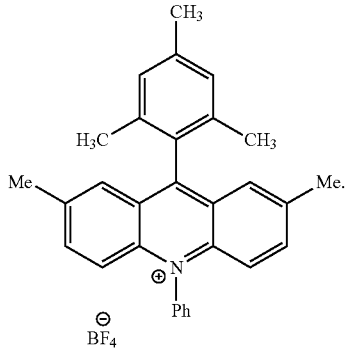

As used herein, the term "nucleophile" refers to a molecule, atom, or ion that is capable of forming a chemical bond to its reaction partner by donating electrons. Exemplary nucleophiles are well known by those skilled in the art and include, but are not limited to, water, ammonia, halides, cyanides, alcohols, thiols, amines, hydrazines, carbamates, carboxylic acids, and alkenes.

In a further aspect, the nucleophile is a halide. Exemplary halides are well known by those skilled in the art and include, but are not limited to, ammonium fluoride, cesium fluoride, lithium chloride, triethylamine hydrochloride, and triethylamine hydrofluoride.

In a further aspect, the nucleophile is an amine. Exemplary amines include, but are not limited to, ammonium bicarbonate.

As used herein the terms "oxidant" and "oxidizing agent" refer to any species that is capable of accepting or taking electrons from another species. Exemplary oxidants are well known by those skilled in the art and include, but are not limited to, molecular oxygen, 2,2,6,6-tetramethyl-1-piperidinyloxy radical (TEMPO), ozone, and hydrogen peroxide. In a further aspect, the oxidant is molecular oxygen. In a still further aspect, the oxidant is TEMPO. In yet a further aspect, the TEMPO is in solution with the acridinium photocatalyst.

In a further aspect, the method further comprises reacting the compound and the nucleophile in the presence of a catalytically effective amount of an additive. In a still further aspect, the additive is selected from TEMPO, N-hydroxyphthalimide, galvinoxyl radical, 2,2-diphenyl-1-picrylhydrazyl (DPPH), 9-azabicyclo[3.3.1] nonane N-oxyl radical (ABNO), and 2,6-di-tert-butyl-4-methylphenol (BHT). In yet a further aspect, the additive is TEMPO. In an even further aspect, the TEMPO is in solution with the acridinium photocatalyst.

In a further aspect, the catalytically effective amount is of from about 0.01 mol % to about 10 mol %. In a still further aspect, the catalytically effective amount is of from about 0.01 mol % to about 7 mol %. In yet a further aspect, the catalytically effective amount is of from about 0.01 mol % to about 5 mol %. In an even further aspect, the catalytically effective amount is of from about 0.01 mol % to about 2 mol %. In a still further aspect, the catalytically effective amount is of from about 0.01 mol % to about 1 mol %. In yet a further aspect, the catalytically effective amount is of from about 0.01 mol % to about 0.1 mol %.

In a further aspect, the catalytically effective amount is of from about 0.1 mol % to about 5 mol %. In a still further aspect, the catalytically effective amount is of from about 0.1 mol % to about 2 mol %. In yet a further aspect, the catalytically effective amount is of from about 0.1 mol % to about 1 mol %. In an even further aspect, the catalytically effective amount is 2 mol %.

In a further aspect, the catalytically effective amount is of from about 0.1 mol % to about 10 mol %. In a still further aspect, the catalytically effective amount is of from about 1 mol % to about 10 mol %. In yet a further aspect, the catalytically effective amount is of from about 2 mol % to about 10 mol %. In an even further aspect, the catalytically effective amount is of from about 5 mol % to about 10 mol %. In a still further aspect, the catalytically effective amount is of from about 7 mol % to about 10 mol %.

In a further aspect, the method further comprises reacting the compound and the nucleophile in the presence of visible light. In a still further aspect, the visible light is from about 365 nm to about 480 nm. In yet a further aspect, the visible light is from about 365 nm to about 450 nm. In an even further aspect, the visible light is from about 365 nm to about 420 nm. In a still further aspect, the visible light is from about 365 nm to about 400 nm. In yet a further aspect, the visible light is from about 365 nm to about 380 nm. In an even further aspect, the visible light is from about 380 nm to about 480 nm. In a still further aspect, the visible light is from about 400 nm to about 480 nm. In yet a further aspect, the visible light is from about 420 nm to about 480 nm. In an even further aspect, the visible light is from about 450 nm to about 480 nm.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Route I and Route II, as described and exemplified below. The following examples are provided so that the invention might be more fully understood, are illustrative only, and should not be construed as limiting.

1. Route I

In one aspect, para-substituted arenes can be prepared as shown below.

SCHEME 1A.

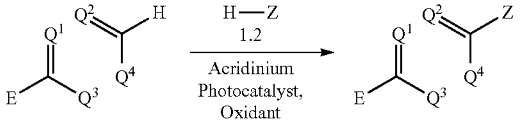

1.1 1.3

Compounds are represented in generic form, with substituents as noted in compound descriptions elsewhere herein. A more specific example is set forth below.

SCHEME 1B.

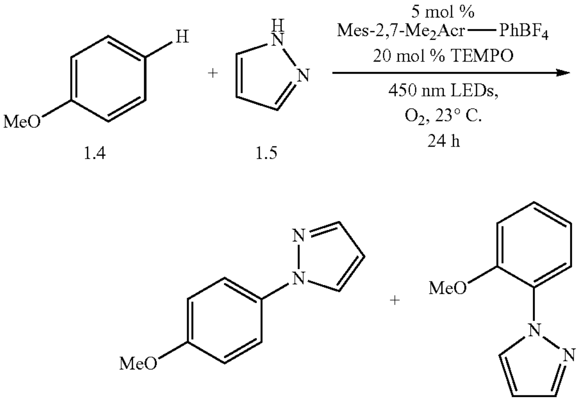

1.4 1.5

1.6 1.7

8.8:1

1.6:1.7

In one aspect, compounds of type 1.3, and similar compounds, can be prepared according to reaction Scheme 1B above. Thus, compounds of type 1.6 can be prepared by an aromatic C—H functionalization reaction of an appropriate arene, e.g., 1.4 as shown above. Appropriate arenes are commercially available or prepared by methods known to one skilled in the art. The aromatic C—H functionalization reaction is carried out in the presence of an appropriate amine, e.g., 1.5 as shown above, which is commercially available or prepared by methods known to one skilled in the art, an appropriate catalyst, e.g., 5 mol % Mes-2,7-Me$_2$Acr-PhBF$_4$ and 20 mol % TEMPO, and an appropriate oxidant, e.g., molecular oxygen, at an appropriate temperature, e.g., 23° C., for an appropriate period of time, e.g., 24 h. As can be appreciated by one skilled in the art, the above reaction provides an example of a generalized approach wherein compounds similar in structure to the specific reactants above (compounds similar to compounds of type 1.4 and 1.5), can be substituted in the reaction to provide para-substituted arenes similar to Formula 1.6.

Thus, in one aspect, the invention relates to a method of making a compound, the method comprising the step of reacting a compound having a structure represented by a formula:

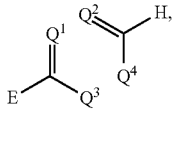

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)NR$^{3a}$R$^{3b}$; or wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)NR$^{3a}$R$^{3b}$; wherein each of $R^{3a}$ and $R^{3b}$ is independently selected from hydrogen and C1-C4 alkyl; with a second compound having a structure represented by a formula:

H—Z, wherein Z is selected from halogen, —CN, —NH$_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —NNR$^4$, —OC(═O)R$^5$, and Ar$^1$; wherein $R^4$ is selected from hydrogen and C1-C8 alkyl; wherein $R^5$ is selected from C1-C8 alkyl; and wherein Ar$^1$ is a 3- to 6-membered heterocycle substituted with 0, 1, 2, or 3 groups independently selected from halogen and C1-C8 alkyl; in the presence of a catalytically effective amount of an acridinium photocatalyst and an oxidant, thereby forming a para-substituted arene having a structure represented by a formula:

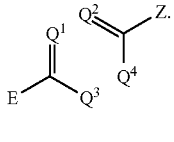

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

2. Route II

In one aspect, ortho-substituted arenes can be prepared as shown below.

SCHEME 2A.

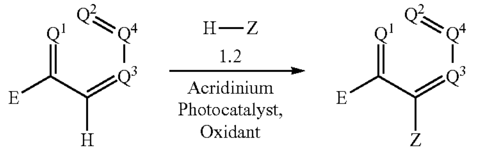

2.1 2.2

Compounds are represented in generic form, with substituents as noted in compound descriptions elsewhere herein. A more specific example is set forth below.

SCHEME 2B.

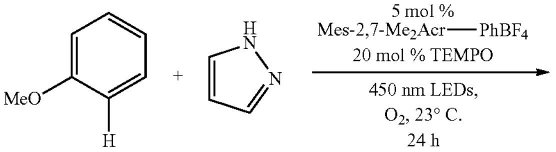

1.4 1.5

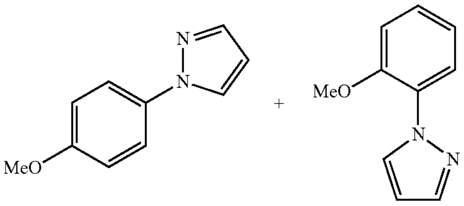

1.6 1.7

8.8:1
1.6:1.7

In one aspect, compounds of type 2.2, and similar compounds, can be prepared according to reaction Scheme 2B above. Thus, compounds of type 1.7 can be prepared by an aromatic C—H functionalization reaction of an appropriate arene, e.g., 1.4 as shown above. Appropriate arenes are commercially available or prepared by methods known to one skilled in the art. The aromatic C—H functionalization reaction is carried out in the presence of an appropriate amine, e.g., 1.5 as shown above, which is commercially available or prepared by methods known to one skilled in the art, an appropriate catalyst, e.g., 5 mol % Mes-2,7-$Me_2$Acr-$PhBF_4$ and 20 mol % TEMPO, and an appropriate oxidant, e.g., molecular oxygen, at an appropriate temperature, e.g., 23° C., for an appropriate period of time, e.g., 24 h. As can be appreciated by one skilled in the art, the above reaction provides an example of a generalized approach wherein compounds similar in structure to the specific reactants above (compounds similar to compounds of type 1.4 and 1.5), can be substituted in the reaction to provide ortho-substituted arenes similar to Formula 1.7.

Thus, in one aspect, the invention relates to a method of making a compound, the method comprising the step of reacting a compound having a structure represented by a formula:

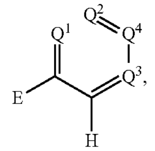

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; or wherein each of $Q^2$ and $Q^4$ is $CR^2$ and wherein each occurrence of $R^2$ are optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and —C(═O)$NR^{3a}R^{3b}$; with a second compound having a structure represented by a formula:

H—Z, wherein Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —$NNR^4$, —OC(═O)$R^5$, and $Ar^1$; wherein $R^4$ is selected from hydrogen and C1-C8 alkyl; wherein $R^5$ is selected from C1-C8 alkyl; and wherein $Ar^1$ is a 3- to 6-membered heterocycle substituted with 0, 1, 2, or 3 groups independently selected from halogen and C1-C8 alkyl; in the presence of a catalytically effective amount of an acridinium photocatalyst and an oxidant, thereby forming an ortho-substituted arene having a structure represented by a formula:

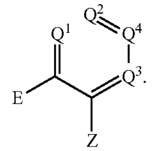

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

3. Route III

In one aspect, substituted arenes can be prepared as shown below.

SCHEME 3A.

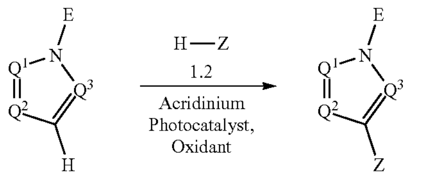

3.1 3.2

Compounds are represented in generic form, with substituents as noted in compound descriptions elsewhere herein. A more specific example is set forth below.

SCHEME 3B.

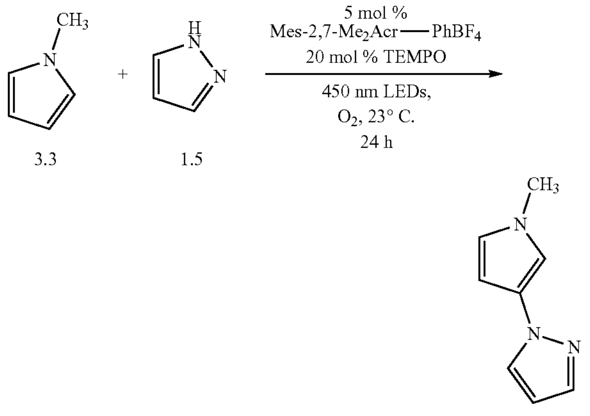

3.3 1.5

3.4

In one aspect, compounds of type 3.2, and similar compounds, can be prepared according to reaction Scheme 3B above. Thus, compounds of type 3.4 can be prepared by an aromatic C—H functionalization reaction of an appropriate arene, e.g., 3.3 as shown above. Appropriate arenes are commercially available or prepared by methods known to one skilled in the art. The aromatic C—H functionalization reaction is carried out in the presence of an appropriate amine, e.g., 1.5 as shown above, which is commercially available or prepared by methods known to one skilled in the art, an appropriate catalyst, e.g., 5 mol % Mes-2,7-$Me_2$Acr-$PhBF_4$ and 20 mol % TEMPO, and an appropriate oxidant, e.g., molecular oxygen, at an appropriate temperature, e.g., 23° C., for an appropriate period of time, e.g., 24 h. As can be appreciated by one skilled in the art, the above reaction provides an example of a generalized approach wherein compounds similar in structure to the specific reactants above (compounds similar to compounds of type 3.3 and 1.5), can be substituted in the reaction to provide ortho-substituted arenes similar to Formula 3.2.

Thus, in one aspect, the invention relates to a method of making a compound, the method comprising the step of reacting a compound having a structure represented by a formula:

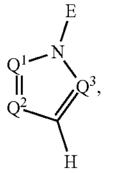

wherein E is an electron donating group; wherein each of $Q^1$ and $Q^3$ is independently selected from N and $CR^1$; wherein $Q^3$ is selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; or wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; or wherein each of $Q^2$ and $Q^4$ is $CR^2$ and wherein each occurrence of $R^2$ are optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and —C(═O)$NR^{3a}R^{3b}$; with a second compound having a structure represented by a formula:

H—Z, wherein Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —$NNR^4$, —OC(═O)$R^5$, and $Ar^1$; wherein $R^4$ is selected from hydrogen and C1-C8 alkyl; wherein $R^5$ is selected from C1-C8 alkyl; and wherein $Ar^1$ is a 3- to 6-membered heterocycle substituted with 0, 1, 2, or 3 groups independently selected from halogen and C1-C8 alkyl; in the presence of a catalytically effective amount of an acridinium photocatalyst and an oxidant, thereby forming a substituted arene having a structure represented by a formula:

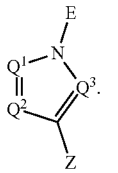

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

4. Route IV

SCHEME 4A.

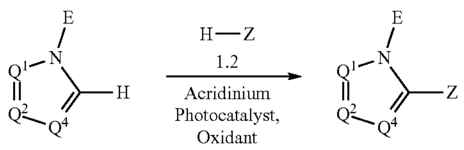

4.1 4.2

Compounds are represented in generic form, with substituents as noted in compound descriptions elsewhere herein. A more specific example is set forth below.

SCHEME 4B.

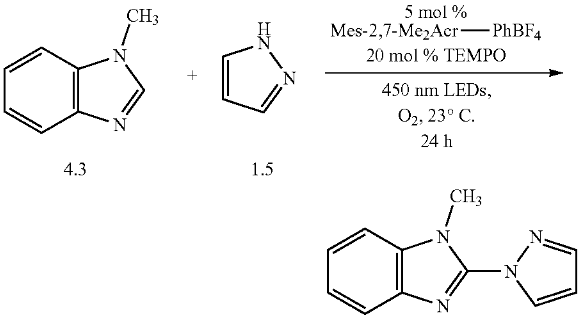

4.3 1.5

4.4

In one aspect, compounds of type 4.2, and similar compounds, can be prepared according to reaction Scheme 4B above. Thus, compounds of type 4.4 can be prepared by an aromatic C—H functionalization reaction of an appropriate arene, e.g., 4.3 as shown above. Appropriate arenes are commercially available or prepared by methods known to one skilled in the art. The aromatic C—H functionalization reaction is carried out in the presence of an appropriate amine, e.g., 1.5 as shown above, which is commercially available or prepared by methods known to one skilled in the art, an appropriate catalyst, e.g., 5 mol % Mes-2,7-$Me_2$Acr-$PhBF_4$ and 20 mol % TEMPO, and an appropriate oxidant, e.g., molecular oxygen, at an appropriate temperature, e.g., 23° C., for an appropriate period of time, e.g., 24 h. As can be appreciated by one skilled in the art, the above reaction provides an example of a generalized approach wherein compounds similar in structure to the specific reactants above (compounds similar to compounds of type 4.3 and 1.5), can be substituted in the reaction to provide ortho-substituted arenes similar to Formula 4.2.

Thus, in one aspect, the invention relates to a method of making a compound, the method comprising the step of reacting a compound having a structure represented by a formula:

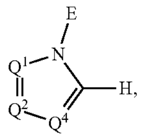

wherein E is an electron donating group; wherein $Q^1$ is selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; or wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; or wherein each of $Q^2$ and $Q^4$ is $CR^2$ and wherein each occurrence of $R^2$ are optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and —C(═O)$NR^{3a}R^{3b}$; with a second compound having a structure represented by a formula:

H—Z wherein Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —$NNR^4$, —OC(═O)$R^5$, and $Ar^1$; wherein $R^4$ is selected from hydrogen and C1-C8 alkyl; wherein $R^5$ is selected from C1-C8 alkyl; and wherein $Ar^1$ is a 3- to 6-membered heterocycle substituted with 0, 1, 2, or 3 groups independently selected from halogen and C1-C8 alkyl; in the presence of a catalytically effective amount of an acridinium photocatalyst and an oxidant, thereby forming a substituted arene having a structure represented by a formula:

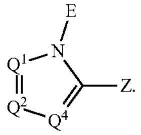

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

G. METHODS OF AMINATING ARENES

In one aspect, methods of aminating an activated arene in the presence of an acridinium photocatalyst are disclosed.

In one aspect, methods of aminating an activated arene in the absence of a transition metal catalyst are disclosed. Exemplary transition metal catalysts are well known to those of skill in the art and include, but are not limited to, palladium-, platinum-, cobalt-, manganese-, and nickel-based catalysts.

In a further aspect, the activated arene has a structure represented by a formula:

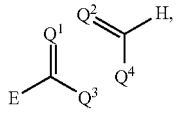

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; or wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; and wherein each of $R^{3a}$ and $R^{3b}$ is independently selected from hydrogen and C1-C4 alkyl.

In a further aspect, the activated arene has a structure represented by a formula:

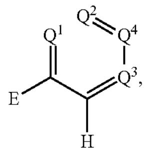

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; or wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; and wherein each of $R^{3a}$ and $R^{3b}$ is independently selected from hydrogen and C1-C4 alkyl.

In a further aspect, the activated arene has a structure represented by a formula selected from:

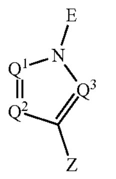

or

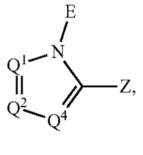

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; or wherein $R^1$ and $R^2$ are optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; wherein Z is selected from halogen, —CN, —$NH_2$, —OH, C1-C8 alkenyl, C1-C8 alkoxy, C1-C8 thioalkoxy, C1-C8 alkylamino, (C1-C8)(C1-C8) dialkylamino, arylamino, diarylamino, C1-C8 alkarylamino, —$NNR^4$, —OC(═O)$R^5$, and $Ar^1$; wherein $R^4$ is selected from hydrogen and C1-C8 alkyl; wherein $R^5$ is selected from C1-C8 alkyl; and wherein $Ar^1$ is a 3- to 6-membered heterocycle substituted with 0, 1, 2, or 3 groups independently selected from halogen and C1-C8 alkyl.

In a further aspect, the acridinium photocatalyst has a structure represented by a formula:

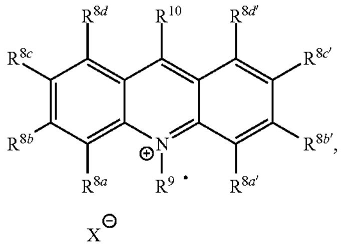

wherein X is selected from $BF_4$, TfO, $PF_6$, and $ClO_4$; wherein each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino, and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; wherein $R^9$ is selected from C1-C4 alkyl and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; and wherein $R^{10}$ is selected from C1-C4 alkyl and phenyl substituted with 0, 1, 2, or 3 groups independently selected from halogen and C1-C4 alkyl.

In a further aspect, the acridinium photocatalyst has a structure selected from:

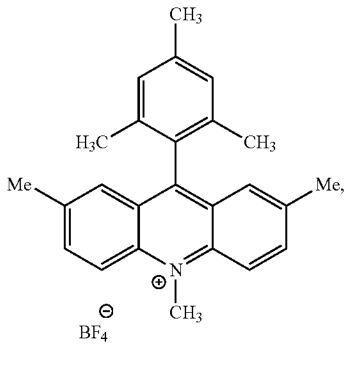

-continued

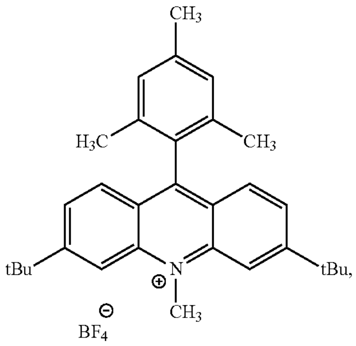

,

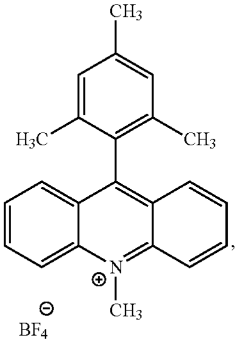

,

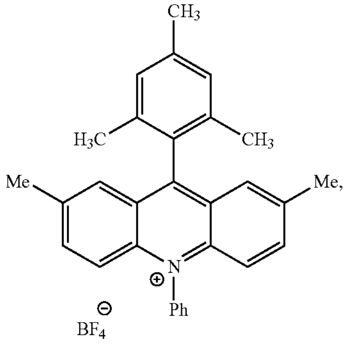

,

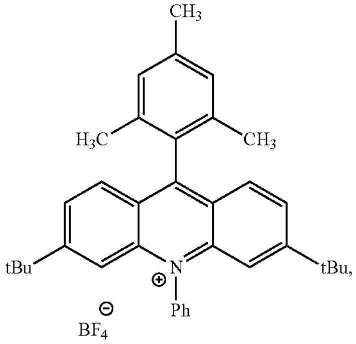

, and

-continued

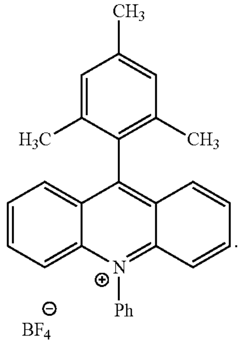

.

In a further aspect, the acridinium photocatalyst has a structure:

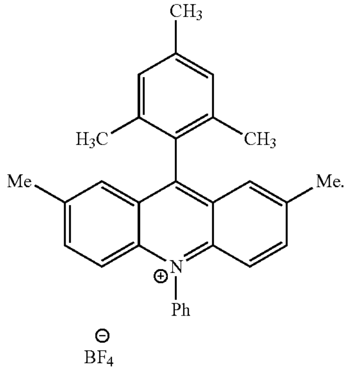

.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Route I and Route II, as described and exemplified below. The following examples are provided so that the invention might be more fully understood, are illustrative only, and should not be construed as limiting.

1. Route I

In one aspect, para-substituted anilines can be prepared as shown below.

SCHEME 5A.

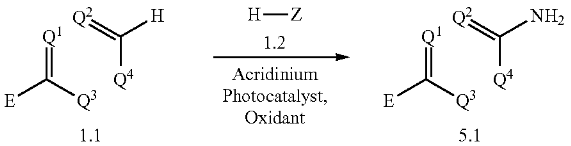

1.1 5.1

Compounds are represented in generic form, with substituents as noted in compound descriptions elsewhere herein. A more specific example is set forth below.

SCHEME 5B.

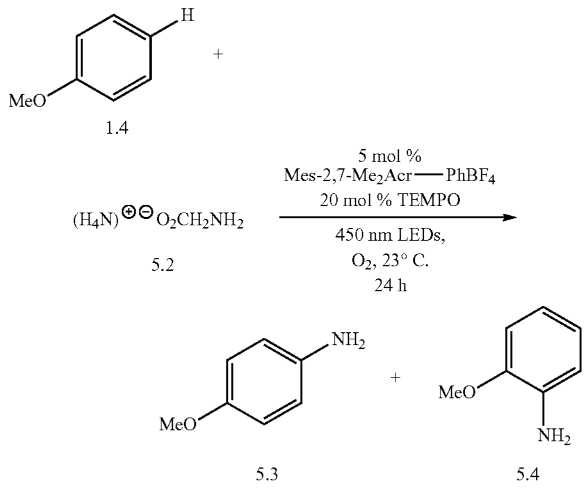

1.5:1
5.3: 5.4

In one aspect, compounds of type 5.1, and similar compounds, can be prepared according to reaction Scheme 5B above. Thus, compounds of type 5.3 can be prepared by an aromatic C—H functionalization reaction of an appropriate arene, e.g., 1.4 as shown above. Appropriate arenes are commercially available or prepared by methods known to one skilled in the art. The aromatic C—H functionalization reaction is carried out in the presence of an appropriate source of ammonia, e.g., ammonium salt 5.2 as shown above, which is commercially available or prepared by methods known to one skilled in the art, an appropriate catalyst, e.g., 5 mol % Mes-2,7-$Me_2$Acr-$PhBF_4$ and 20 mol % TEMPO, and an appropriate oxidant, e.g., molecular oxygen, at an appropriate temperature, e.g., 23° C., for an appropriate period of time, e.g., 24 h. As can be appreciated by one skilled in the art, the above reaction provides an example of a generalized approach wherein compounds similar in structure to the specific reactants above (compounds similar to compounds of type 1.4 and 5.2), can be substituted in the reaction to provide para-substituted anilines similar to Formula 5.3.

Thus, in one aspect, the invention relates to a method of making a compound, the method comprising the step of reacting a compound having a structure represented by a formula:

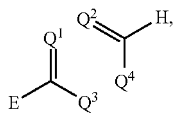

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; or wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; with a second compound having a structure represented by a formula:

H—Z, wherein Z is —$NH_2$; in the presence of a catalytically effective amount of an acridinium photocatalyst and an oxidant, thereby forming a para-substituted aniline having a structure represented by a formula:

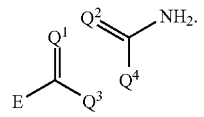

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

2. Route II

In one aspect, ortho-substituted anilines can be prepared as shown below.

SCHEME 6A.

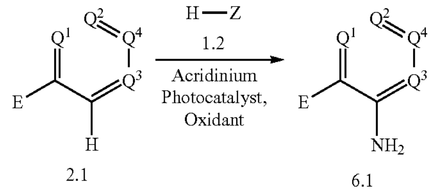

Compounds are represented in generic form, with substituents as noted in compound descriptions elsewhere herein. A more specific example is set forth below.

SCHEME 6B.

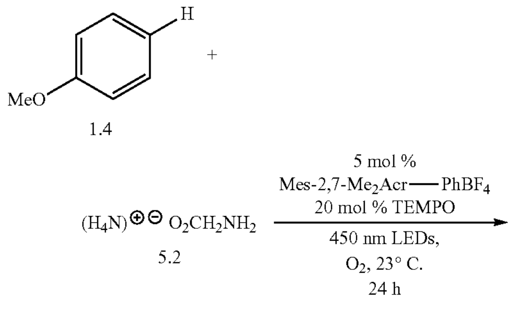

-continued

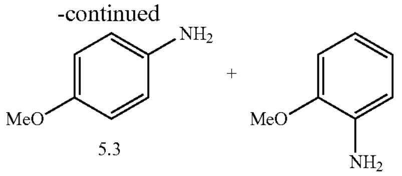

5.3

5.4

1.5:1
5.3:5.4

In one aspect, compounds of type 6.1, and similar compounds, can be prepared according to reaction Scheme 6B above. Thus, compounds of type 5.4 can be prepared by an aromatic C—H functionalization reaction of an appropriate arene, e.g., 1.4 as shown above. Appropriate arenes are commercially available or prepared by methods known to one skilled in the art. The aromatic C—H functionalization reaction is carried out in the presence of an appropriate source of ammonia, e.g., ammonium salt 5.2 as shown above, which is commercially available or prepared by methods known to one skilled in the art, an appropriate catalyst, e.g., 5 mol % Mes-2,7-$Me_2$Acr-$PhBF_4$ and 20 mol % TEMPO, and an appropriate oxidant, e.g., molecular oxygen, at an appropriate temperature, e.g., 23° C., for an appropriate period of time, e.g., 24 h. As can be appreciated by one skilled in the art, the above reaction provides an example of a generalized approach wherein compounds similar in structure to the specific reactants above (compounds similar to compounds of type 1.4 and 5.2), can be substituted in the reaction to provide ortho-substituted anilines similar to Formula 5.4.

Thus, in one aspect, the invention relates to a method of making a compound, the method comprising the step of reacting a compound having a structure represented by a formula:

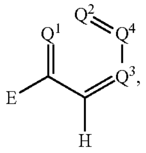

wherein E is an electron donating group; wherein each of $Q^1$ and $Q^3$ is independently selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; or wherein each of $Q^2$ and $Q^4$ is $CR^2$ and wherein each occurrence of $R^2$ are optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and —C(═O)$NR^{3a}R^{3b}$; with a second compound having a structure represented by a formula:

H—Z, wherein Z is —$NH_2$; in the presence of a catalytically effective amount of an acridinium photocatalyst and an oxidant, thereby forming an ortho-substituted aniline having a structure represented by a formula:

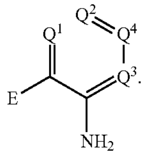

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

3. Route III

In one aspect, substituted arenes can be prepared as shown below.

SCHEME 7A.

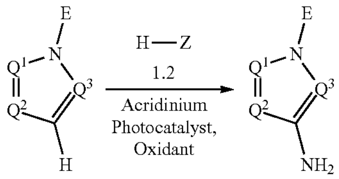

3.1

7.1

Compounds are represented in generic form, with substituents as noted in compound descriptions elsewhere herein. A more specific example is set forth below.

SCHEME 7B.

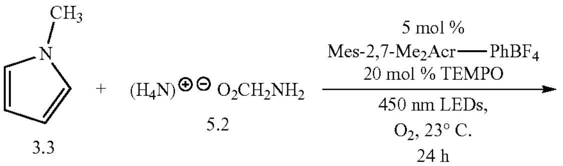

3.3

5.2

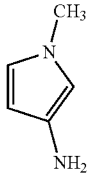

7.2

In one aspect, compounds of type 7.1, and similar compounds, can be prepared according to reaction Scheme 7B above. Thus, compounds of type 7.2 can be prepared by an aromatic C—H functionalization reaction of an appropriate arene, e.g., 3.3 as shown above. Appropriate arenes are commercially available or prepared by methods known to one skilled in the art. The aromatic C—H functionalization reaction is carried out in the presence of an appropriate source of ammonia, e.g., ammonium salt 5.2 as shown above, which is commercially available or prepared by methods known to one skilled in the art, an appropriate catalyst, e.g., 5 mol % Mes-2,7-$Me_2$Acr-$PhBF_4$ and 20 mol % TEMPO, and an appropriate oxidant, e.g., molecular oxygen, at an appropriate temperature, e.g., 23° C., for an appropriate period of time, e.g., 24 h. As can be appreciated by one skilled in the art, the above reaction provides an example of a generalized approach wherein compounds similar in structure to the specific reactants above (compounds similar to compounds of type 3.3 and 5.2), can be substituted in the reaction to provide substituted arenes similar to Formula 7.1.

Thus, in one aspect, the invention relates to a method of making a compound, the method comprising the step of reacting a compound having a structure represented by a formula:

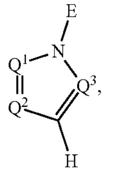

wherein E is an electron donating group; wherein each of $Q^1$ and $Q^3$ is independently selected from N and $CR^1$; wherein $Q^2$ is selected from N and $CR^2$; wherein each occurrence of $R^1$ and $R^2$ is independently selected from hydrogen, halogen, C1-C8 alkyl, C1-C8 alkoxy, and —C(═O)$NR^{3a}R^{3b}$; wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$; wherein each of $R^{3a}$ and $R^{3b}$ is independently selected from hydrogen and C1-C4 alkyl; or wherein each of $Q^2$ and $Q^4$ is $CR^2$ and wherein each occurrence of $R^2$ are optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and —C(═O)$NR^{3a}R^{3b}$; with a second compound having a structure represented by a formula:

H—Z, wherein Z is —$NH_2$; in the presence of a catalytically effective amount of an acridinium photocatalyst and an oxidant, thereby forming a substituted arene having a structure represented by a formula:

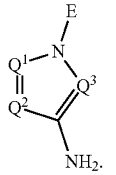

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

4. Route IV

In one aspect, substituted arenes can be prepared as shown below.

SCHEME 8A.

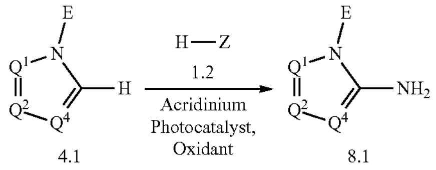

Compounds are represented in generic form, with substituents as noted in compound descriptions elsewhere herein. A more specific example is set forth below.

SCHEME 8B.

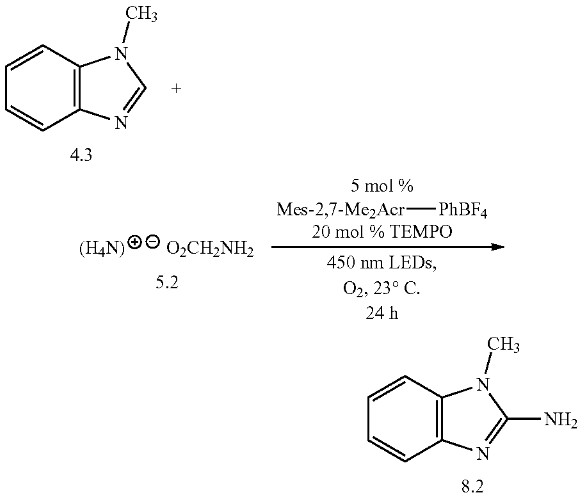

In one aspect, compounds of type 8.1, and similar compounds, can be prepared according to reaction Scheme 8B above. Thus, compounds of type 8.2 can be prepared by an aromatic C—H functionalization reaction of an appropriate arene, e.g., 4.3 as shown above. Appropriate arenes are commercially available or prepared by methods known to one skilled in the art. The aromatic C—H functionalization reaction is carried out in the presence of an appropriate source of ammonia, e.g., ammonium salt 5.2 as shown above, which is commercially available or prepared by methods known to one skilled in the art, an appropriate catalyst, e.g., 5 mol % Mes-2,7-$Me_2$Acr-$PhBF_4$ and 20 mol % TEMPO, and an appropriate oxidant, e.g., molecular oxygen, at an appropriate temperature, e.g., 23° C., for an appropriate period of time, e.g., 24 h. As can be appreciated by one skilled in the art, the above reaction provides an example of a generalized approach wherein compounds similar in structure to the specific reactants above (compounds similar to compounds of type 4.3 and 5.2), can be substituted in the reaction to provide substituted arenes similar to Formula 8.1.

Thus, in one aspect, the invention relates to a method of making a compound, the method comprising the step of reacting a compound having a structure represented by a formula:

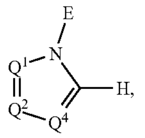

wherein E is an electron donating group; wherein $Q^1$ is selected from N and $CR^1$; wherein each of $Q^2$ and $Q^4$ is independently selected from N and $CR^2$; wherein each occurrence of $R^1$ and $R^2$ is independently selected from hydrogen, halogen, C1-C8 alkyl, C1-C8 alkoxy, and $—C(═O)NR^{3a}R^{3b}$; wherein $R^1$ and $R^2$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, C1-C8 alkyl, C1-C8 alkoxy, and $—C(═O)NR^{3a}R^{3b}$; wherein each of $R^{3a}$ and $R^{3b}$ is independently selected from hydrogen and C1-C4 alkyl; or wherein each of $Q^2$ and $Q^4$ is $CR^2$ and wherein each occurrence of $R^2$ are optionally covalently bonded and, together with the intermediate atoms, comprise a 5- to 6-membered cycle or heterocycle substituted with 0, 1, 2, or 3 groups independently selected from halogen, C1-C8 alkyl, C1-C8 alkoxy, and $—C(═O)NR^{3a}R^{3b}$; with a second compound having a structure represented by a formula:

H—Z, wherein Z is $—NH_2$; in the presence of a catalytically effective amount of an acridinium photocatalyst and an oxidant, thereby forming a substituted arene having a structure represented by a formula:

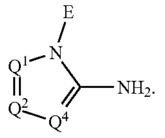

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

H. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Synthesis of 1-(4-Methoxyphenyl)-1H-Pyrazole

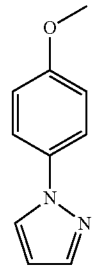

To a flame-dried 2 dram vial containing a Teflon-coated magnetic stir bar was added 12 mg of 9-mesityl-2,7-dimethyl-10-phenylacridinium tetrafluoroborate (25 μml, 0.05 equiv.), 68 mg of pyrazole (1.0 mmol, 2 equiv.), and 16 mg of (2,2,6,6-tetramethylpiperidin-1-yl)oxyl (0.1 mmol, 0.1 equiv.). Anhydrous 1,2-dichloroethane (DCE) was added (5.0 mL), followed by 54 μL of anisole (0.5 mmol, 1 equiv.). The vial was sealed with a Teflon-lined septum screw cap. The septum was pierced with a disposable steel needle connected to an oxygen-filled balloon. A vent needle was inserted and the reaction medium was sparged for 5 minutes by bubbling oxygen through the mixture. The vent needle was removed, and the oxygen balloon was maintained, providing approximately 1 atm of oxygen to the vial headspace for the course of the reaction. The vial was positioned on a stir plate approximately 10 cm from a Par38 LED lamp supplying blue light (λ=440-460 nm). After irradiation for 20 hours, the reaction mixture was passed through a short pad of silica gel, which was rinsed with an equal volume of dichloromethane. The crude product was concentrated in vacuo and purified by column chromatography on silica gel with hexanes/ethyl acetate (20:1 v/v) as the eluent. A colorless oil was obtained as a 8:1 mixture of 1-(4-methoxyphenyl)-1H-pyrazole and 1-(2-methoxyphenyl)-1H-pyrazole, yielding 69 mg of material (79% yield).

2. Substitution of Electron-Rich Arenes

It was envisioned that addition of various nucleophiles to electron-rich arenes could be achieved. The initial reactions were performed in aerobic conditions to determine whether molecular oxygen could act as a terminal oxidant. Molecular oxygen was chosen due to its wide abundance and the minimal waste produced in comparison to other heavily utilized oxidants, such as diacetoxyiodobenzene or metal co-catalysts.

The initial results are illustrated in Table 1. Anisole was utilized as the oxidizable arene and 1,2,4-triazole as the nucleophile. As shown below, the para-functionalized product was observed in a greater proportion than the ortho isomer. Using a significant excess of either the amine or the arene did not increase the yield appreciably (Entries 3 and 4). Yields using 1,2,4-triazole as the nucleophile appeared to stagnate around 40%. Without wishing to be bound by theory, it is hypothesized that this may be due to the lack of amine solubility. Manipulation of either the solvent, the base, the time, or the addition of a thiol did not appear to facilitate an increase in yield for the triazole amination reactions. Furthermore, when the vial was sparged with nitrogen or argon in place of oxygen, only trace amounts of product were observed (Entry 7).

TABLE 1

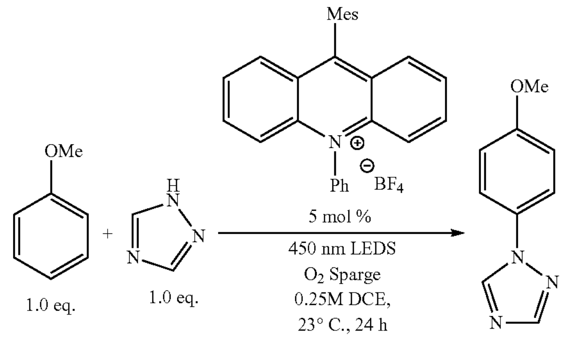

| Entry | Conditions | Yield[a] (%) | p:o |
|---|---|---|---|
| 1 | Standard conditions as shown above. | 31 | 6:1 |
| 2 | 15 mol % of $Ph_2S_2$ | 28 | 6:1 |
| 3 | 2 eq. amine | 22 | 6:1 |
| 4 | 2 eq. arene | 14 | 5:1 |
| 5 | No balloon, $O_2$ sparge | 17.9 | only para |
| 6 | $O_2$ balloon, no $O_2$ sparge | 28.1 | >100:1 |
| 7 | Sparge with argon | 0.3 | only para |

[a]GCMS yield vs. 1,3-dimethoxybenzene standard

Next, pyrazole was used as the nucleophile and other oxidants, such as benzoquinone, hypervalent iodine reagents, and potassium persulfate, were tested (Table 2). The solvent concentration was also varied (Entries 7-9).

TABLE 2

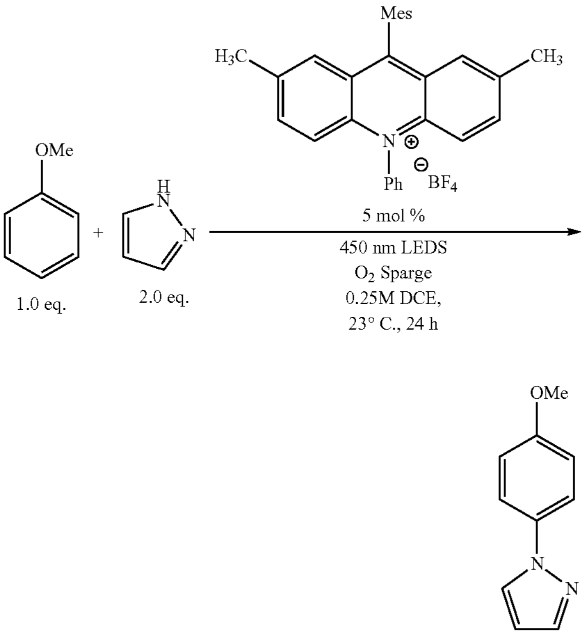

| Entry | Conditions | Yield (%) | p:o |
|---|---|---|---|
| 1 | Standard conditions as shown above. | 40[a] | 8.8:1 |
| 2 | No $O_2$ | <1 | — |
| 3 | $PhI(OAc)_2$, no photooxidant | <1 | — |
| 4 | Potassium persulfate | 9 | 2:1 |
| 5 | $PhI(OAc)_2$ | 20[b] | 5:1 |
| 6 | Benzoquinone, no $O_2$ | 8 | 7:1 |
| 7 | [0.35M] in DCE | 36 | 6.8:1 |
| 8 | [0.1M] in DCE | 41 | 5:1 |
| 9 | [0.05M] in DCE | 17 | 1.3:1 |
| 10 | 2.5 mmol scale | 30[c] | 5:1 |

[a]GCMS yield vs. 1,3-dimethoxybenzene standard;
[b]Isolated yield;
[c]NMR yield vs. hexamethyl disiloxane (HMDS) standard.

3. Evaluation of Substrate Scope

Various aryl ether derivatives were examined and the results illustrated in Table 3. Each reaction was performed using 5 mol % Mes-2,7-$Me_2$Acr-$PhBF_4$, 450 nm LEDs, $O_2$ sparge, and DCE at 23° C. Many substituted arenes were tolerant of the reaction conditions; however, for xylene and mesitylene, oxidation to the corresponding aldehyde was observed. It is also noteworthy that halogenated substrates were tolerated, as these substrates would be positioned for further functionalization.

TABLE 3

| Compound No. | Structure | Yield (%) |
|---|---|---|
| 9 | 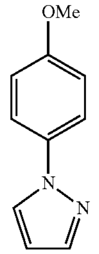 [SMILES: COc1ccc(-n2cccn2)cc1] | 40 (7:1 p:o) |
| 10 | 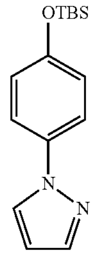 [SMILES: CC(C)(C)[Si](C)(C)Oc1ccc(-n2cccn2)cc1] | 31 (7:1 p:o) |
| 11 | 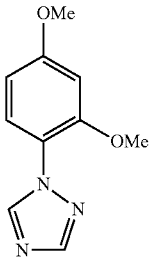 [SMILES: COc1ccc(-n2cncn2)c(OC)c1] | 48 |
| 11a | 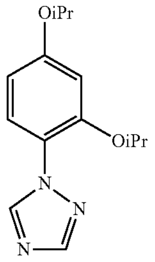 [SMILES: CC(C)Oc1ccc(-n2cncn2)c(OC(C)C)c1] | 48 |
| 12 | 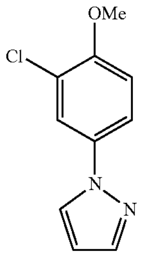 | 32 |
| 13 | 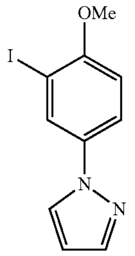 [SMILES: COc1ccc(-n2cccn2)cc1I] | 16 |

TABLE 3-continued

| Compound No. | Structure | Yield (%) |
|---|---|---|
| 14 | 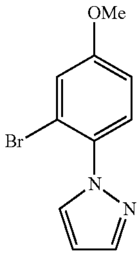 | 26 |

4. Evaluation of Photocatalysts

It was observed that the catalyst was not always stable to the aerobic conditions, as indicated by trace amounts of aldehyde detected by $^1H$ NMR from the oxidation of the mesityl substituent on the acridinium. Indeed, the oxidation of Mes-Acr-$MeBF_4$ under aerobic conditions has been previously reported (Verhoven et al. (2005) J. Am. Chem. Soc. 127, 16054). For this reason, several catalyst derivatives were explored (Table 4).

TABLE 4

| Catalyst | Structure |
|---|---|
| Mes-Acr-$MeBF_4$ | 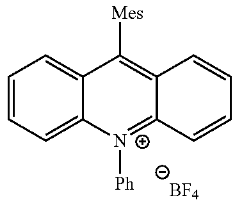 |
| Mes-2,7-$Me_2$Acr-$PhBF_4$ | 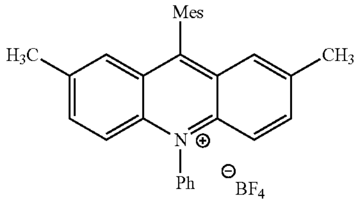 |
| Mes-3,6-$tBu_2$Acr-$PhBF_4$ | 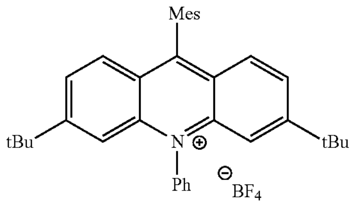 |
| Xylyl-Acr-$PhBF_4$ | 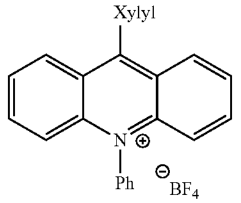 |

5. Screening of Additives

After isolating product 15 and resubmitting to reaction conditions, it was determined that the 1,2,4-triazole adduct could not be recovered. It was also determined that 15 had a lower oxidation potential compared to anisole ($Ev_{1/2}^{ox}$=1.87), indicating that it is more prone to oxidation (Scheme 9). When pyrazole adduct 9 was submitted to the photoredox conditions, only 15% of the product was recovered (Scheme 10).

SCHEME 9.

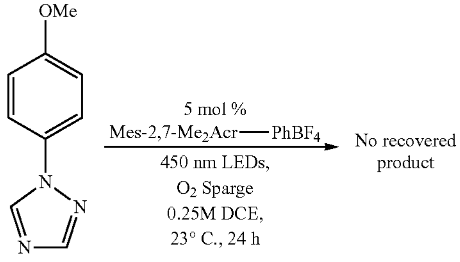

15

SCHEME 10.

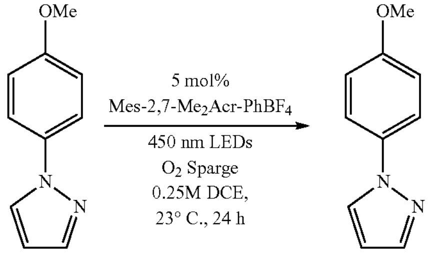

9

15% recovered product

In order to overcome these complications, a number of additives were screened (Table 5). A significant increase in the yield was observed when catalytic amounts of 2,2,6,6-tetramethyl-1-piperidinyloxy radical (TEMPO) were added to the reaction mixture. Other oxygen-centered radicals such as 9-azabicyclo[3.3.1] nonane N-oxyl radical (ABNO), or 2,6-di-tert-butyl-4-methylphenol (BHT) improved the reactivity of pyrazole with various arenes (Entries 6 and 7). A full equivalent of temponium was also attempted in the oxidizing conditions; however, this led to significant decrease in yield (Entry 5).

After further optimization using TEMPO as an additive, it was determined that more dilute conditions (e.g., 1.0M) resulted in a larger yield (Entry 9). Furthermore, use of a newly synthesized acridinium photocatalyst, Mes-3,6-$tBu_2Acr-PhBF_4$, in which the 3 and 6 positions on the acridinium were functionalized with tert-butyl groups, also improved yields. Without wishing to be bound by theory, this may be due to the tert-butyl groups blocking the catalyst from nucleophilic addition (Entry 11).

TABLE 5

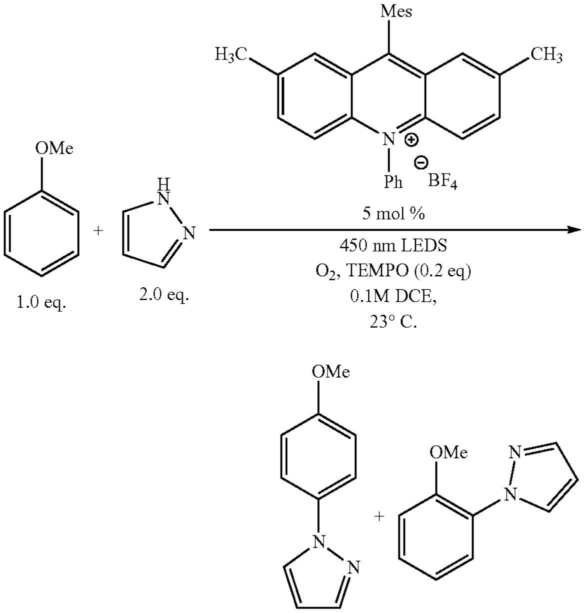

| Entry | Conditions | Yield[a] (%) | p:o |
|---|---|---|---|
| 1 | Standard conditions as shown above. | 79[c,d] | 8:1 |
| 2 | Standard conditions as shown above without TEMPO. | 40 | 8.8:1 |
| 3[b] | TEMPO (0.5 equiv.) | 33.5 | 7.6:1 |
| 4[b] | TEMPO (1.0 equiv.) | 28.3 | 7.9:1 |
| 5[b] | Temponium (1.0 equiv.) | 16 | 8.6:1 |
| 6 | ABNO instead of TEMPO | 60 | 7.8:1 |
| 7 | BHT instead of TEMPO | 42.2 | 6.4:1 |
| 8 | 0.5M DCE | 45.5 | 7.5:1 |
| 9 | 0.1M DCE | 57.6 | 8.1:1 |
| 10[b] | 2.5 mol % Mes-2,7-$Me_2$Acr-$PhBF_4$ | 48 | 8:1 |
| 11 | 5 mol % Mes-3,6-$tBu_2$Acr-$PhBF_4$ | 62.5 | 8.1:1 |
| 12 | Pyrazole (1.5 equiv.) | 53.1 | 8.5:1 |
| 13 | Pyrazole (1.0 equiv.) | 52.9 | 8.1:1 |
| 14[b] | 2.0 equiv. anisole, 1.0 equiv. pyrazole | 46.1 | 8:1 |
| 15 | Air sparge instead of $O_2$ | 35.0 | 9.3:1 |
| 16[b] | $N_2$ instead of $O_2$ | 47 | 8:1 |

aGCMS yield vs. 1,3-dimethoxybenzene standard;
[b]0.5M DCE;
[c]Isolated;
[d]5 mol % Mes-3,6-$tBu_2$Acr-$PhBF_4$.

6. Evaluation of Substrate Scope Using Tempo

The TEMPO additive was evaluated using a range of substrates and the results illustrated in Table 6. Each reaction was performed using 5 mol % Mes-2,7-$Me_2$Acr-$PhBF_4$, 450 nm LEDs, $O_2$ sparge, and DCE at 23° C. With some arenes, such as 1,3-dimethoxybenzene, the addition of TEMPO had a negative effect on yield. The amination was observed with some 1,2- and 1,3-disubstituted benzenes. Additionally, mesitylene and xylenes could be aminated without the observance of oxidation side products (compounds 21 and 22). This is a significant departure in reactivity compared to prior research. Indeed, previous attempts using a photoredox system without the oxygen-centered radical oxidized the methyl group to the corresponding aldehyde. This reactivity resembles the oxidation of toluene derivatives to the corresponding benzoic acids and aldehydes by Fukuzumi (Ohkubu et al. (2013) Chem. Intermed. 39, 205). With the addition of TEMPO, simple alkyl-substituted arene substrates were effectively aminated. Halogenated substrates such as 2-chloroanisole were also tolerant of the reaction conditions. Several amine nucleophiles have been shown to produce the desired amination products in generally good yields.

TABLE 6

| Compound No. | Structure | Yield (%) | p:o |
|---|---|---|---|
| 16 | 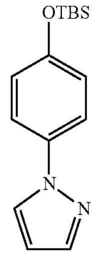 [SMILES: CC(C)(C)[Si](C)(C)Oc1ccc(-n2cccn2)cc1] | 21 | 7:1 |
| 17 | 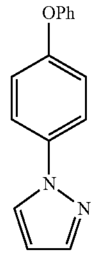 [SMILES: c1ccc(Oc2ccc(-n3cccn3)cc2)cc1] | 65 | 14:1 |
| 18 | 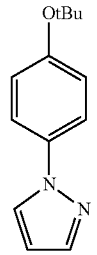 [SMILES: CC(C)(C)Oc1ccc(-n2cccn2)cc1] | 51 | 5.5:1 |
| 19 | 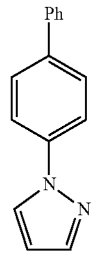 [SMILES: c1ccc(-c2ccc(-n3cccn3)cc2)cc1] | 41 | — |
| 20 | 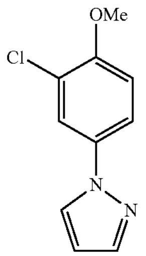 [SMILES: COc1ccc(-n2cccn2)cc1Cl] | 34 | — |

TABLE 6-continued
| Compound No. | Structure | Yield (%) | p:o |
|---|---|---|---|
| 21 | 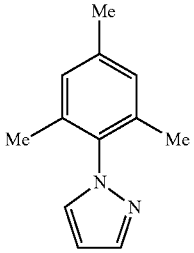 [SMILES: Cc1cc(C)c(-n2cccn2)c(C)c1] | 45 | — |
| 22 | 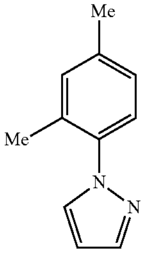 [SMILES: Cc1ccc(-n2cccn2)c(C)c1] | 30 | — |
| 23 | 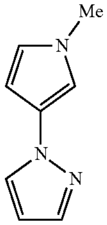 [SMILES: Cn1ccc(-n2cccn2)c1] | 16 | — |
| 24 | 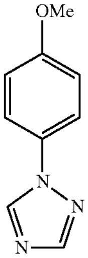 [SMILES: COc1ccc(-n2cncn2)cc1] | 46 | 3.3:1 |
| 25 | 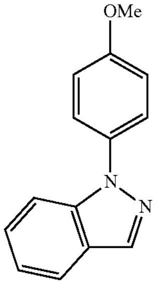 [SMILES: COc1ccc(-n2ncc3ccccc32)cc1] | 60 | 4:1 |
| 26 | 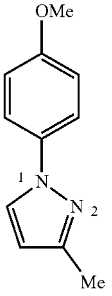 [SMILES: COc1ccc(-n2ccc(C)n2)cc1] | 59 (3.5:1 N1:N2) | 6:1 |

TABLE 6-continued
| Compound No. | Structure | Yield (%) | p:o |
| --- | --- | --- | --- |
| 27 | 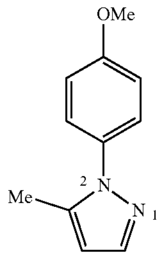 [SMILES: COc1ccc(-n2nccc2C)cc1] | | Single regioisomer |
| 28 | 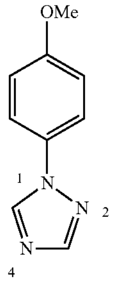 [SMILES: COc1ccc(-n2cncn2)cc1] | 81 (1:1 N1:N4) | 6:1 |
| 29 | 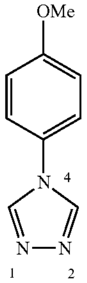 | | 6:1 |
| 30 | 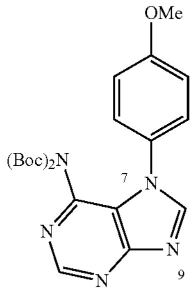 | 45 (2.5:1 N9:N7 | — |
| 31 | 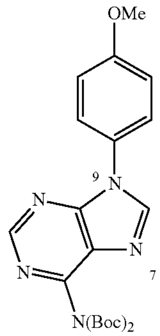 | | — |

TABLE 6-continued

| Compound No. | Structure | Yield (%) | p:o |
|---|---|---|---|
| 32 | 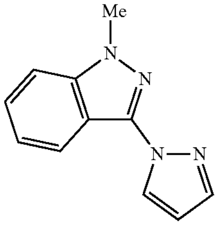 [SMILES: Cn1nc(-n2cccn2)c2ccccc21] | 40 | Single regioisomer |
| 33 | 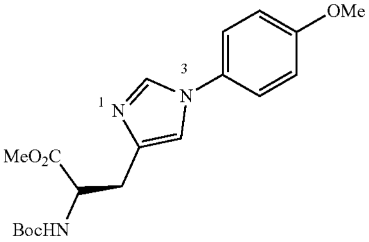 | 30 (1:1 N1:N3 | |
| 34 | 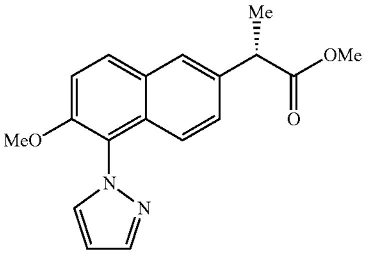 [SMILES: COC(=O)[C@@H](C)c1ccc2c(-n3cccn3)c(OC)ccc2c1] | 45 | Single regioisomer |

While it has been demonstrated that ether derived arenes as well as alkyl-substituted arenes tolerate these conditions, no anilines have yet to produce amination products. Without wishing to be bound by theory, this may be due to the low oxidation potentials of many commercially available anilines, the rapid back electron transfer, or the slow nucleophilic addition.

7. Proposed Mechanism of Photocatalytic Aerobic Aryl Amination

Without wishing to be bound by theory, it is hypothesized that, after excitation by light, organic photocatalyst Mes-2, 7-$Me_2$Acr-$PhBF_4$ can undergo SET from arene A, generating radical cation B (Scheme 11). Subsequent nucleophilic addition of the amine followed by oxidation affords the desired aminated arene C.

SCHEME 11.
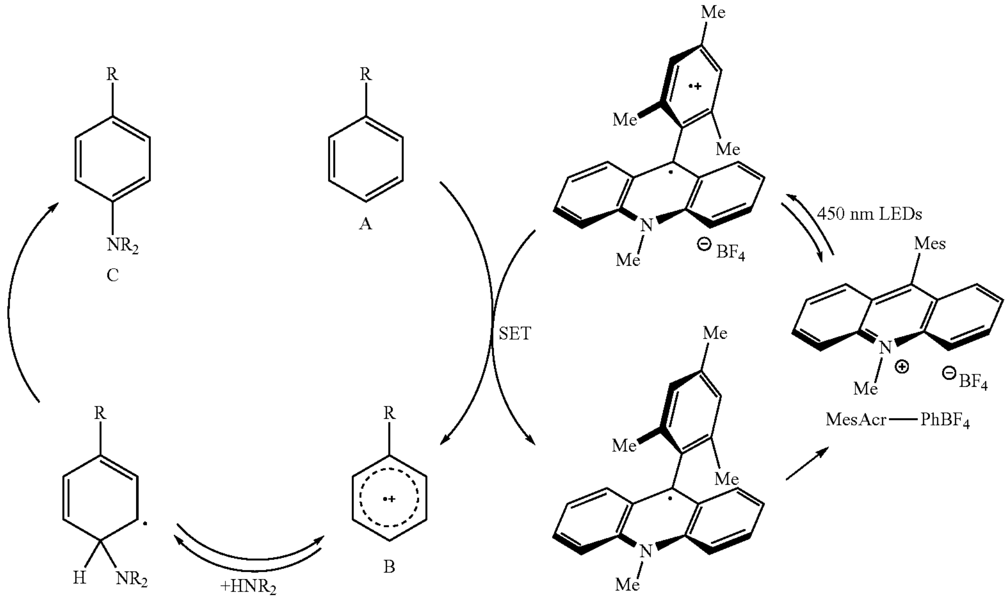
Without wishing to be bound by theory, it is hypothesized that TEMPO may serve as a hydrogen atom abstraction catalyst. A proposed mechanism of photocatalytic aerobic aryl amination using TEMPO is illustrated in Scheme 12 below.
SCHEME 12.
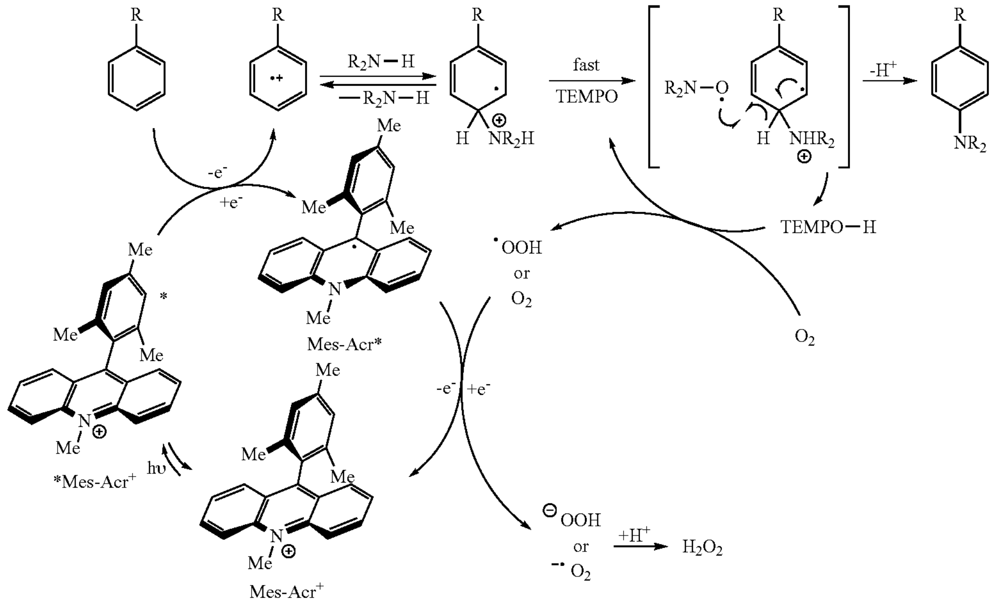

8. Counterion Effects

A variety of counterions were evaluated as shown in Scheme 5 below. Without wishing to be bound by theory, the results indicate that the pKa of the conjugate acid may be directly correlated with the reaction yield (FIG. 1).

9. Direct Synthesis of Anilines—Evaluation of Substrate Scope

A variety of substrates were chosen to evaluate the scope of this technique towards the direct syntheses of anilines. Each reaction was performed using 4.0 equivalents of ammonium carbamate, 5 mol % Mes-2,7-$Me_2$Acr-Ph$BF_4$, 20 mol % TEMPO, 450 nm LEDs, $O_2$ sparge, and DCE at 23° C. The resulting anilines and their respective yields are illustrated in Table 7.

TABLE 7

| Compound No. | Structure | Yield (%) | p:o |
|---|---|---|---|
| 35 | 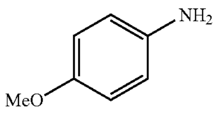 | 55 | 1.5:1 |
| 36 | 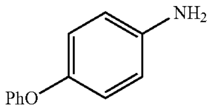 [SMILES: Nc1ccc(Oc2ccccc2)cc1] | 68 | 6:1 |
| 37 | 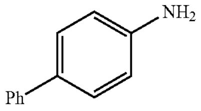 [SMILES: Nc1ccc(-c2ccccc2)cc1] | 51 | >10:1 |
| 38 | 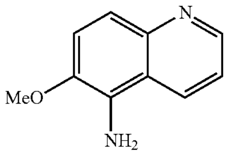 [SMILES: COc1ccc2ncccc2c1N] | 55 | — |
| 39* | 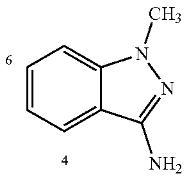 | 40 | — |
| 40 | 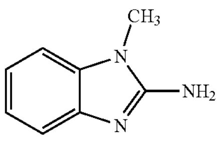 | 60 | — |

*7% of C4 and C6 isomers observed.

10. Cyanation

SCHEME 12.

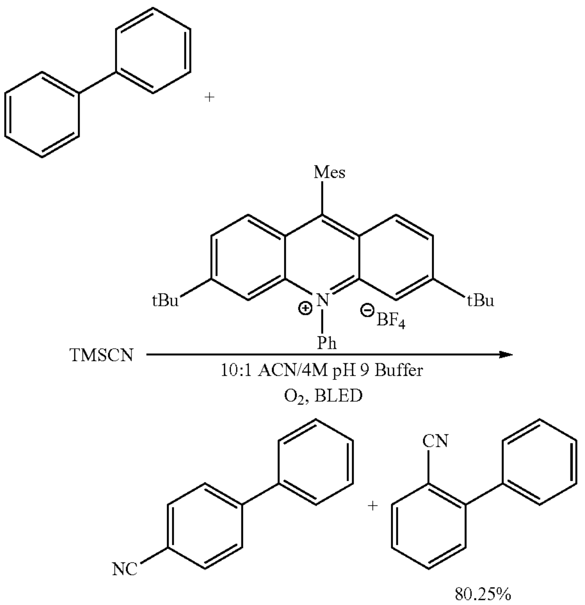

Biphenyl (77.11 mg, 0.5 mmol), di-tert-butyl-acridinium photocatalyst (14.34 mg, 0.025 mmol) and 0.5 ml of a 4 M, pH 9 phosphate buffer were dissolved in 5 ml of ACN. The reaction mixture was sealed and sparged for several minutes with $O_2$. After sparging, TMSCN (94.07 al, 0.75 mmol) was added and the biphasic mixture was stirred vigorously under blue-light irradiation for 18 hours. The reaction mixture was then concentrated by rotary evaporation and purified by column chromatography (1:19 EtOAc/Hex) to give and inseparable mixture of the ortho- and para-functionalized products (71.9 mg, 0.40 mmol, 80.25%). The ratio of isomers was roughly 5:1 in favor of the para-functionalized product.

Preliminary results show a promising method for the formation of benzonitriles taking advantage of a photoredox-mediated, C—H functionalization pathway. Without wishing to be bound by theory, it is believed that the reaction proceeds through the mechanism outlined in Scheme 13, below. The photocatalyst, Mes-Acr+ is promoted to excited state by blue-light irradiation where is can act as a single electron oxidant, oxidizing the arene, 1 to its corresponding radical cation (2). TMSCN is then employed as the nucleophilic source of cyanide to trap the radical cation. From here, the resulting radical (3) can be trapped with $O_2$ giving the aryl-peroxyl radical (4). Intramolecular H-atom abstraction from the peroxyl radical generates a hydroperoxyl radical and restores aromaticity to give the final benzonitriles product (5). The catalytic cycle is closed by the single electron reduction of $O_2$ by Mes-Acr· forming a superoxide radical and regenerating the active photocatalyst.

SCHEME 13.

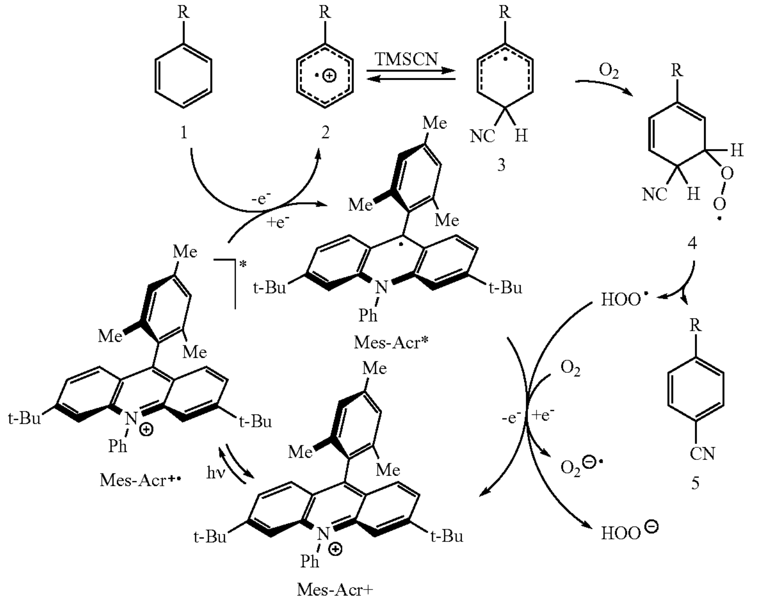

The pH 9 buffer is used for this system to inhibit the generation of HCN, which can retard or prohibit the reaction. Without wishing to be bound by theory, it is believed that additional cooxidants are not necessary to turn over the catalyst. Polar, non-halogenated solvents are preferred. Vigorous stirring enhances yield. The presence of water and/or inorganic base is preferred for the reaction. Without wishing to be bound by theory, it is believed that phase transfer catalysts are not necessary to help introduce —CN. Without wishing to be bound by theory, it is believed that changes in concentration have little effect on the reaction (e.g., yield). Both KCN and NaCN can be used, but studies indicate that TMSCN gives better results (e.g., yield). Exemplary alternative substrates for this reaction include:

SCHEME 14.

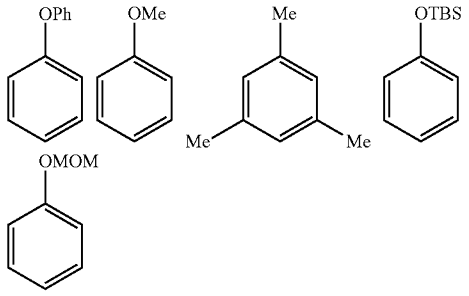

11. FLUORINATION

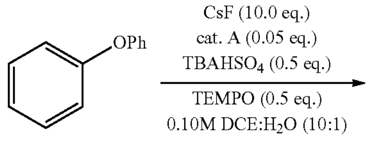

-continued

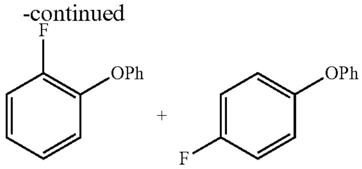

17.4% GC—MS yield (13:1 para:ortho)

cat. A

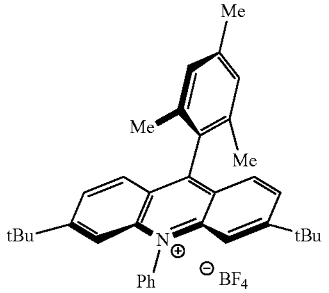

Key:
TBA: Tetrabutylammonium;
TEMPO: 2,2,6,6-Tetramethylpiperidine 1-oxyl;
DCE: Dichloroethane
Note:
3-bromotoluene was used as the GC—MS standard As illustrated in Scheme 14, above, fluorination can be accomplished. In a glovebox, cesium fluoride (10.0 eq.) was weighed and added to a dried glass vial (2 dram) equipped with a stir bar. This vial was removed from the glovebox and the substrate (1.0 eq.), $TBAHSO_4$ (0.5 eq.), and TEMPO (0.5 eq.) were weighed and added to the vial sequentially. The vial was then sealed with a Teflon-lined septum screw cap. The solvent mixture (10:1 $DCE:H_2O$) was then added. The septum was then pierced with a disposable steel needle connected to an oxygen-filled balloon. A vent needle was inserted and the reaction medium was sparged for 15 minutes by bubbling oxygen through the mixture. The vent needle was removed, and the oxygen balloon was maintained, providing approximately 1 atm of oxygen to the vial headspace for the course of the reaction. The reaction flask was then placed on a stir plate and illuminated with blue LED lamps (455 nm) for 24 h. After the reaction was completed, the reaction mixture was eluted through a silica plug and the eluent was analyzed by GC-MS, using 3-bromotoluene as the internal standard.

CsF was used as the nucleophile, and $TBAHSO_4$ was used as a phase transfer reagent to increase fluoride solubility in dichloroethane. Without wishing to be bound by theory, it is believed that the key activation step is the single electron oxidation of the arene by an acridinium photocatalyst (Mes-Acr+), as shown in Scheme 15, below. Illumination of the photocatalyst with blue light activates it to its excited state (Mes-Acr+*), where it becomes a potent oxidant. This species then oxidizes the substrate, rendering it susceptible to fluoride attack. (1 to 2). The resulting species can then be converted to the desired product by H-atom transfer to TEMPO, forming TEMPO-H. TEMPO-H can then be converted back to TEMPO by superoxide, which is generated from photocatalyst turnover via oxidation of Mes-Acre to Mes-Acr+.

SCHEME 16.

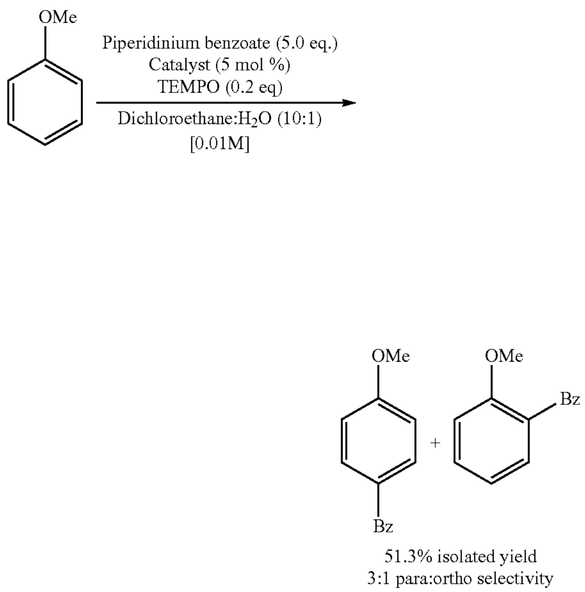

Scheme 15.

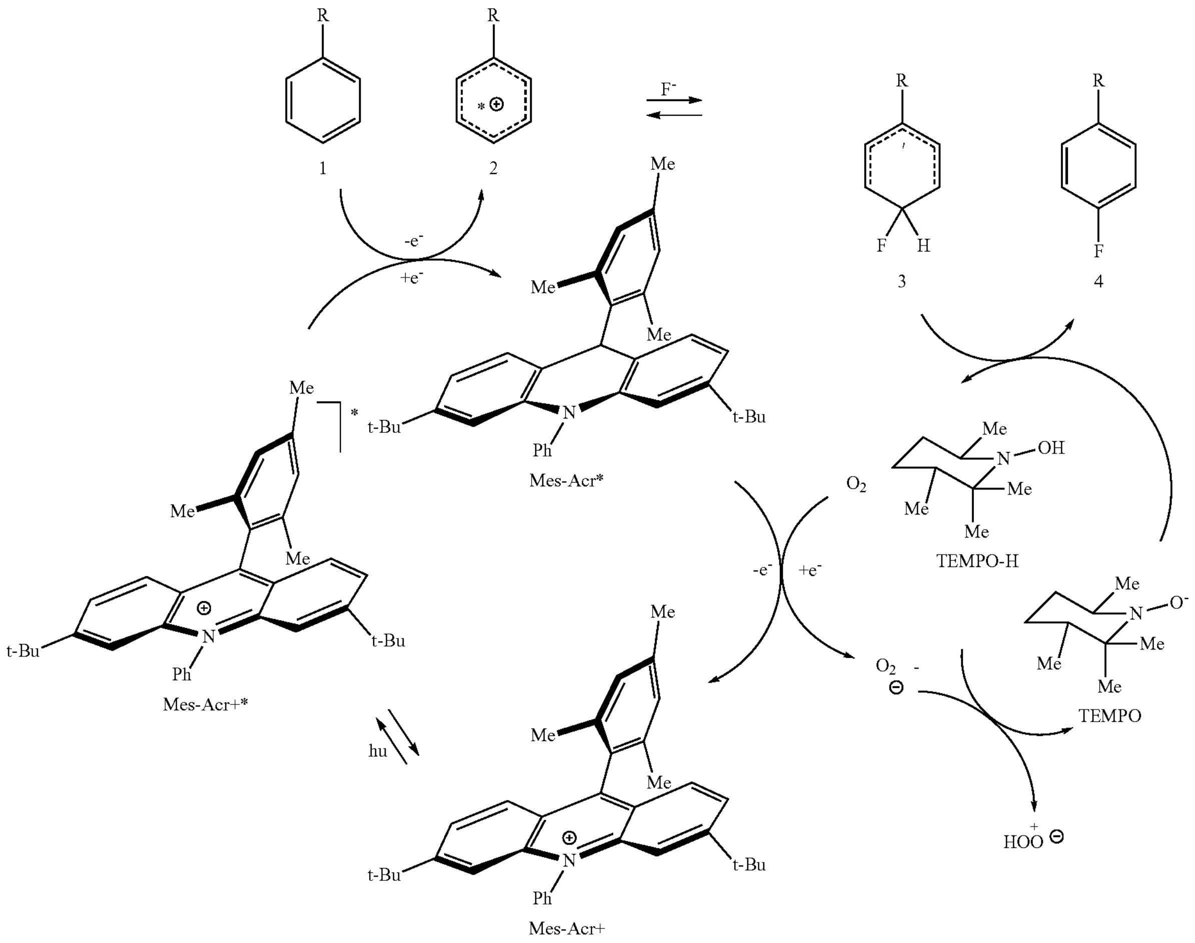

-continued

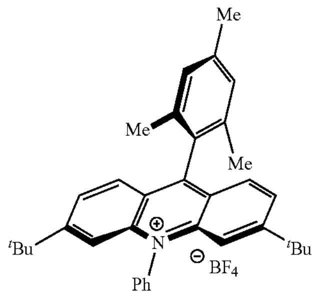

Catalyst

As shown in Scheme 16, above, oxygen nucleophiles can be used for direct C—H functionalization. Piperidinium benzoate (5.0 eq.), catalyst (5 mol %), and TEMPO (0.2 eq.) were weighed out and transferred to a flame-dried 20-mL scintillation vial that was equipped with a stir bar. The dichloroethane (9.00 mL) and deionized water (0.90 mL) were transferred to the vial via syringe, and the anisole (1.0 eq.) was transferred via microsyringe. The vial was capped with a rubber septum and sealed with Teflon tape. Oxygen was bubbled through the system for five minutes to sparge the yellow reaction mixture. The biphasic reaction was stirred vigorously for eighteen hours while being irradiated by 455 nm blue LED light and cooled by a fan. The reaction mixture was filtered through a silica plug, and the reaction vessel and silica were washed with dichloromethane and ethyl acetate. The crude product was characterized via GC-MS and $^1H$ NMR spectroscopy. Purification through column chromatography was performed using a 10% ethyl acetate in hexanes solvent system to yield 11.7 mg (0.05126 mmol) of the desired products (3:1 para:ortho selectivity) in a combined 51.3% isolated yield.

Screening revealed that benzoate salts had the ability to add to arenes. Success was seen when a piperidinium benzoate salt was used as the nucleophile and when the reaction was run at a more dilute concentration (e.g., 0.01M). Modest selectivity can be seen for the formation of the para product over the ortho product. Selectivity varies with substrate, as arenes with more hindered ortho positions display higher preferences for the para product. Without wishing to be bound by theory, Scheme 17 below shows the mechanism for the system. Oxidation of the arene (1) by the excited state acridinium catalyst (Mes-Acr+*) generates the radical cation intermediate (2) that undergoes nucleophilic attack by the benzoate anion. Generation of the product (4) occurs through the transfer of a hydrogen atom to TEMPO to form the TEMPO-H species. TEMPO is regenerated via a superoxide species that results from the oxidation of the radical acridinium (Mes-Acre) species back to the ground state photocatalyst (Mes-Acr+).

SCHEME 17.

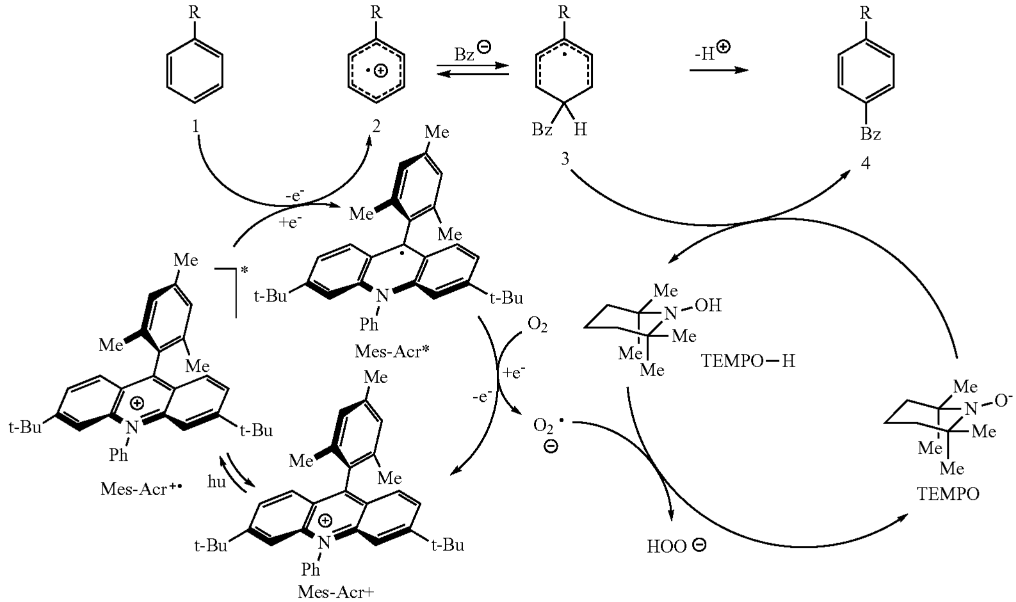

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

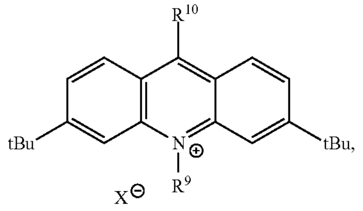

wherein X is selected from $BF_4$, TfO, $PF_6$, and $ClO_4$;
wherein $R^9$ is phenyl substituted with 1, 2, or 3 groups independently selected from halogen, —$CF_3$, —$NH_2$, C1-C4 alkyl, C1-C4 alkoxy, C1-C4 alkylamino, (C1-C4) (C1-C4) dialkylamino; and
wherein $R^{10}$ is selected from C1-C4 alkyl and phenyl substituted with 0, 1, 2, or 3 groups independently selected from halogen and C1-C4 alkyl.

2. The compound of claim 1, wherein X is $BF_4$.

3. The compound of claim 1, wherein $R^{10}$ is phenyl substituted with 0, 1, 2, or 3 groups independently selected from halogen and C1-C4 alkyl.

4. The compound of claim 1, wherein $R^{10}$ is phenyl substituted with 0, 1, 2, or 3 groups independently selected from C1-C4 alkyl.

5. The compound of claim 1, wherein the compound has a structure represented by a formula:

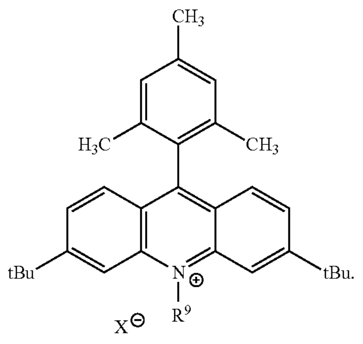

6. A catalyst system comprising an acridinium photocatalyst, a nucleophile, and an oxidant, wherein the acridinium photocatalyst is of the formula:

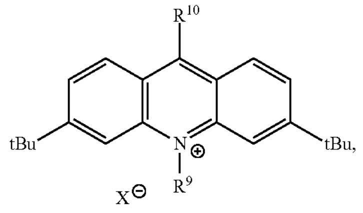

wherein X is selected from $BF_4$, TfO, $PF_6$, and $ClO_4$;
wherein $R^9$ is selected from C1-C4 alkyl and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4) (C1-C4) dialkylamino; and
wherein $R^{10}$ is selected from C1-C4 alkyl and phenyl substituted with 0, 1, 2, or 3 groups independently selected from halogen and C1-C4 alkyl.

7. The catalyst system of claim 6, further comprising a compound having a structure represented by a formula:

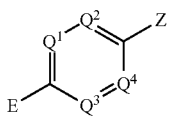

or

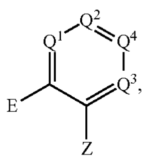

wherein E is an electron donating group;
wherein each of $Q^1$ and $Q^3$ is independently selected from N and $CR^1$; wherein each of $Q^2$ and $Q^4$ is independently selected from N and $CR^2$;
wherein each occurrence of $R^1$ and $R^2$ is independently selected from hydrogen, halogen, C1-C8 alkyl, C1-C8 alkoxy, and —C(═O) $NR^{3a}R^{3b}$; or wherein $R^1$ and $R^2$ are optionally covalently bonded and, together with the intermediate atoms, form a 5- to 6-membered cycle or heterocycle having 0, 1, or 2 heteroatoms and substituted with 0, 1, 2, or 3 groups independently selected from halogen, C1-C8 alkyl, C1-C8 alkoxy, and —C(═O)$NR^{3a}R^{3b}$;
wherein each of $R^{3a}$ and $R^{3b}$ is independently selected from hydrogen and C1-C4 alkyl; wherein Z is selected from halogen, —CN, —$NH_2$, —OH, C1-C8 alkenyl, C1-C8 alkoxy, C1-C8 thioalkoxy, C1-C8 alkylamino, (C1-C8) (C1-C8) dialkylamino, arylamino, diarylamino, C1-C8 alkarylamino, —$NNR^4$, —OC(═O)$R^5$, and $Ar^1$;
wherein $R^4$ is selected from hydrogen and C1-C8 alkyl;
wherein $R^5$ is selected from C1-C8 alkyl; and
wherein $Ar^1$ is a 3- to 6-membered heterocycle substituted with 0, 1, 2, or 3 groups independently selected from halogen and C1-C8 alkyl.

8. The catalyst system of claim 6, wherein X is $BF_4$.

9. The catalyst system of claim 6, wherein $R^9$ is C1-C4 alkyl.

10. The catalyst system of claim 6, wherein $R^9$ is methyl.

11. The catalyst system of claim 6, wherein $R^9$ is phenyl substituted with 0, 1, 2, or 3 groups independently selected from halogen, —$CF_3$, —$NH_2$, C1-C4 alkyl, C1-C4 alkoxy, C1-C4 alkylamino, (C1-C4) (C1-C4) dialkylamino.

12. The catalyst system of claim 6, wherein $R^9$ is unsubstituted phenyl.

13. The catalyst system of claim 6, wherein $R^{10}$ is phenyl substituted with 0, 1, 2, or 3 groups independently selected from halogen and C1-C4 alkyl.

14. The catalyst system of claim 6, wherein the acridinium photocatalyst has a structure represented by the formula:

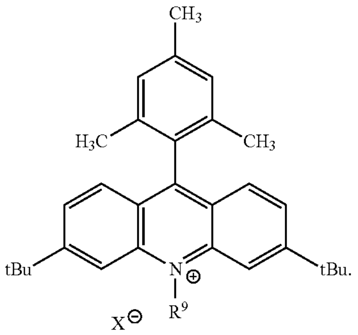

15. The catalyst system of claim 6, wherein the acridinium photocatalyst is selected from:

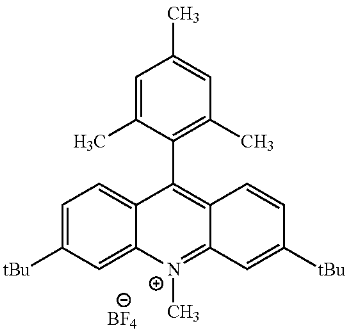

and

-continued

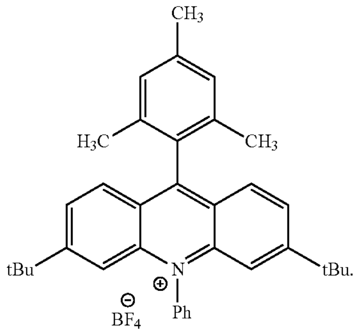

16. The catalyst system of claim 6, wherein the acridinium photocatalyst is:

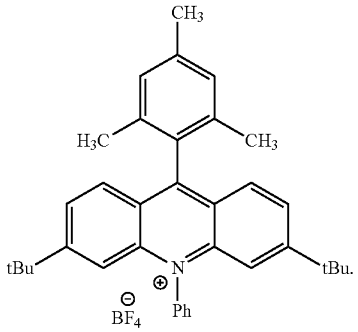

* * * * *